(12) United States Patent
Takeshima

(10) Patent No.: US 12,059,241 B2
(45) Date of Patent: *Aug. 13, 2024

(54) MEDICAL DATA PROCESSING APPARATUS, MAGNETIC RESONANCE IMAGING APPARATUS, AND LEARNED MODEL GENERATING METHOD

(71) Applicant: Canon Medical Systems Corporation, Otawara (JP)

(72) Inventor: Hidenori Takeshima, Kawasaki (JP)

(73) Assignee: Canon Medical Systems Corporation, Otawara (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/652,047

(22) Filed: Feb. 22, 2022

(65) Prior Publication Data

US 2022/0202306 A1    Jun. 30, 2022

Related U.S. Application Data

(63) Continuation of application No. 16/516,938, filed on Jul. 19, 2019, now Pat. No. 11,278,213, which is a
(Continued)

(30) Foreign Application Priority Data

Nov. 24, 2017  (JP) ................................ 2017-226243

(51) Int. Cl.
*G06N 20/00*      (2019.01)
*A61B 5/055*      (2006.01)
(Continued)

(52) U.S. Cl.
CPC ............ *A61B 5/055* (2013.01); *A61B 6/4241* (2013.01); *G01R 33/543* (2013.01);
(Continued)

(58) Field of Classification Search
CPC ..................................................... A61B 5/055
See application file for complete search history.

(56) References Cited

U.S. PATENT DOCUMENTS 9,265,441 B2    2/2016  Pereira
10,331,852 B2   6/2019  Dormer
(Continued)

FOREIGN PATENT DOCUMENTS

| JP | 11-31214 A | 2/1999 |
|----|-----------|--------|
| JP | 2015-33581 | 2/2015 |
| JP | 2019-111322 A | 7/2019 |

OTHER PUBLICATIONS

Extended European Search Report issued Jul. 6, 2021 in European Application No. 18881546.8.
(Continued)

*Primary Examiner* — Oneal R Mistry
(74) *Attorney, Agent, or Firm* — Oblon, McClelland, Maier & Neustadt, L.L.P.

(57) ABSTRACT

A medical data processing apparatus includes a memory and processing circuitry. The memory stores a learned model including an input layer to which first MR data and second MR data having the same imaging target as the first MR data and an imaging parameter different from the first MR data are inputted, an output layer from which third MR data is output with a missing portion of the first MR data restored, and at least one intermediate layer arranged between the input layer and the output layer. The processing circuitry generates third MR data relating to the subject, from the first MR data serving as a process target and relating to the subject and the second MR data relating to the subject and acquired by an imaging parameter different from the first MR data serving as the process target, in accordance with the learned model.

16 Claims, 30 Drawing Sheets

Related U.S. Application Data continuation of application No. PCT/JP2018/041193, filed on Nov. 6, 2018.

(51) Int. Cl.

| | | |
|---|---|---|
| *A61B 6/42* | (2024.01) | |
| *G01R 33/54* | (2006.01) | |
| *G01R 33/56* | (2006.01) | |
| *G06N 3/02* | (2006.01) | |
| G01R 33/561 | (2006.01) | |
| G06T 5/50 | (2006.01) | |
| G06T 5/73 | (2024.01) | |
| G06T 7/00 | (2017.01) | |
| G06T 11/00 | (2006.01) | |

(52) U.S. Cl.
CPC ........... *G01R 33/5602* (2013.01); *G06N 3/02* (2013.01); *G06N 20/00* (2019.01); *A61B 6/4291* (2013.01); *G01R 33/561* (2013.01); *G06T 5/50* (2013.01); *G06T 5/73* (2024.01); *G06T 7/0012* (2013.01); *G06T 11/003* (2013.01); *G06T 2207/10072* (2013.01); *G06T 2207/10088* (2013.01); *G06T 2207/20172* (2013.01); *G06T 2207/30004* (2013.01); *G06T 2210/41* (2013.01)

(56) References Cited

U.S. PATENT DOCUMENTS

| | | | |
|---|---|---|---|
| 10,600,184 B2 | 3/2020 | Golden | |
| 10,871,536 B2 | 12/2020 | Golden | |
| 11,517,197 B2* | 12/2022 | Zhou | G06T 11/005 |
| 2013/0121550 A1* | 5/2013 | Chang | A61B 5/055 |
| | | | 382/130 |
| 2015/0043795 A1 | 2/2015 | Rigie et al. | |
| 2016/0174902 A1* | 6/2016 | Georgescu | G06V 10/454 |
| | | | 600/408 |
| 2018/0144214 A1* | 5/2018 | Hsieh | G06T 7/0002 |
| 2018/0240219 A1* | 8/2018 | Mentl | G06N 3/08 |
| 2019/0049540 A1* | 2/2019 | Odry | G01R 33/543 |
| 2019/0172205 A1* | 6/2019 | Mao | G06T 7/0014 |
| 2019/0244399 A1* | 8/2019 | Li | G01R 33/56545 |
| 2019/0287674 A1 | 9/2019 | Nitta et al. | |
| 2020/0258227 A1* | 8/2020 | Liao | G06T 7/30 |
| 2020/0273215 A1* | 8/2020 | Wang | G06N 3/04 |

OTHER PUBLICATIONS

Jo Schlemper et al: "A Deep Cascade of Convolutional Neural Networks for Dynamic MR Image Reconstruction", arxiv.org, Cornell University Library, 201 Olin Library Cornell University Ithaca, NY 14853, Apr. 8, 2017 (Apr. 8, 2017), XP081280885.

Ying Song et al: "Reconstruction of magnetic resonance imaging by three-dimensional dual-dictionary learning", Magnetic Resonance in Medicine, vol. 71, No. 3, Apr. 2, 2013 (Apr. 2, 2013), pp. 1285-1298, XP055266961, US ISSN: 0740-3194, DOI: 10.1002/mrm.24734.

Gong E. et al: "Undersampled High-frequency Diffusion Signal Recovery Using Model-free Multi-scale Dictionary Learning", International Society for Magnetic Resonance in Medicine, ISMRM, 2030 Addison Street, 7th Floor, Berkeley, CA 94704 USA, No. 3396, May 15, 2015 (May 15, 2015), XP040669072.

Lin J et al: "Deep network training based sparsity model for reconstruction", International Society for Magnetic Resonance in Medicine, ISMRM, 2030 Addison Street, 7th Floor, Berkeley, CA 94704 USA, No. 3976, Apr. 7, 2017 (Apr. 7, 2017), XP040691544.

Japanese Office Action issued Oct. 13, 2020 in Japanese Patent Application No. 2019-109545, citing document AT therein, 5 pages.

Kasahara, Y., et al., "MR Image Reconstruction by Stacking using Neural Network", Institute of Electronics Information and Communication Engineers (IEICE), vol. 116, No. 393, Jan. 11, 2017, pp. 2-4 (with English translation).

Japanese Office Action issued on Jun. 23, 2020 in Patent Application No. 2019-109545, 6 pages.

International Search Report issued Feb. 5, 2019 in PCT/JP2018/041193 filed Nov. 6, 2018 (with English translation).

Written Opinion issued Feb. 5, 2019 in PCT/JP2018/041193 filed Nov. 6, 2018.

Y. LeCun, et al., "Deep Learning", Nature, vol. 521, May 2015, pp. 436-444.

J. Schlemper, et al., "A Deep Cascade of Convolutional Neural Networks for MR Image Reconstruction", arXiv:1703.0055v1[cs.CV], 2017, 12 pages.

J. Xie, et al., "Image Denoising and Inpainting with Deep Neural Networks", Neural Information Processing Systems, 2012, pp. 1-9.

Y.S. Han, et al., "Accelerated Projections Reconstruction MR imaging using Deep Residual Learning", The International Society for Magnetic Resonance in Medicine (ISMRM) 25th Annual Meeting & Exhibition, Oral Session 0690, Apr. 2017, 3 pages.

S. Wang, et al., "Accelerating Magnetix Resonance Imaging via Deep Learning", 2016 IEEE, 13$^{th}$ International Symposium on Biomedical Imaging (ISBI), Apr. 2016, pp. 514-517.

H. Takeshima, "Integrating Spatial and temporal Correlations into a Deep Neural Network for Low-delay Reconstruction of Highly Undersampled Radial Dynamic Images", The International Society for Magnetic Resonance in Medicine (ISMRM), 2796, Jun. 2018, pp. 1-3.

\* cited by examiner

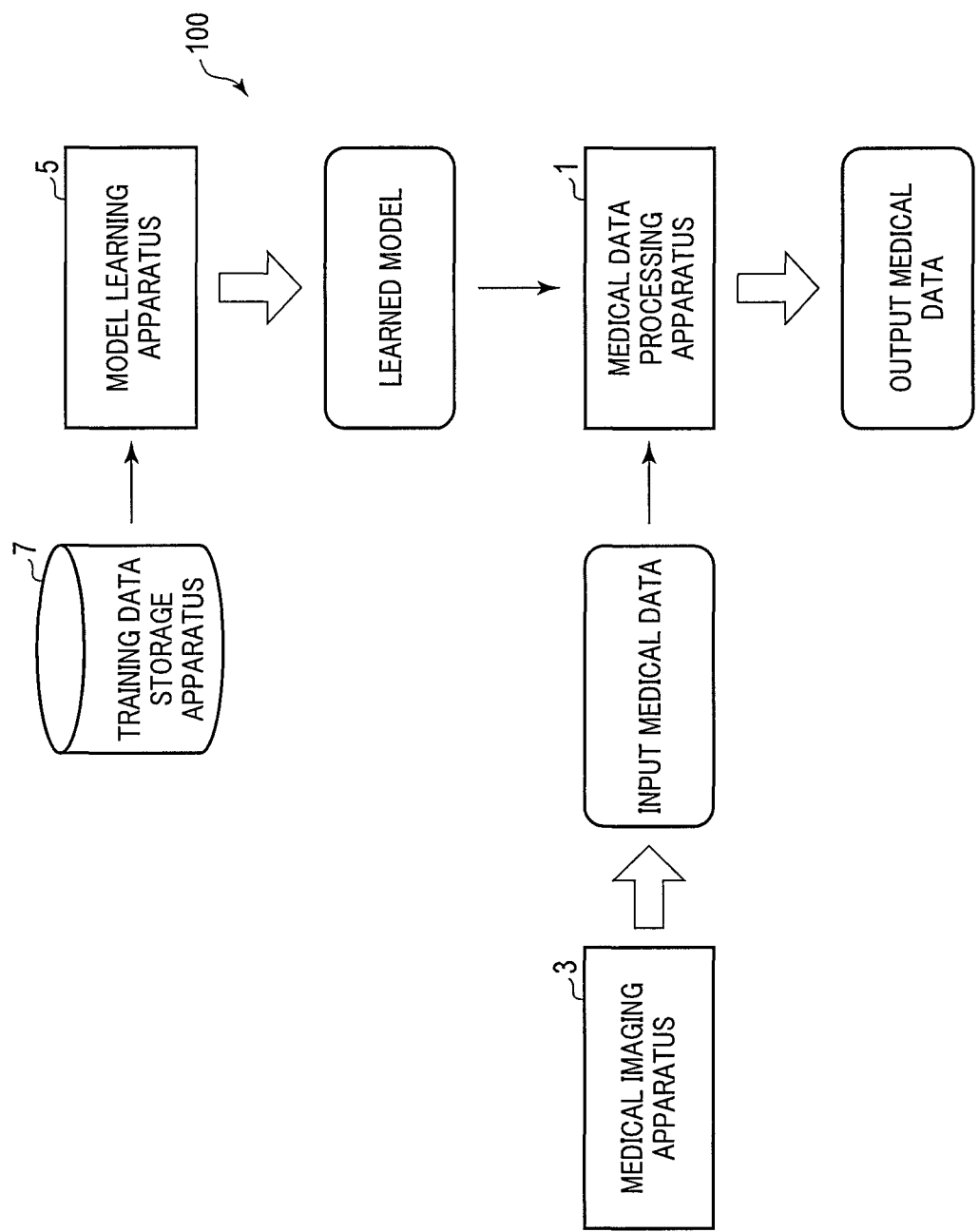
F I G. 1

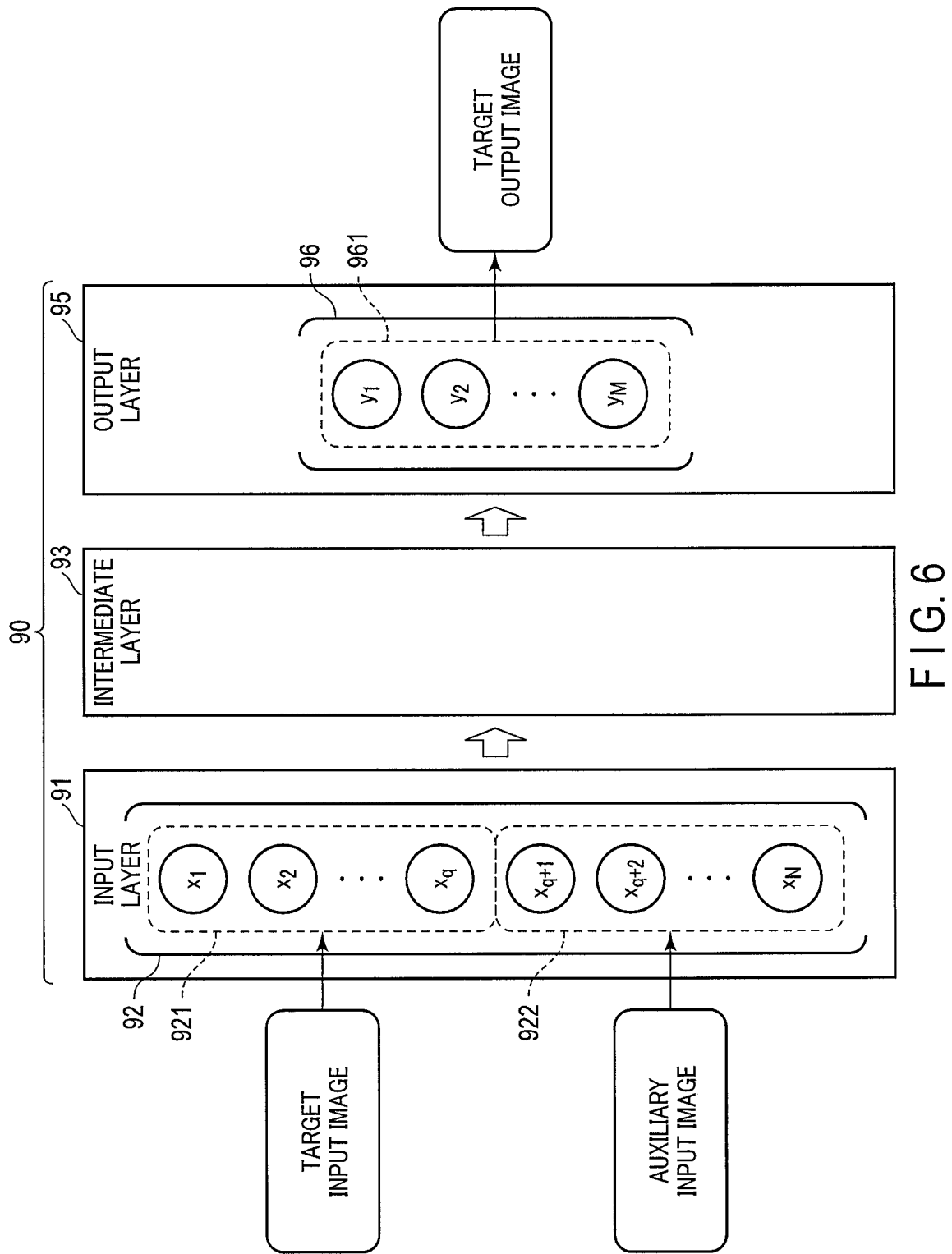
F I G. 6

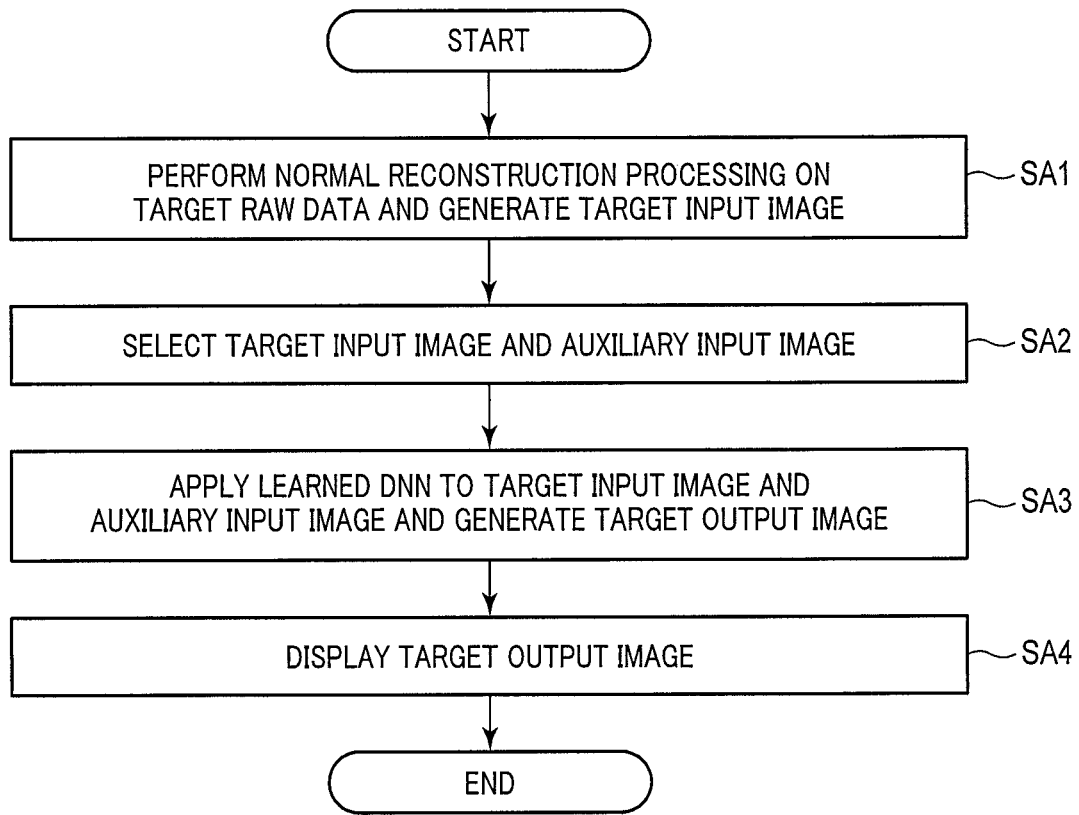
F I G. 7
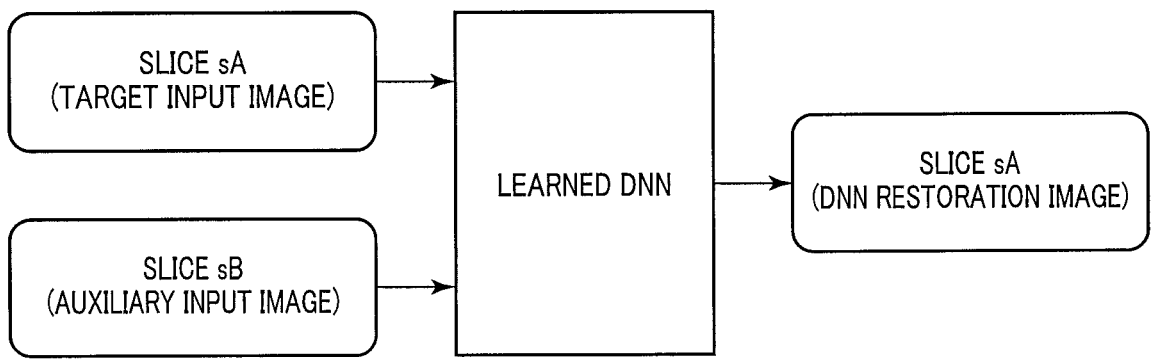
F I G. 8

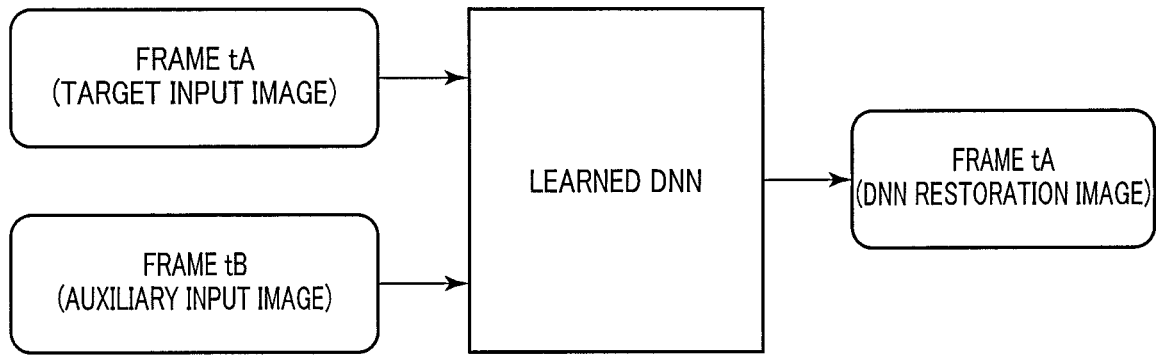
F I G. 9
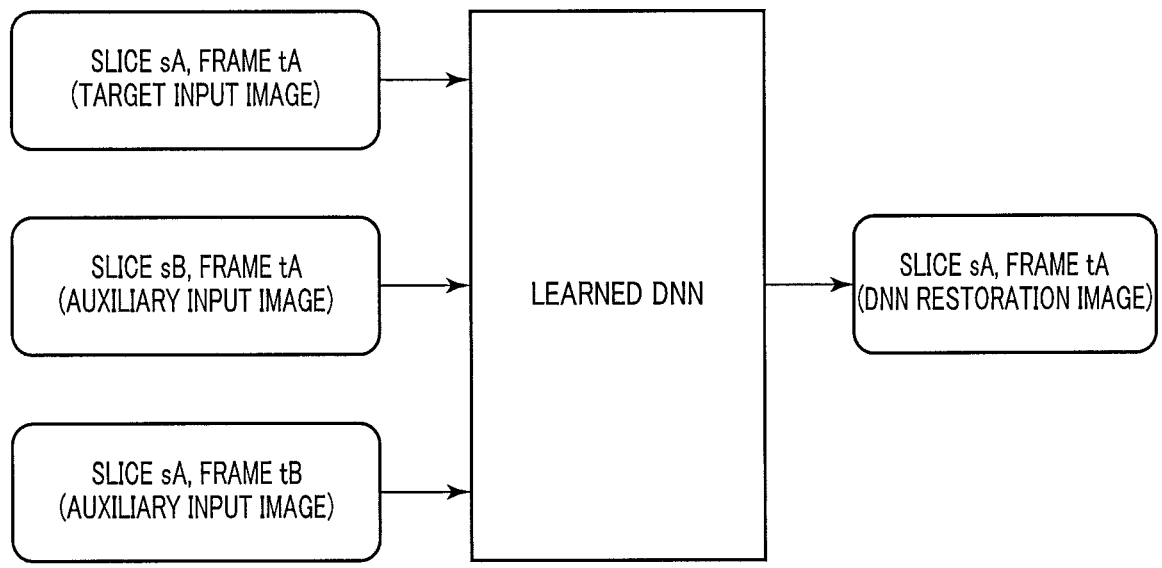
F I G. 10

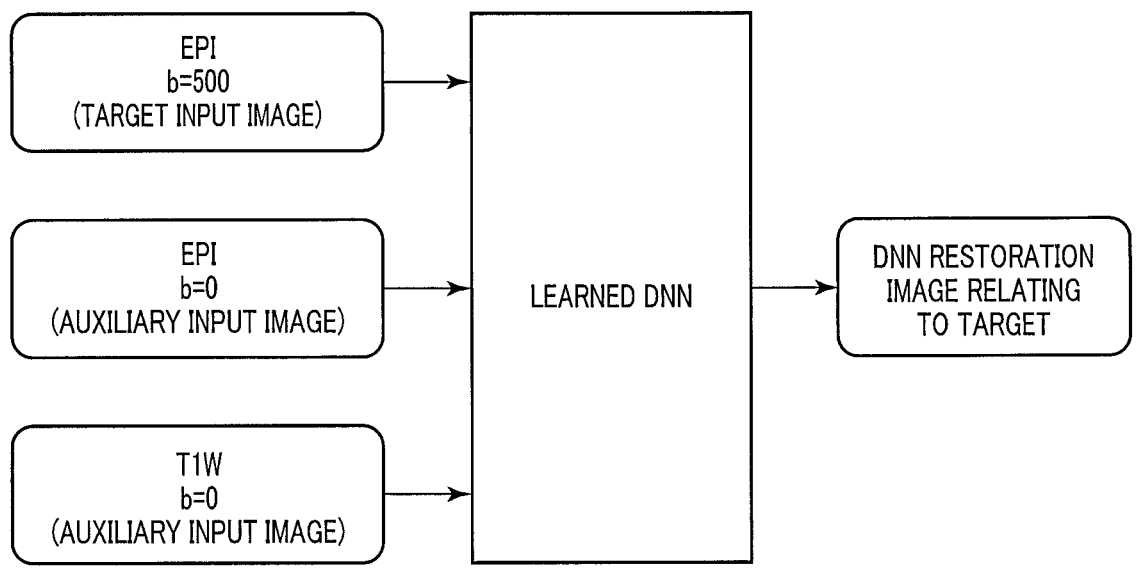
F I G. 13

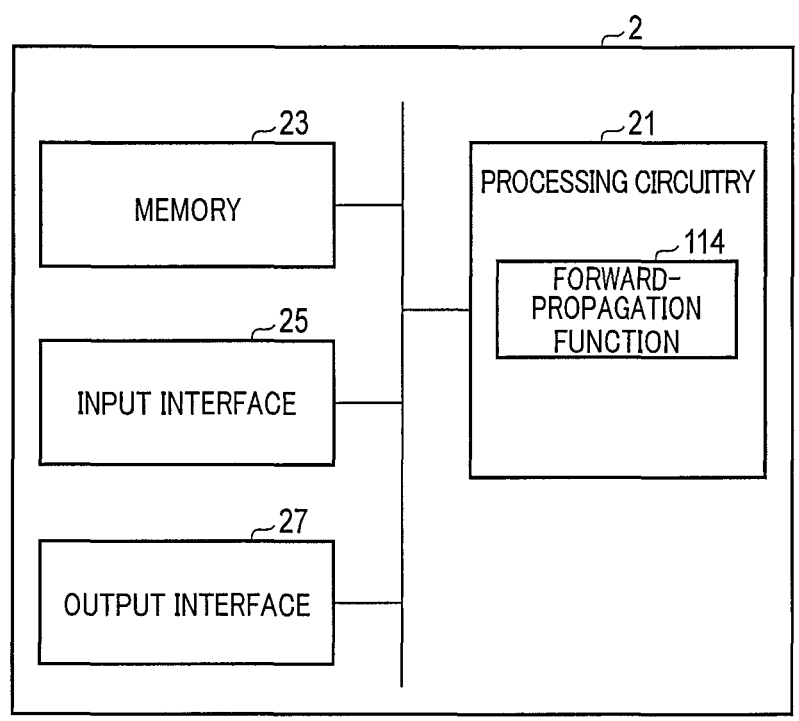
F I G. 14

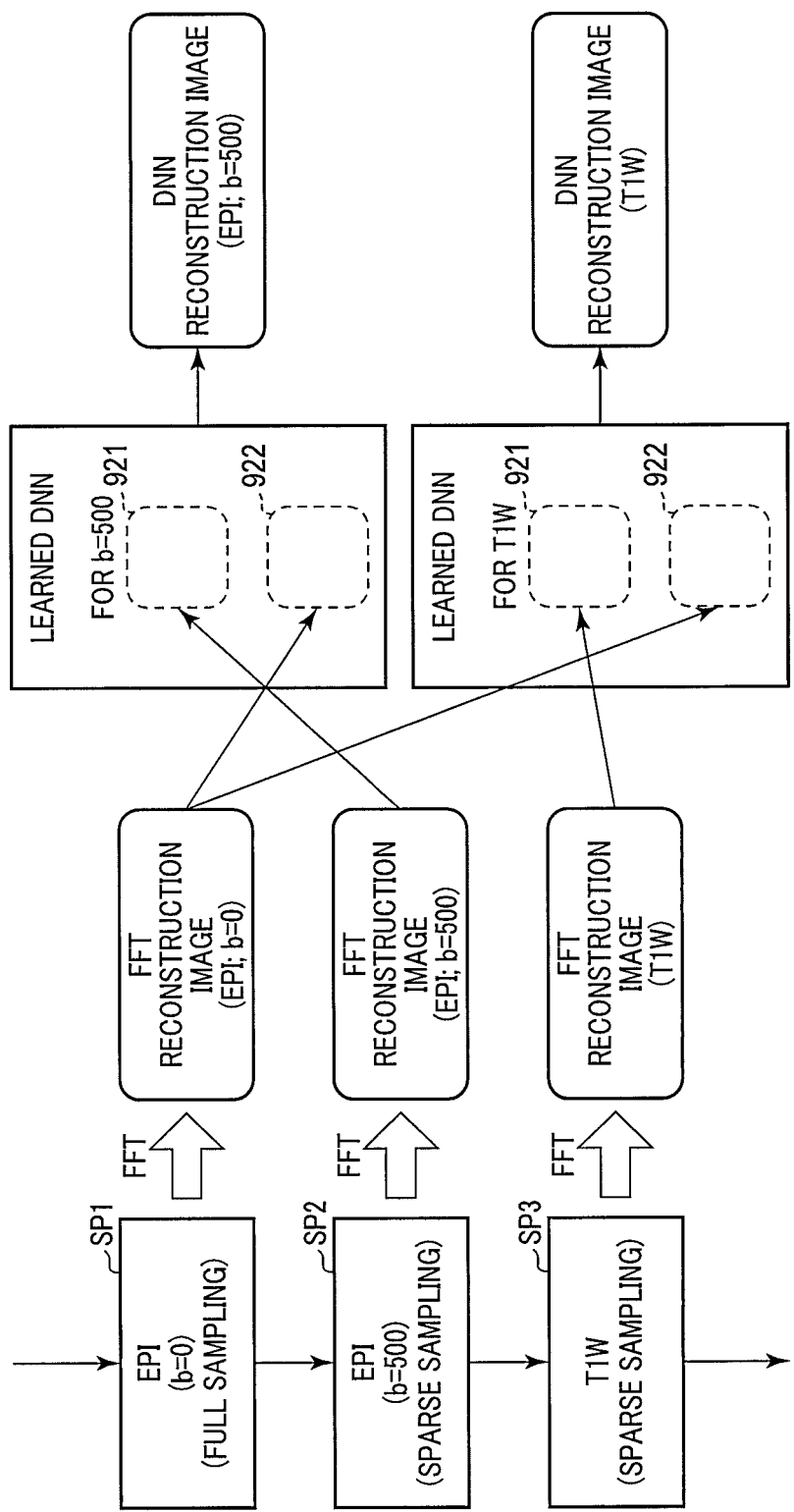
F I G. 18

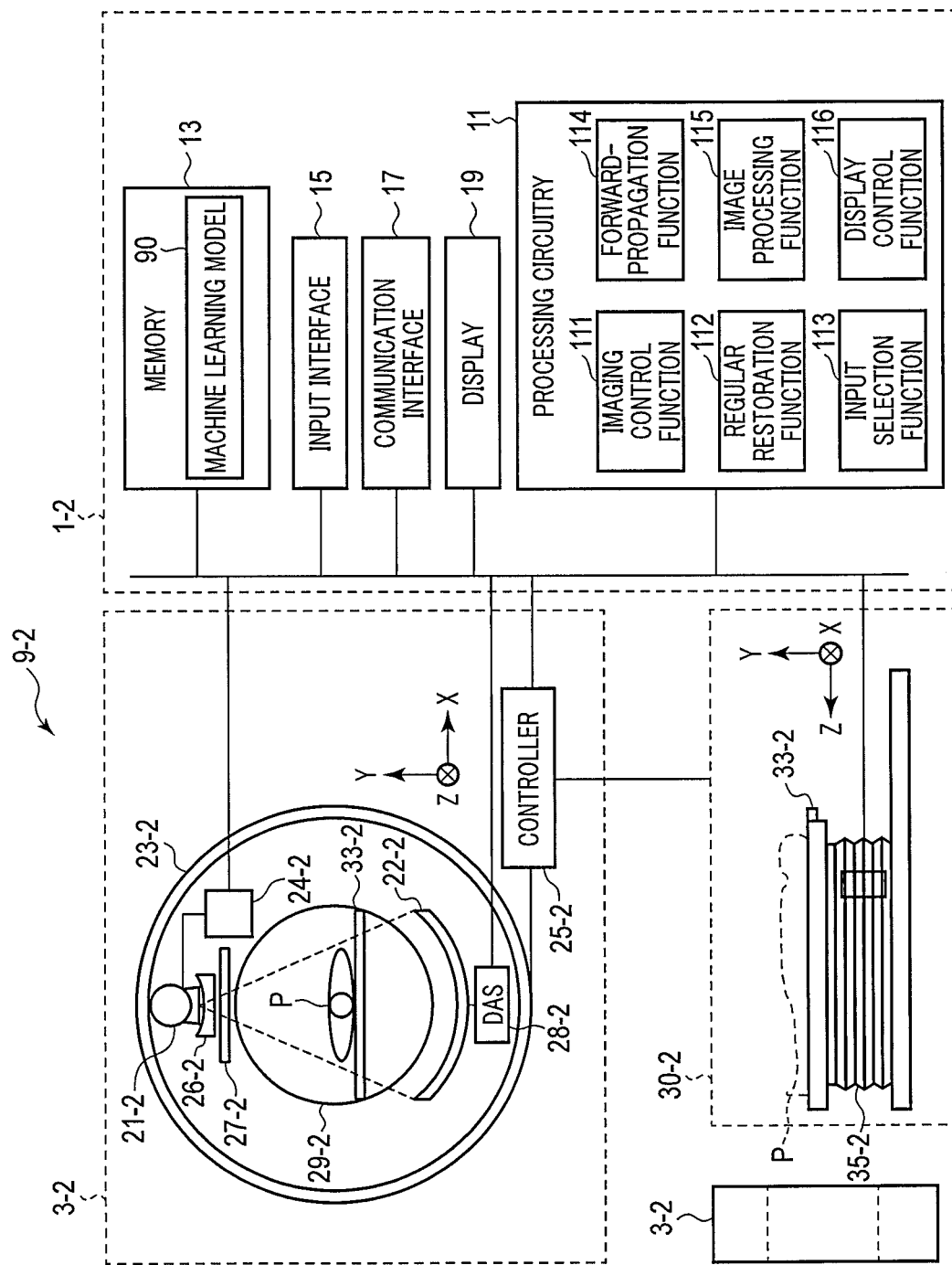
F I G. 19

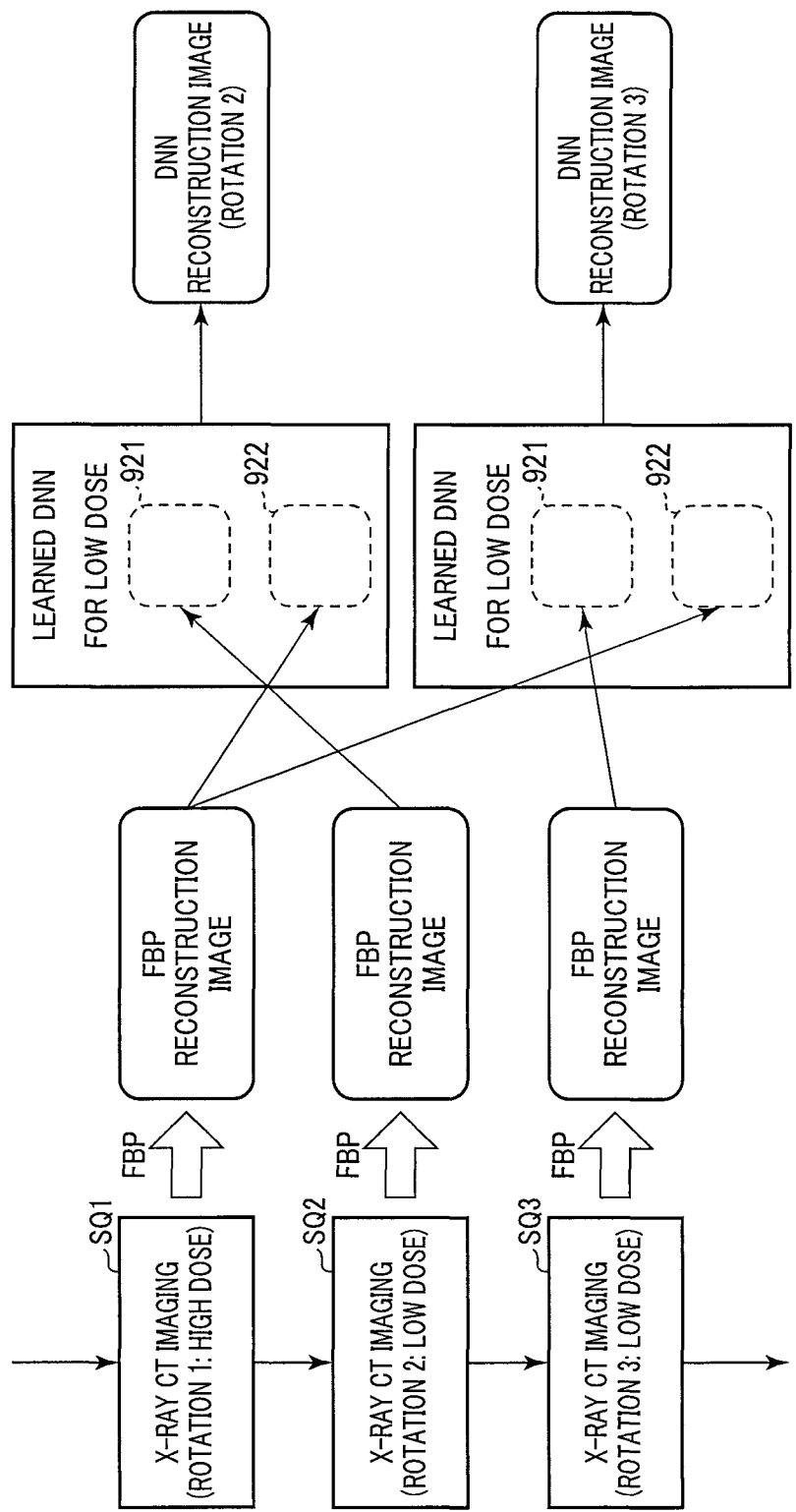
F I G. 20

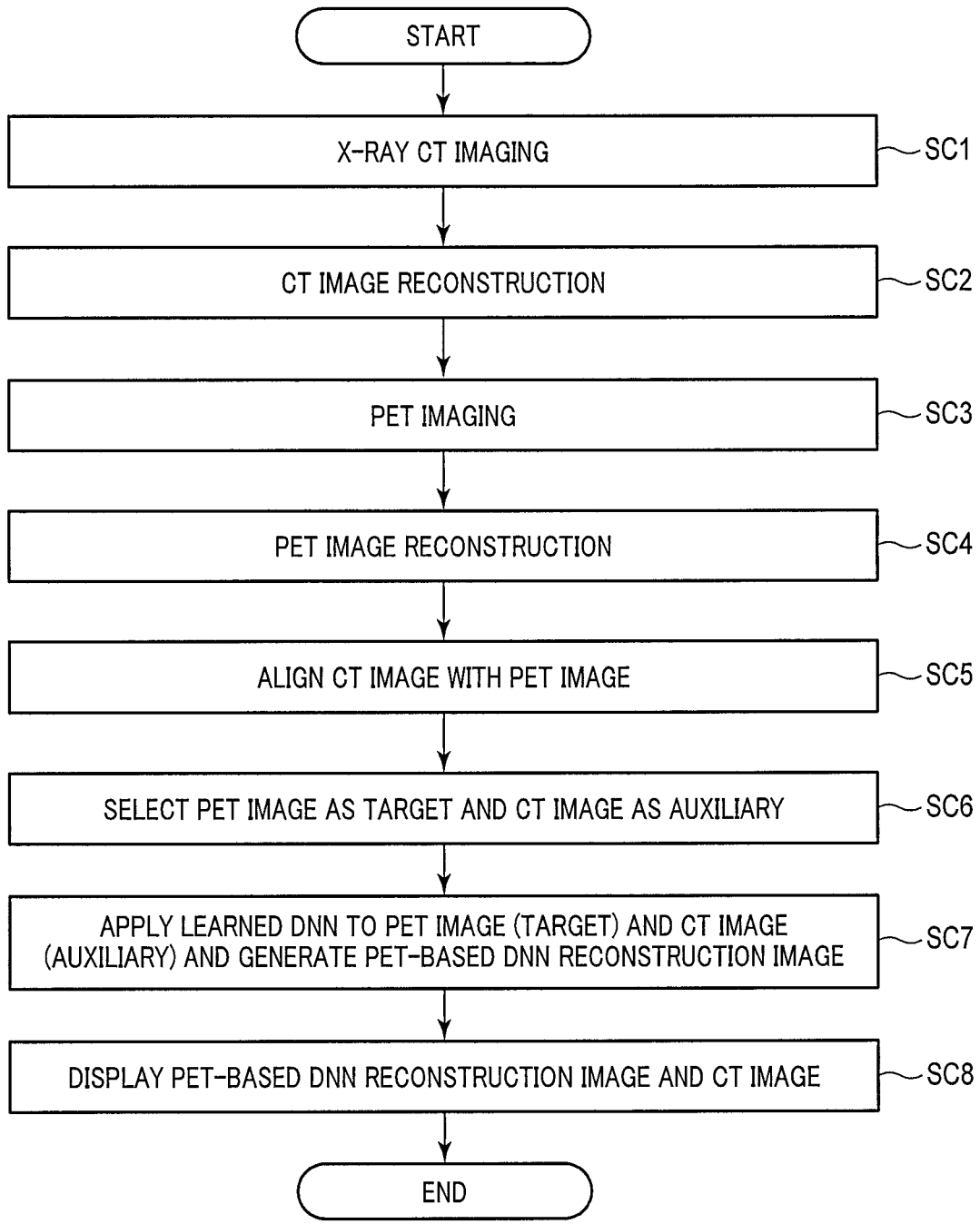
F I G. 22

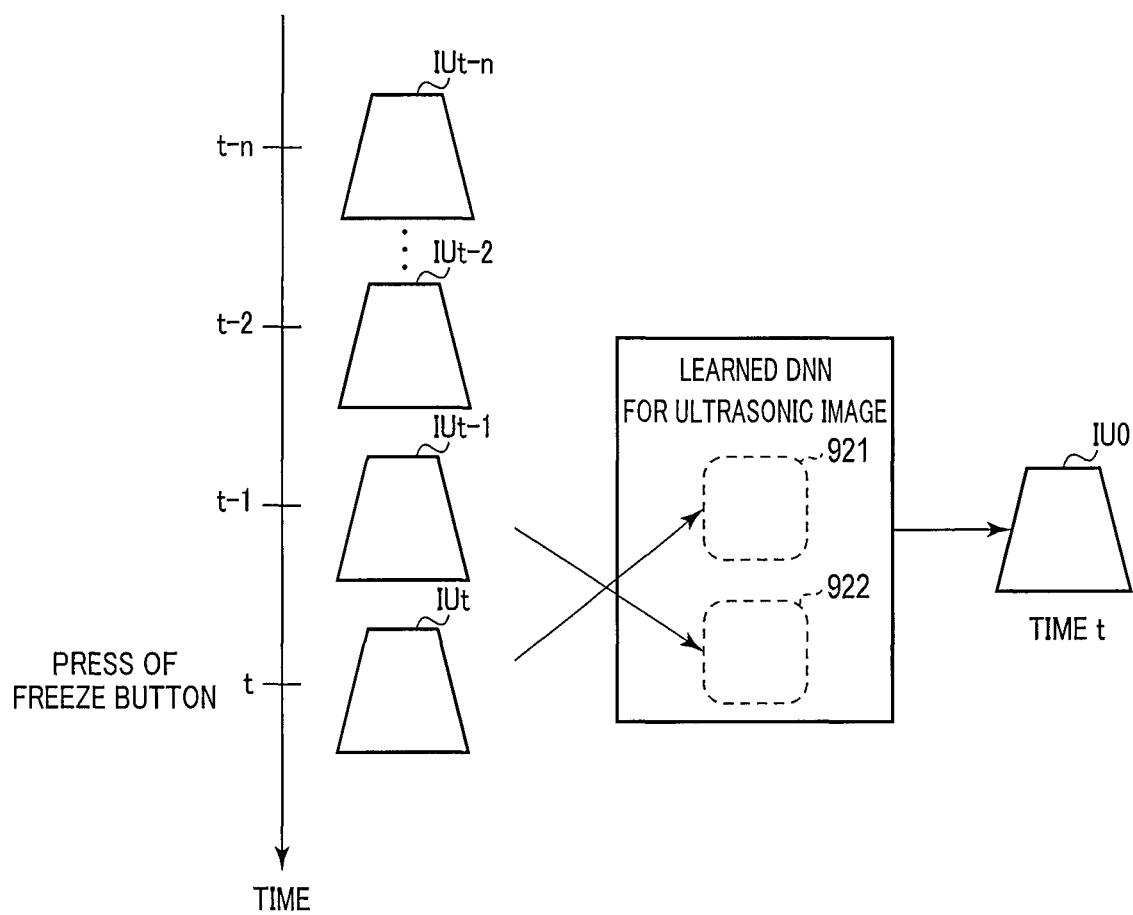
F I G. 25

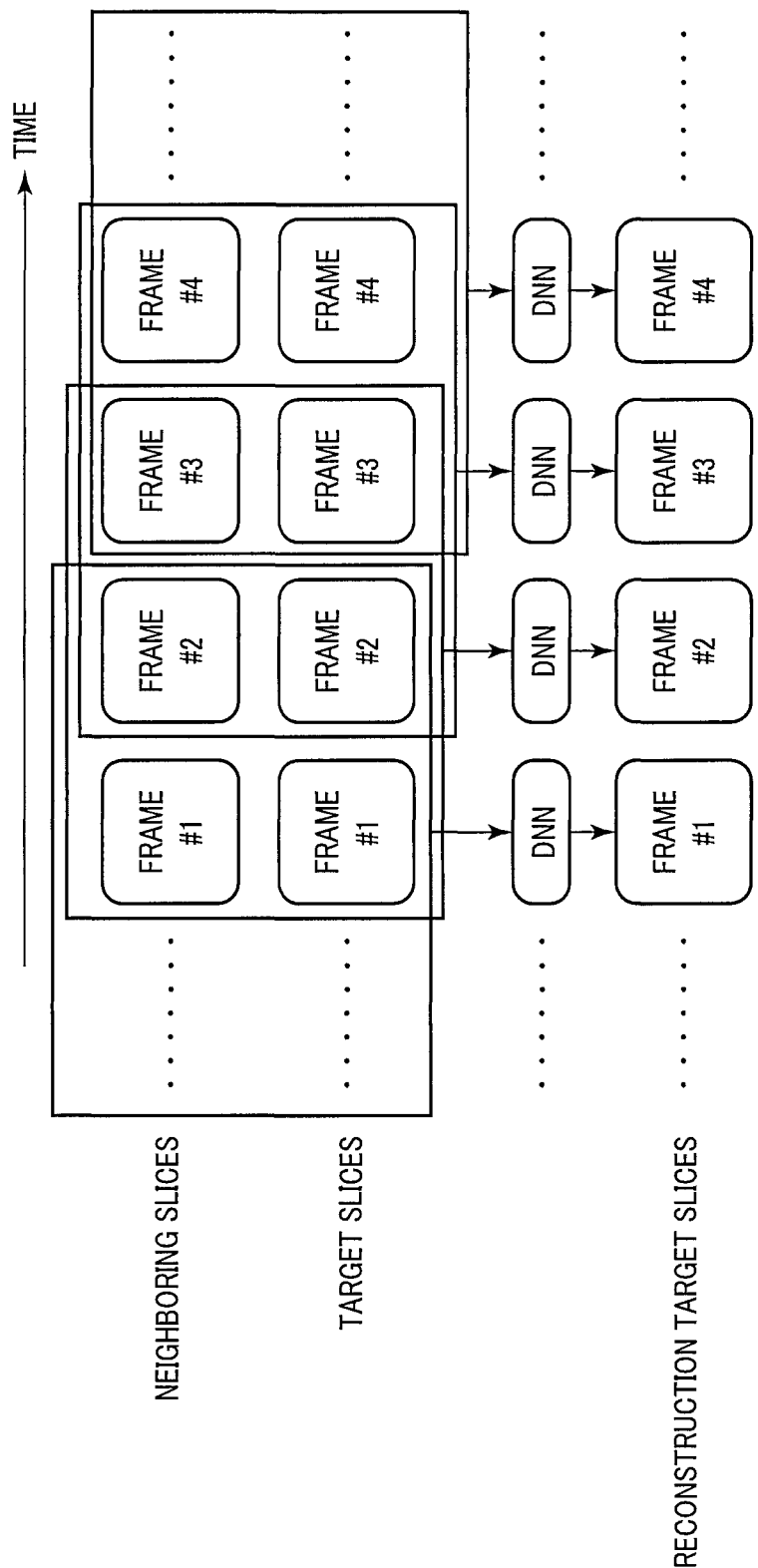
F I G. 26

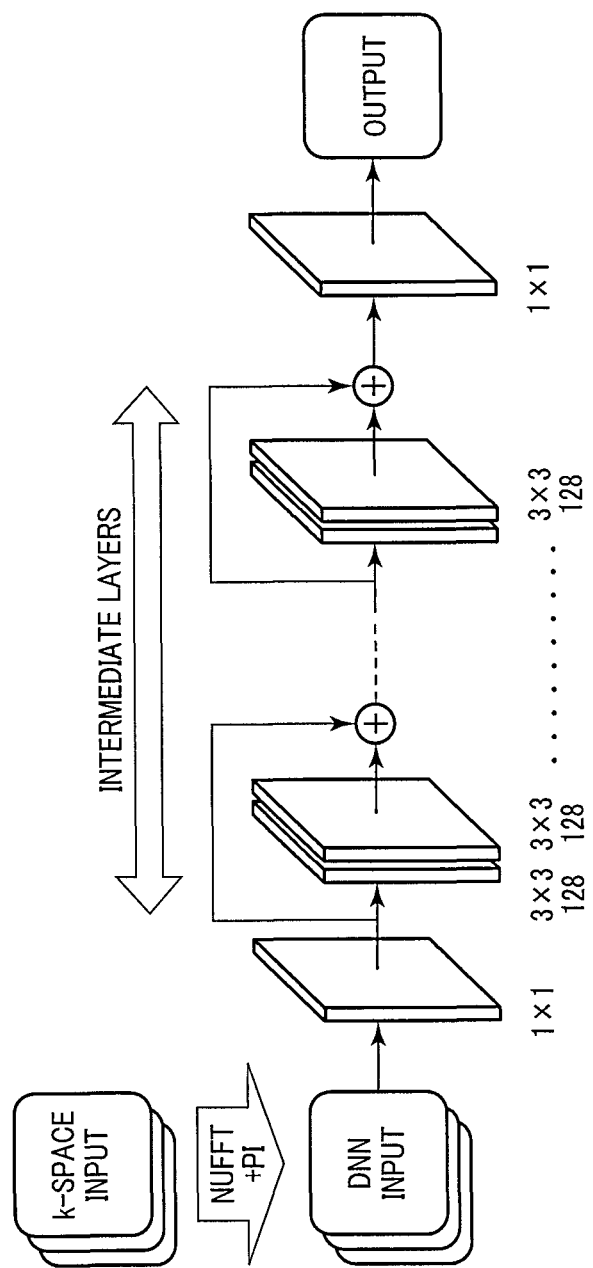
F I G. 27

NUFFT+PI
F I G. 28
M=N=1
F I G. 29

M=5,N=3
F I G. 30
Truth
F I G. 31

NUFFT+PI

M=N=1

M=5,N=3

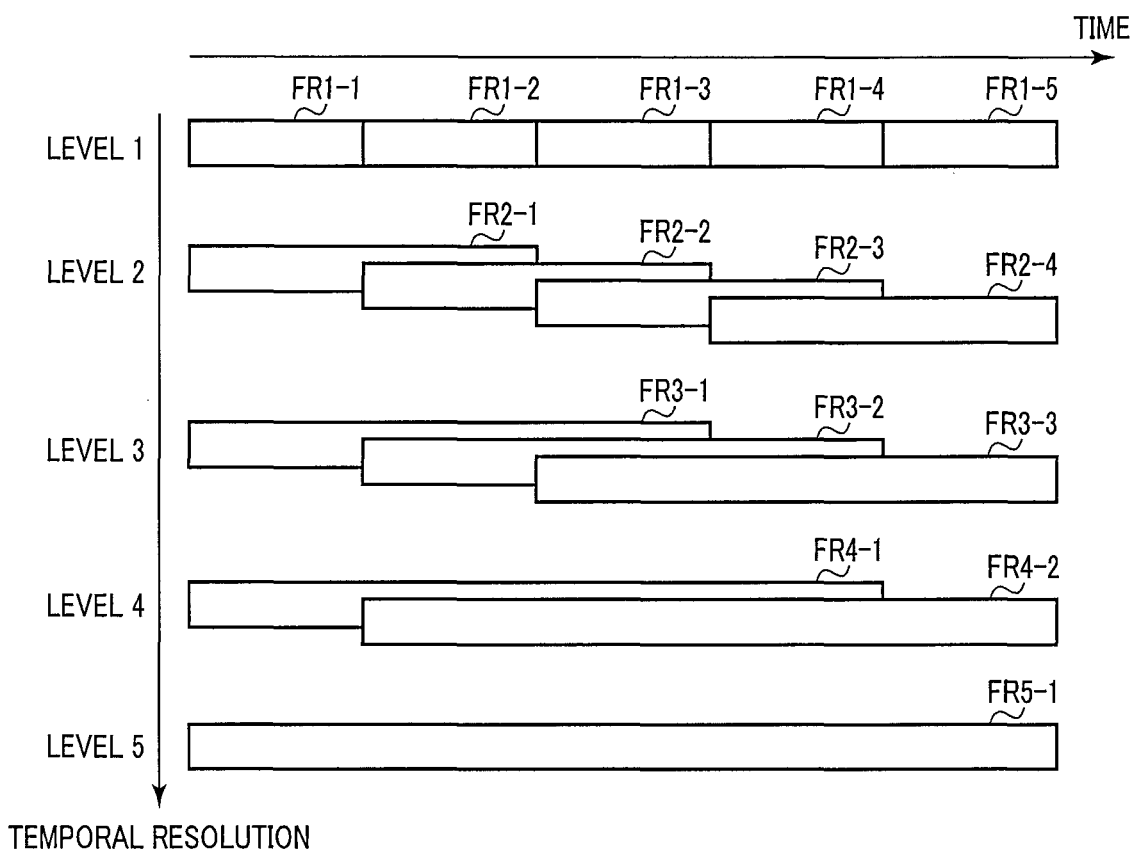
F I G. 35

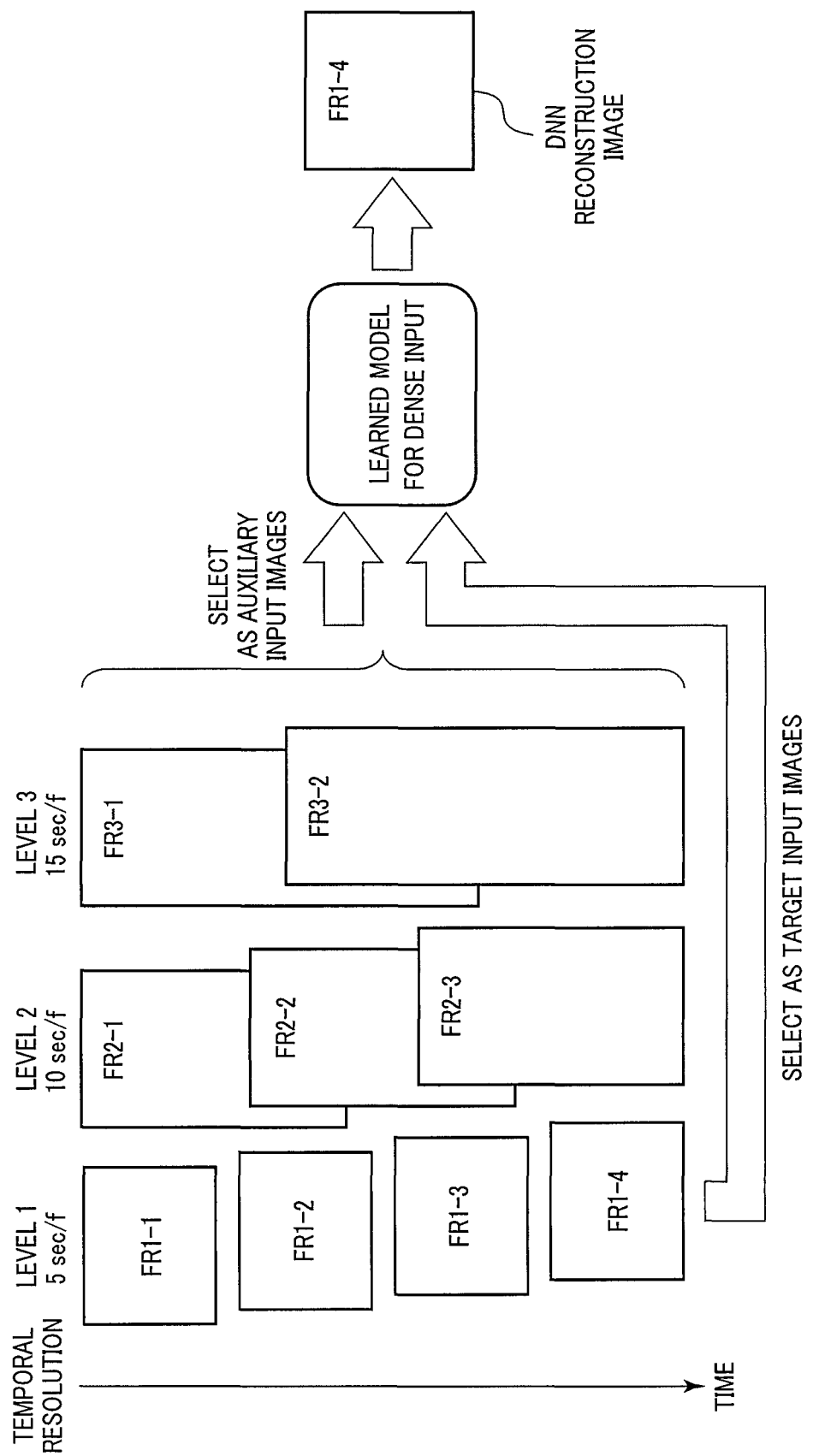
F I G. 36

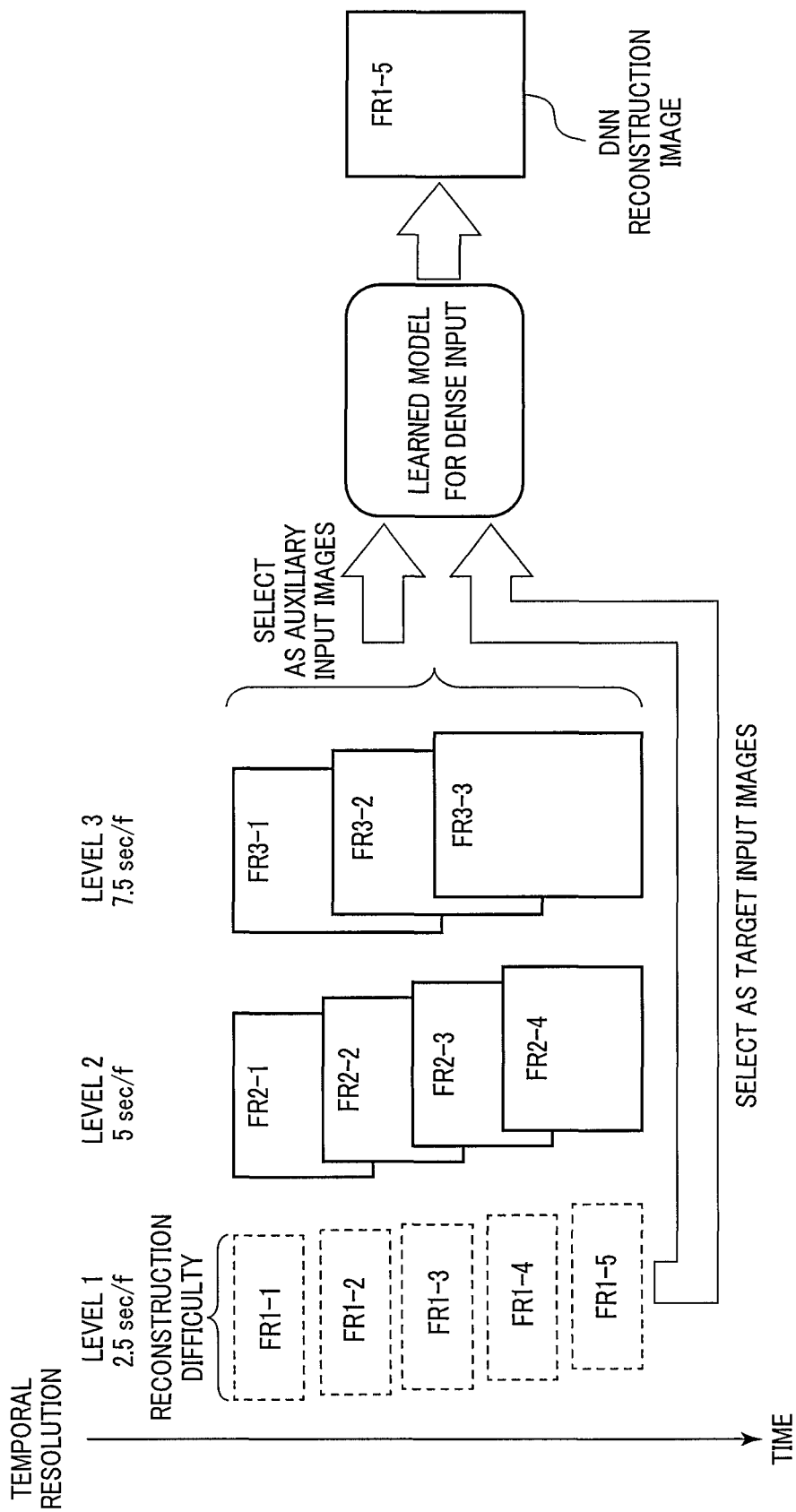
F I G. 37

MEDICAL DATA PROCESSING APPARATUS, MAGNETIC RESONANCE IMAGING APPARATUS, AND LEARNED MODEL GENERATING METHOD

CROSS-REFERENCE TO RELATED APPLICATIONS

This application is a Continuation Application of U.S. application Ser. No. 16/516,938, filed Jul. 19, 2019, which is a Continuation Application of PCT Application No. PCT/JP2018/041193, filed Nov. 6, 2018 and based upon and claims the benefit of priority from the Japanese Patent Application No. 2017-226243, filed Nov. 24, 2017, the entire contents of which are incorporated herein by reference.

FIELD

Embodiments described herein relate generally to a medical data processing apparatus, magnetic resonance imaging apparatus, and learned model generating method.

BACKGROUND

In the field of machine learning that adopts medical data such as medical image data and its raw data, a method that incorporates a deep neural network (DNN) trained with a large amount of training data may be used in order to restore original data from medical data that includes a missing portion. Examples include a method of generating k-space data in which the missing portion is restored by applying a DNN to the undersampled k-space data and acquiring a reconstruction image based on the restored k-space data in magnetic resonance imaging (MRI).

BRIEF DESCRIPTION OF THE DRAWINGS

FIG. 1 is a diagram showing the overview of the configuration and process of a medical data processing system that involves a medical data processing apparatus according to the present embodiment.

FIG. 6 is a diagram showing the detailed structure of a learned model according to the present embodiment.

FIG. 7 is a diagram showing a typical DNN restoration processing flow of the medical data processing apparatus illustrated in FIG. 3.

FIG. 8 is a schematic diagram showing the relationship between the input and the output for the learned deep neural network in the forward-propagation processing according to the present embodiment.

FIG. 9 is a schematic diagram showing another relationship between the input and the output for the learned deep neural network in the forward-propagation processing according to the present embodiment.

FIG. 10 is a schematic diagram showing still another relationship between the input and the output for the learned deep neural network in the forward-propagation processing according to the present embodiment.

FIG. 13 is a schematic diagram showing still another relationship between the input and the output for the learned deep neural network in the forward-propagation processing according to the present embodiment.

FIG. 14 is a diagram showing the structure of another medical data processing apparatus according to the present embodiment.

FIG. 18 is a schematic diagram showing the process of the medical data processing apparatus illustrated in FIG. 17.

FIG. 19 is a diagram showing the configuration of an X-ray computed tomography imaging apparatus according to application example 2.

FIG. 20 is a schematic diagram showing the process of the medical data processing apparatus illustrated in FIG. 19.

FIG. 22 is a schematic diagram showing a typical processing flow of the medical data processing apparatus illustrated in FIG. 21.

FIG. 25 is a schematic diagram showing the process of the medical data processing apparatus illustrated in FIG. 24.

FIG. 26 is a schematic diagram showing the process of the medical data processing apparatus according to implementation example 1.

FIG. 27 is a diagram showing the overview of the DNN according to implementation example 1.

FIG. 28 is a diagram showing a reconstruction image obtained by NUFFT and PI as a result of using simulated radial data (21 spokes per frame).

FIG. 29 is a diagram showing a reconstruction image obtained by a normal reconstruction method (M=N=1) as a result of using the simulated radial data (21 spokes per frame).

FIG. 30 is a diagram showing a reconstruction image obtained by the reconstruction method (M=5 and N=3) according to the implementation example, as a result of using the simulated radial data (21 spokes per frame).

FIG. 31 is a diagram showing a true reconstruction image obtained as a result of using the simulated radial data (21 spokes per frame).

FIG. 35 is a schematic diagram showing dense input executed in implementation example 2.

FIG. 36 is a diagram showing an example of DNN reconstruction using dense input according to implementation example 2.

FIG. 37 is a diagram showing an example of DNN reconfiguration using dense input according to implementation example 3.

DETAILED DESCRIPTION

Figure 2:
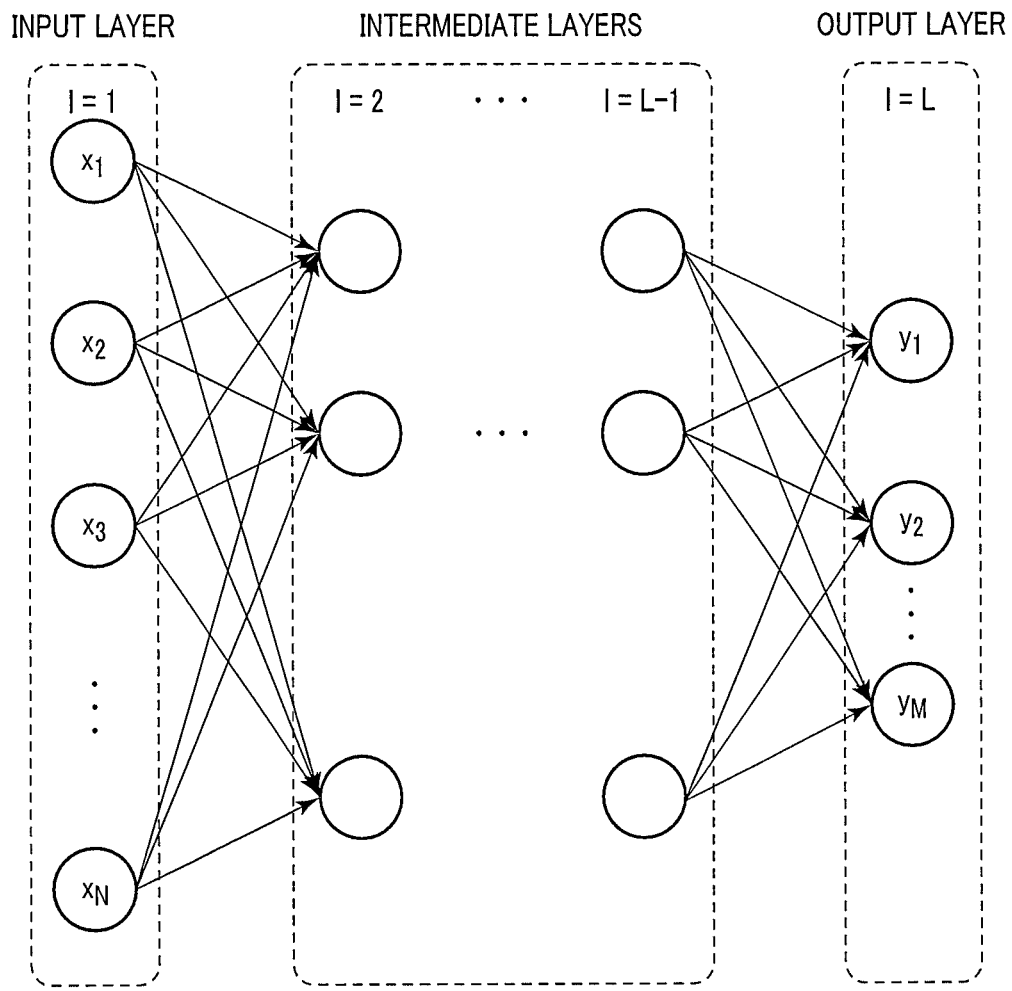
FIG. 2 is a diagram showing the structure of a multilayer network according to the present embodiment.

A medical data processing apparatus according to the present embodiment includes a memory and processing circuitry. The memory is configured to store a learned model including an input layer to which first MR data and second MR data relating to an imaging target the same as the first MR data and an imaging parameter different from the first MR data are inputted, an output layer from which third MR data is output with a missing portion of the first MR data restored, and at least one intermediate layer arranged between the input layer and the output layer, The processing circuitry is configured to generate the third MR data relating to a subject in accordance with the learned model, from the first MR data serving as a process target and relating to the subject and the second MR data relating to the subject and acquired by an imaging parameter different from the first MR data serving as the process target.

A medical data processing apparatus, a magnetic resonance imaging apparatus, and a learned model generation method according to the present embodiment will be described below with reference to the drawings.

FIG. 1 is a diagram showing the overview of the configuration and process of a medical data processing system 100 that involves a medical data processing apparatus 1 according to the present embodiment. As illustrated in FIG. 1, the medical data processing system 100 according to the present embodiment includes a medical data processing apparatus 1, a medical imaging apparatus 3, a model learning apparatus 5 and a training data storage apparatus 7.

The training data storage apparatus 7 stores training data including a plurality of training samples. The training data storage apparatus 7 may be a computer provided with a mass storage device therein. The training data storage apparatus 7 may be a mass storage device connected to a computer in a communicable manner via a cable or a communication network. For such a storage device, a hard disk drive (HDD), a solid state drive (SSD) and an integrated circuitry memory device may be adopted as appropriate.

Based on the training data stored in the training data storage apparatus 7, the model learning apparatus 5 performs machine learning on the machine learning model in line with a model learning program, and generates a trained machine learning model (hereinafter referred to as "learned model"). The model learning apparatus 5 is a computer, such as a workstation, having a processor such as a central processing unit (CPU) and a graphics processing unit (GPU). The model learning apparatus 5 and the training data storage apparatus 7 may be connected to each other in a communicable manner via a cable or a communication network. Alternatively, the training data storage apparatus 7 may be mounted on the model learning apparatus 5. If this is the case, training data is supplied from the training data storage apparatus 7 to the model learning apparatus 5 via a cable, a communication network, or the like. The model learning apparatus 5 and the training data storage apparatus 7 may not be connected to each other in a communicable manner. If this is the case, training data may be supplied from the training data storage apparatus 7 to the model learning apparatus 5 by way of a portable storage medium that stores the training data.

The machine learning model according to the present embodiment is a parameter-added composite function obtained by combining a plurality of functions. Medical data is entered as an input to the machine learning model, and medical data having a missing portion restored is output. A parameter-added composite function is defined by a combination of multiple adjustable functions and parameters. The machine learning model according to the present embodiment may be any parameter-added composite function that satisfies the above requirements as long as it is a multilayer network model (hereinafter referred to as "multilayer network").

The medical imaging apparatus 3 generates process target medical data. The medical data according to the present embodiment conceptually includes raw data acquired by the medical imaging apparatus 3 or some other model imaging apparatus performing medical imaging on the subject, and medical image data generated by performing a restoration process on the raw data. The medical imaging apparatus 3 may be any modality apparatus as long as it is capable of generating medical data. For example, the medical imaging apparatus 3 according to the present embodiment may be a single modality apparatus such as a magnetic resonance imaging apparatus (MRI apparatus), an X-ray computed tomography imaging apparatus (CT apparatus), an X-ray diagnostic apparatus, a positron emission tomography (PET) apparatus, a single photon emission CT (SPECT) apparatus or an ultrasonic diagnostic apparatus. Alternatively, it may be a combined modality apparatus such as PET/CT apparatus, SPECT/CT apparatus, PET/MRI apparatus, or SPECT/MRI apparatus.

The medical data processing apparatus 1 generates output medical data that corresponds to the input medical data that is a process target, which is acquired by the medical imaging apparatus 3, by using a learned model that has been trained in accordance with the model learning program by the model learning apparatus 5. The medical data processing apparatus 1 and the model learning apparatus 5 may be connected to each other in a communicable manner via a cable or a communication network. Alternatively, the medical data processing apparatus 1 and the model learning apparatus 5 maybe mounted on the same computer. If this is the case, the learned model is supplied from the model learning apparatus 5 to the medical data processing apparatus 1 via a cable, a communication network or the like. The medical data processing apparatus 1 and the model learning apparatus 5 may not be connected in a communicable manner. If this is the case, the learned model is supplied from the model learning apparatus 5 to the medical data processing apparatus 1 by way of a portable storage medium or the like that stores the learned model. The learned model may be supplied at any time point between the manufacture of the medical data processing apparatus 1 from the manufacturing of the medical data processing apparatus 1 and installing at a medical facility or the like, or at the time of maintenance. The supplied learned model is stored in the medical data processing apparatus 1. The medical data processing apparatus 1 may be a computer mounted on a medical image diagnostic apparatus having a medical imaging apparatus 3 thereon, or a computer connected to such a medical image diagnostic apparatus via a cable or network in a communicable manner. Alternatively, it may be a computer provided independently from the medical image diagnostic apparatus.

A typical configuration of the multilayer network will be described below. The multilayer network discussed here has a structure in which only adjacent layers arranged in layers are coupled to each other. In such a network, information propagates in one direction, from the input layer side to the output layer side. As indicated in FIG. 2, the multilayer network according to the present embodiment is constituted by L layers, namely, an input layer (l=1), intermediate layers (l=2, 3, ..., L−1) and an output layer (l=L). An example of the multilayer network is described below, but its configuration should not be limited to this description.

When there are the number I of units in the l-th layer, Equation (1-1) denotes the input $u^{(l)}$ to the l-th layer, and Equation (1-2) denotes the output $z^{(l)}$ from the l-th layer, the relationship between the input to the l-th layer and the output from the l-th layer can be expressed by Equation (1-3).

$$u^{(l)} = (u_1, u_2, u_3, \ldots, u_4) \quad (1\text{-}1)$$

$$z^{(l)} = (z_1, z_2, z_3, \ldots, z_4) \quad (1\text{-}2)$$

$$z^{(l)} = f(u^{(l)}) \quad (1\text{-}3)$$

The upper right superscript (l) indicates the layer number. Furthermore, f(u) in Equation (1-3) is an activation function, for which any function can be selected in accordance with the purpose from various functions such as a logistic sigmoid function (logistic function), hyperbolic tangent function, rectified liner unit (ReLU), linear mapping, identity mapping, and max-out function.

When there are the number J of units in the (l+1)-th layer, Equation (2-1) represents the weighting matrix $W^{(l+1)}$ between the l-th layer and the l+1 layer, and Equation (2-2) represents bias $b^{(l+1)}$ in the (l+1)-th layer. Equations (2-3) and (2-4) respectively represent the input $u^{(l+1)}$ to the (l+1)-th layer and the output $z^{(l+1)}$ from the (l+1)-th layer.

$$W^{(l+1)} = \begin{pmatrix} W_{11} & \cdots & W_{1j} \\ \vdots & \ddots & \vdots \\ W_{ji} & \cdots & W_{ji} \end{pmatrix} \quad (2\text{-}1)$$

$$b^{(l+1)} = (b_1, b_2, b_2, \ldots, b_l) \quad (2\text{-}2)$$

$$u^{(l+1)} = W^{(l+1)} z^{(l)} + b^{(l+1)} \quad (2\text{-}3)$$

$$z^{(l+1)} = f(u^{(l+1)}) \quad (2\text{-}4)$$

In the multilayer network according to the present embodiment, the medical data expressed by Equation (3-1) is input to the input layer (l=1). In this input layer, since the input data x directly becomes the output data $z^{(l)}$, the relationship expressed by Equation (3-2) is established.

$$x = (x_1, x_2, x_3, \ldots, x_N) \quad (3\text{-}1)$$

$$z^{(1)} = x \quad (3\text{-}2)$$

Any medical data that is to be input to the input layer will be referred to as "input medical data". For input medical data x, various formats are adoptable in accordance with its purpose. Typical examples are listed below.

(1) Format that determines the input medical data x as one image data item, and defines each of its components $x_p$ (p=1, 2, ..., N) as a value (pixel value or voxel value) of the position in the image data item.

(2) Format that determines the input medical data x as M items of image data (e.g., multiple items of image data with different imaging conditions), determines each component $x_p$ where 1≤p≤q as the first image data item, where q+1≤p≤r as the second image data item, where r+1≤p≤s as the third image data, ..., and assigns the area of the input unit to each image data item in the input layer.

(3) Format that determines the input medical data x as M items of image data and defines each component $x_p$ as a vector in which values of positions (pixel values or voxel values) in a single image data item are vertically provided.

(4) Format that adopts any of (1) to (3), with the input medical data x being as the raw data such as k-space data and projection data.

(5) Format that adopts any of (1) to (3), with the input medical data x being as image data or raw data subjected to a convolutional process.

For the intermediate layers (l=2, 3, ..., L−1) subsequent to the input layer, outputs $z^{(2)}, \ldots z^{(L-1)}$ of the layers can be calculated by sequentially executing the calculations of Equations (2-3) and (2-4).

The output $z^{(L)}$ of the output layer (L-th layer) is expressed by Equation (4-1) below. The multilayer network according to the present embodiment is a forward-propagation network in which the image data x that is input to the input layer propagates from the input layer side to the output layer side with only adjacent layers being coupled to each other. Such a forward-propagation network can be expressed as a composite function as in Equation (4-2).

$$z^{(L)}: y = z^{(L)} \quad (4\text{-}1)$$

$$\begin{aligned} y(x) &= f(u^{(L)}) \\ &= f(W^{(L)} z^{(L-1)} + b^{(L)}) \\ &= f(W^{(L)} f(W^{(L-1)} z^{(L-2)} + b^{(L-1)}) + b^{(L)}) \\ &= f(W^{(L)} f(W^{(L-1)} f(\ldots \ldots f(W^{(l)} z^{(l-1)} + b^{(l)}) \ldots \ldots )) + b^{(L)}) \end{aligned} \quad (4\text{-}2)$$

The composite function defined by Equation (4-2) is defined as a combination of a linear correlation between the layers using the weighting matrix $W^{(l+1)}$, a nonlinear correlation (or linear correlation) using an activation function $f(u^{(l+1)})$ of the layers, and bias $b^{(l+1)}$, based on Equations (2-3) and (2-4). In particular, the weighting matrix $W^{(l+1)}$ and bias $b^{(l+1)}$ are referred to as network parameters p of the network. The composite function defined by Equation (4-2) changes its form as a function in accordance with the parameters p that are selected. By selecting suitable parameters p of Equation (4-2), the multilayer network according to the present embodiment can be defined as a function that allows the output layer to output a desired result y.

To select suitable parameters p, training is executed using training data and an error function. Here, the training data represents the set D (n=1, ..., S) of training samples ($x_n$, $d_n$) expressed as in Equation (5-1), where $d_n$ is a desired output (true output) corresponding to the input $x_n$.

$$(x_n, d_n) \quad (5\text{-}1)$$

$$D = \{(x_1, d_1), \ldots, (x_S, d_S)\} \quad (5\text{-}2)$$

The error function represents the proximity of the output from the multilayer network to which $x_n$ is input, to the training data $d_n$. Typical examples of the error functions include a squared error function, a maximum likelihood estimation function, and a cross entropy function. Which function to adopt as the error function depends on the problem handled by the multilayer network (e.g., regression problem, binary problem, multi-class classification problem).

The error function is expressed as $E(p)$, and the error function obtained using a single training sample $(x_n, d_n)$ is expressed as $E_n(p)$. The current parameter $p^{(t)}$ is updated to a new parameter $p^{(t+1)}$ by Equation (6-1) that incorporates the gradient vector of the error function $E(p)$ when adopting the gradient descent method, or by Equation (6-3) that incorporates the gradient vector of the error function $E_n(p)$ when adopting the stochastic gradient descent method.

$$p^{(t+1)} = p^{(t)} - \varepsilon \nabla E(p^{(t)}) \tag{6-1}$$

$$\nabla E(p^{(t)}) = \frac{\partial E}{\partial p^{(t)}} = \left[ \frac{\partial E}{\partial p_1^{(t)}}, \ldots \ldots \ldots \frac{\partial E}{\partial p_M^{(t)}} \right] \tag{6-2}$$

$$p^{(t+1)} = p^{(t)} - \varepsilon \nabla E_n(p^{(t)}) \tag{6-3}$$

$$\nabla E_n(p^{(t)}) = \frac{\partial E_n}{\partial p^{(t)}} = \left[ \frac{\partial E_n}{\partial p_L^{(t)}}, \ldots \ldots \ldots \frac{\partial E_n}{\partial p_M^{(t)}} \right] \tag{6-4}$$

Here, $\varepsilon$ is a training coefficient that determines the magnitude of the update amount of parameter p.

The current p is slightly moved in the negative slope direction according to Equation (6-1) or (6-3), and this moving operation is repeated. In this manner, the parameter p that can minimize the error function $E(p)$ can be determined.

To calculate Equation (6-1) or Equation (6-3), the gradient vector of $E(p)$ expressed by Equation (6-2) or the gradient vector of $E_n(p)$ expressed by Equation (6-4) needs to be calculated. If, for example, a squared error function is adopted as the error function, the error function shown in Equation (7-1) needs to be differentiated with respect to the weighting factor of each layer and the bias of each unit.

$$E(\vec{p}) = \frac{1}{2} \sum_{n=1}^{N} \| d_n - y(x_n; p) \|^2 \tag{7-1}$$

With the final output y being a composite function given by Equation (4-2), however, the calculation of the gradient vector of $E(p)$ or $E_n(p)$ becomes complicated, requiring a vast amount of calculation.

Such a problem in gradient calculation can be solved by an error backpropagation method. For example, the derivative of the error function with respect to the weight $w_{ji}^{(l)}$ connecting the i-th unit of the (l-1)-th layer to the j-th unit of the l-th layer can be given by Equation (8-1).

$$\frac{\partial E_n}{\partial w_{ji}^{(l)}} = \frac{\partial E_n}{\partial u_j^{(l)}} \frac{\partial u_j^{(l)}}{\partial w_{ji}^{(l)}} \tag{8-1}$$

The amount of change in $E_n$ caused by the input $u_j^{(l)}$ to the j-th unit of the l-th layer is caused only by the input $u_k^{(l+1)}$ to each unit k of the (l+1)-th layer, which is changed by the output $z_j^{(l)}$ from the j-th unit. Thus, the first term on the right side of Equation (8-1) can be given below by Equation (9-1) using the chain rule of differentiation.

$$\frac{\partial E_n}{\partial u_l^{(l)}} = \sum_k \frac{\partial E_n}{\partial u_k^{(l+1)}} \frac{\partial u_k^{(l+1)}}{\partial u_l^{(l)}} \tag{9-1}$$

Letting the left-hand side of Equation (9-1) be $\delta_j^{(l)}$, Equation (9-1) can be rewritten into Equation (10-3), using the relations given by Equations (10-1) and (10-2).

$$u_k^{(l+1)} = \sum_j w_{kj}^{(l+1)} z_j^{(l)} = \sum_j w_{kj}^{(l+1)} f(u_j^{(l)}) \tag{10-1}$$

$$\frac{\partial u_k^{(l+1)}}{\partial u_j^{(l)}} = w_{kj}^{(l+1)} \frac{\partial f(u_j^{(l)})}{\partial u_j^{(l)}} \tag{10-2}$$

$$\delta_l^{(l)} = \sum_k \delta_k^{l+1} \left( w_{kj}^{(l+1)} \frac{\partial f(u_j^{(l)})}{\partial u_j^{(l)}} \right) \tag{10-3}$$

In Equation (10-3), $\delta_j^{(l)}$ on the left side can be calculated from $\delta_k^{(l+1)}$ (k=1, 2, ...). That is, $\delta_j^{(l)}$ for the l-th layer can be calculated once $\delta_k^{(l+1)}$ is given for the k-th unit of the (l+1)-th layer, which is one layer higher on the output layer side. Similarly, $\delta_k^{(l+1)}$ for the k-th unit of the (l+1)-th layer can be calculated, once $\delta_k^{(l+2)}$ is given for the k-th unit of the (l+2)-th layer, which is a layer higher still on the output layer side. This operation is repeated to reach the uppermost output layer.

With $\delta_k^{(L)}$ first acquired for the k-th unit of the output layer, which is the L-th layer, the calculation of $\delta_k^{(l+1)}$ can be calculated for any layer by repeating the calculation toward the lower side (i.e., to the input layer side), using Equation (10-3) (back propagation).

For the second term on the right side of Equation (8-1), Equation (11-2) can be obtained using Equation (11-1) in which the components are expressed with respect to the l-th layer in Equation (2-3).

$$u_j^{(l)} = \sum_i w_{ji}^{(l)} z_j^{(l-1)} \tag{11-1}$$

$$\frac{\partial u_j^{(l)}}{\partial w_{ji}^{(l)}} = z_j^{(l-1)} \tag{11-2}$$

The derivative of the error function therefore can be expressed as in Equation (12-1) below, with respect to the weight $w_{ji}^{(l)}$ connecting the i-th unit of the (l-1)-th layer to the j-th unit of the l-th layer, using Equation (8-1), $\delta_j^{(l)}$ given by Equation (10-3), and Equation (11-2).

$$\frac{\partial E_n}{\partial w_{ji}^{(l)}} = \delta_j^{(l)} z_j^{(l-1)} \tag{12-1}$$

It is understood from Equation (12-1) that the derivative of the error function for the weight $w_{ji}^{(l)}$ that connects the i-th unit of the (l-1)-th layer and the j-th unit of the l-th layer is given by the product of $\delta_j^{(l)}$ for the j-th unit and the output $z_i^{(l-1)}$ from the i-th unit. The calculation for $\delta_j^{(l)}$ can be executed by back propagation using Equation (10-3) as described above, and the initial value of the back propagation, or in other words $\delta_j^{(L)}$ for the L-th layer that is the output layer, can be calculated from Equation (13-1) below.

$$\delta_j^{(L)} = \frac{\partial E_n}{\partial u_j^{(L)}} \qquad (13\text{-}1)$$

With the above procedure, training can be achieved using a training sample $(x_n, d_n)$ for the multilayer network according to the present embodiment. The above procedure is repeated in parallel for the training samples $(x_n, d_n)$, for the gradient vector with respect to the total sum $E=\Sigma_n E_n$ of errors for a plurality of training samples, and the gradient vector can be acquired by calculating the sum from Equation (14-1).

$$\frac{\partial E}{\partial w_{ji}^{(l)}} = \sum_k \frac{\partial E_n}{\partial w_j^{(l)}} \qquad (14\text{-}1)$$

The medical data processing system 100 using the multilayer network according to the present embodiment will be described in detail below. In the following description, the medical data processing apparatus 1 is coupled to the medical imaging apparatus 3, and incorporated, together with the medical imaging apparatus 3, into a medical image diagnostic apparatus.

Figure 3:
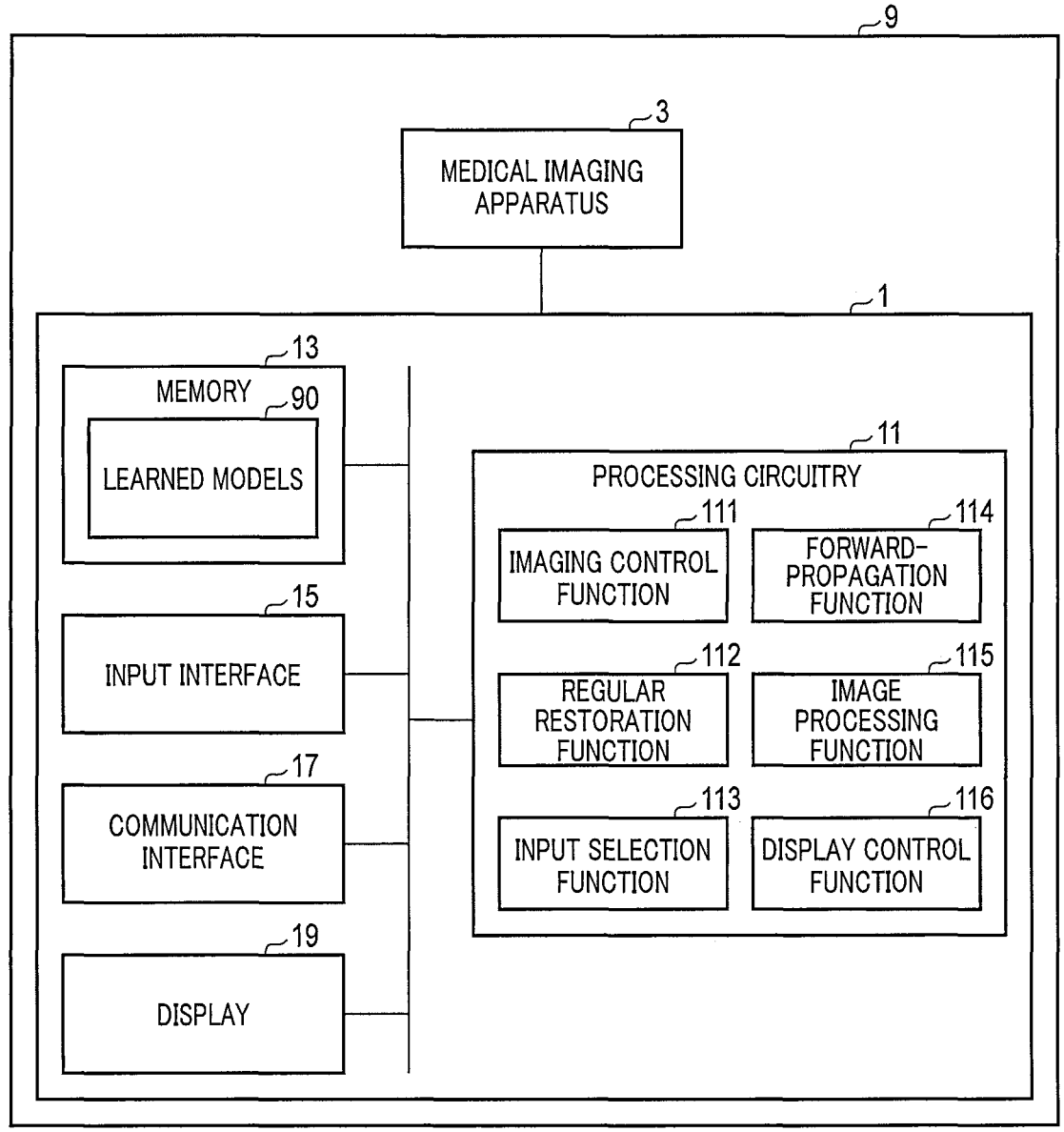
FIG. 3 is a diagram showing the configuration of a medical image diagnostic apparatus according to the present embodiment.

FIG. 3 is a diagram showing the configuration of a medical image diagnostic apparatus 9 according to the present embodiment. As shown in FIG. 3, the medical image diagnostic apparatus 9 includes a medical data processing apparatus 1 and a medical imaging apparatus 3. In one example, the medical imaging apparatus 3 corresponds to a gantry, and the medical data processing apparatus 1 corresponds to a console connected to the gantry. The medical data processing apparatus 1, however, may be arranged in the gantry of the medical image diagnostic apparatus 9, or may be realized by a component that is different from the console or gantry of the medical image diagnostic apparatus 9. The different component, if the medical image diagnostic apparatus 9 is a magnetic resonance imaging apparatus, may be a computer or a dedicated computing machine other than the console, which is installed in a machine room.

The medical imaging apparatus 3 provides the subject with medical imaging of the imaging principles corresponding to the modality type of the medical imaging apparatus 3, and acquires raw data for the subject. The acquired raw data is transferred to the medical data processing apparatus 1. The raw data may be k-space data for the medical imaging apparatus 3 being a magnetic resonance imaging apparatus, and projection data or sinogram data for an X-ray computed tomography imaging apparatus. The raw data may be echo data for an ultrasonic diagnostic apparatus, coincidence data or sinogram data for a PET apparatus, and projection data or sinogram data for a SPECT apparatus. When the medical imaging apparatus 3 is an X-ray diagnostic apparatus, the raw data is X-ray image data.

When the medical imaging apparatus 3 is the gantry of the magnetic resonance imaging apparatus, this gantry repeats application of the gradient magnetic field by way of a gradient magnetic field coil and application of RF pulses by way of a transmission coil under the application of the static magnetic field by way of a static magnetic field magnet. An MR signal from the subject is released in response to the application of the RF pulse. The released MR signal is received by way of a reception coil. The received MR signal is subjected to signal processing such as A/D conversion by the reception circuitry. The A/D converted MR signal is referred to as k-space data. The k-space data is transferred as raw data to the medical data processing apparatus 1.

When the medical imaging apparatus 3 is the gantry of the X-ray computed tomography imaging apparatus, the gantry applies X-rays to the subject from the X-ray tube while rotating the X-ray tube and the X-ray detector around the subject, and detects by an X-ray detector the X-rays passed through the subject. In the X-ray detector, an electric signal having a crest value corresponding to the detected X-ray dose is generated. This electric signal is subjected to signal processing such as A/D conversion by a data acquisition circuitry. The A/D converted electrical signal is referred to as projection data or sinogram data. The projection data or sinogram data is transferred as raw data to the medical data processing apparatus 1.

When the medical imaging apparatus 3 is an ultrasonic probe of the ultrasonic diagnostic apparatus, the ultrasonic probe transmits ultrasonic beams from a plurality of ultrasonic vibrators into the subject body, and receives the ultrasonic waves reflected from the subject body by way of the ultrasonic vibrators. The ultrasonic vibrators generate an electric signal having a crest value corresponding to the sound pressure of the received ultrasonic waves. The electric signal is subjected to the A/D conversion by the A/D converter provided in the ultrasonic probe or the like. The A/D converted electric signal is referred to as echo data. The echo data is transferred as raw data to the medical data processing apparatus 1.

When the medical imaging apparatus 3 is the gantry of a PET apparatus, the gantry simultaneously measures by a simultaneous measurement circuitry a pair of gamma rays with 511 keV, which are generated in accordance with the annihilation of positrons generated from radionuclides accumulated in the subject and electrons around the radionuclide, thereby generating digital data having digital values indicative of the energy value and detection position of the pair of gamma rays (line of response (LOR)). This digital data is referred to as coincidence data or sinogram data. The coincidence data or sinogram data is transferred as raw data to the medical data processing apparatus 1.

When the medical imaging apparatus 3 is the C-arm of the X-ray diagnostic apparatus, the irradiation is from the X-ray tube provided in the C-arm. The X-rays produced by the X-ray tube and transmitted through the subject are received by the X-ray detector such as a flat panel display (FPD) arranged in the C-arm or arranged separately from the C-arm. The X-ray detector generates an electric signal having a crest value corresponding to the detected X-ray dose, and performs signal processing such as A/D conversion on this electric signal. The A/D converted electrical signal is referred to as X-ray image data. The X-ray image data is transferred as raw data to the medical data processing apparatus 1.

As shown in FIG. 3, the medical data processing apparatus 1 includes, as hardware resources, a processing circuitry 11, a memory 13, an input interface 15, a communication interface 17 and a display 19.

The processing circuitry 11 includes a processor such as a CPU or GPU. When activating the program installed in the memory 13 or the like, a processor implements an imaging control function 111, regular restoration function 112, input selection function 113, forward-propagation function 114, image processing function 115, display control function 116 and the like. Each of the functions 111 to 116 is not limited to being realized by a single processing circuitry. A plurality of independent processors may be combined into a processing circuitry, and each of the processors may execute the program to realize the functions 111 to 116.

With the imaging control function 111, the processing circuitry 11 controls the medical imaging apparatus 3 in accordance with imaging conditions, and performs medical imaging on the subject. The imaging conditions according to the present embodiment include imaging principles of the medical imaging apparatus 3 and various imaging parameters. The imaging principles correspond to the type of the medical imaging apparatus 3, or more specifically, to a magnetic resonance imaging apparatus, X-ray computed tomography imaging apparatus, PET apparatus, SPECT apparatus or ultrasonic diagnostic apparatus. The imaging parameters may include the field of view (FOV), imaging body part, slice position, frame (time phase of a medical image), temporal resolution, matrix size, and presence or absence of a contrast agent. For magnetic resonance imaging, the imaging parameters may further include the type of imaging sequences, parameters such as time to repeat (TR), echo time (TE), flip angle (FA), and type of k-space trajectory. For X-ray computer tomography, the imaging parameters further include X-ray conditions (tube current, tube voltage and X-ray exposure duration, etc.), the type of scanning (non-helical scanning, helical scanning, synchronous scanning, etc.), tilt angle, reconstruction function, number of views per rotation of the rotation frame, rotation speed, spatial resolution of the detector, and the like. For ultrasonic diagnosis, the imaging parameters include the focus position, gain, transmission intensity, reception intensity, PRF, a beam scanning scheme (sector scanning, convex scanning, linear scanning, etc.) and scanning mode (B-mode scanning, Doppler scanning, color Doppler scanning, M-mode scanning, and A-mode scanning, etc.).

With the regular restoration function 112, the processing circuitry 11 executes a regular restoration process on the raw data transferred from the medical imaging apparatus 3 to restore a medical image. The regular restoration process according to the present embodiment includes restoration from raw data to raw data, from raw data to image data, and from image data to image data. The restoration process from raw data defined by a certain coordinate system to two-dimensional image data or three-dimensional image data defined by a different coordinate system may be referred to as reconstruction processing or image reconstruction processing. The regular restoration process according to the present embodiment refers to restoration processing other than DNN restoration, which will be described later, such as denoising restoration and data error feedback restoration. The image reconstruction by the regular restoration process according to the present embodiment maybe divided into analytical image reconstruction and iterative reconstruction. The analytical image reconstruction for MR image reconstruction includes a Fourier transform and inverse Fourier transform. The analytical image reconstruction for CT image reconstruction includes the filtered back projection (FBP), convolution back projection (CBP), and their applications. The iterative reconstruction includes expectation maximization (EM), algebraic reconstruction technique (ART), and their applications.

With the input selection function 113, the processing circuitry 11 selects input medical data for the learned model 90. For the input medical data according to the present embodiment, input medical data that is a process target (hereinafter referred to as "target input data") and input medical data for assistance (hereinafter referred to as "auxiliary input data") are selected. As the typical target input data, the medical data that has data deficit and thus is to be restored, is selected. According to the present embodiment, the term 'data deficit' refers to a difference between actual medical data and desired medical data of the subject. For example, the data deficit may include data degradation due to noise produced by various causes, data missing due to a reduced number of sampling positions of medical data by sparse sampling of the projection data and k-space data, and information missing due to continuous values converted to discrete values in the A/D conversion. The auxiliary input data is medical data supplied to the learned model 90 to assist the reconstruction of the data deficit portion in the target input data by the learned model 90. For this auxiliary input data, a missing portion of the target input data, or a portion practically similar to such a portion, is supplied to the learned model 90. The auxiliary input data is therefore medical data relating to the same subject as the subject of the target input data and acquired under different imaging conditions. The imaging conditions of a target input image and of an auxiliary input image are set to produce a difference in such a manner that the auxiliary input image can be considered as practically similar to the target input image. With the auxiliary input data limited to the medical data of the same subject as the subject of the target input data, the accuracy and reliability of the target output data can be ensured. The auxiliary input image includes a single medical image, or a plurality of medical images of different imaging conditions.

With the forward-propagation function 114, the processing circuitry 11 receives the input of the target input data of the subject and the input of the auxiliary input data of the same subject acquired under imaging conditions that are different from the target input data. The processing circuitry 11 applies the learned model 90 to the target input data and the auxiliary input data, and generates the output medical data corresponding to the target input data. The output medical data is the medical data in which the data deficit portion that has been included in the target input data is restored. In other words, the learned model 90 is a multilayer network in which parameters p have been trained so that, when target input data including a data deficit and auxiliary input data that compensates for the data deficit are input, medical data that does not include the data deficit can be output. Combination examples of the input and the output of the learned model 90 include the modes as shown in FIGS. 4 and 5.

Figure 4:
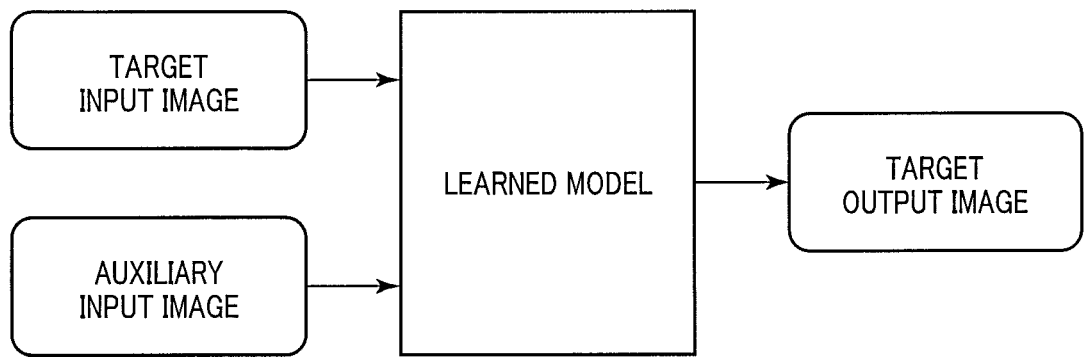
FIG. 4 is a diagram showing a combination example of input and output of a learned model according to the present embodiment.

FIG. 4 is a diagram showing an example of a combination of an input and an output of the learned model 90. For example, the learned model 90 receives the input of a target input image, which is the target input data, and the input of an auxiliary input image, which is the auxiliary input data, as shown in FIG. 4. The target input image is medical image data relating to the process target subject. The auxiliary input image is medical image data of the same subject as the process target subject, and this medical image data imaged is acquired under different imaging conditions from the target input image. If this is the case, a target output image is output from the learned model 90. The target output image is the process target medical image data in which the data deficit portion included in the target input image is restored.

Figure 5:
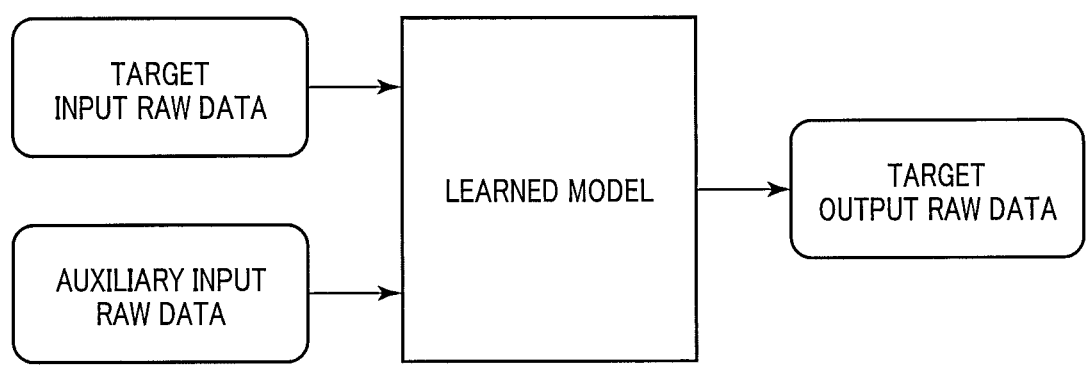
FIG. 5 is a diagram showing another combination example of input and output of a learned model according to the present embodiment.

FIG. 5 is a diagram showing another example of the combination of the input and the output of the learned model 90. For example, as shown in FIG. 5, the learned model 90 receives the input of the target input raw data as the target input data and the input of the auxiliary input raw data as the auxiliary input data. The target input raw data is the raw data of the process target subject. The auxiliary input raw data is the raw data of the same subject as the process target subject, and this raw data is acquired under different imaging conditions from the target input raw data. If this is the case, the target output raw data is output from the learned model 90. The target output raw data is the raw data of the process target in which the data deficit portion included in the target input raw data is restored.

According to the present embodiment, the raw data is not limited to the original raw data acquired by the medical imaging apparatus 3. The raw data according to the present embodiment maybe computational raw data generated by executing the forward projection processing on the medical image generated by the regular restoration function 112 or the forward-propagation function 114. The raw data according to the present embodiment may be original raw data that has been subjected to any data processing, such as data compression processing, resolution decomposition processing, data interpolation processing, and resolution combination processing. The raw data according to the present embodiment may be, if it is three-dimensional raw data, hybrid data subjected to the restoration processing for one or two axes. The medical image according to the present embodiment is also not limited to the original medical image generated by the regular restoration function 112 or the forward-propagation function 114. The medical image according to the present invention may be an original medical image that has been subjected to any image processing, such as image compression processing, resolution decomposition processing, image interpolation processing, and resolution combination processing.

With the image processing function 115, the processing circuitry 11 performs various types of image processing on the medical image generated by the regular restoration function 112, the target output image generated by the forward-propagation function 114, and the like. For example, the processing circuitry 11 may perform three-dimensional image processing such as volume rendering, surface volume rendering, pixel value projection processing, multi-planer reconstruction (MPR) processing, and curved MPR (CPR) processing. The processing circuitry 11 may further perform positioning processing as image processing.

With the display control function 116, the processing circuitry 11 displays various types of information on the display 19. For example, the processing circuitry 11 may display a medical image generated by the regular restoration function 112, a target output image generated by the forward-propagation function 114, and a medical image subjected to the image processing by the image processing function 115. The processing circuitry 44 may also display the target input data and auxiliary input data selected by the input selection function 113.

The memory 13 is a storage device such as a read-only memory (ROM), a random access memory (RAM), a hard disk drive (HDD), a solid state drive (SSD), and an integrated circuitry storage device for storing various types of information. The memory 13 stores, for example, the learned models generated by the model learning apparatus 5. In place of the above storage device, the memory 13 may be a drive device that reads and writes various types of information from and to a portable storage medium such as a compact disc (CD), a digital versatile disc (DVD) and a flash memory, or a semiconductor memory device. The memory 13 may be provided in a computer coupled to the medical data processing apparatus 1 via a network.

The input interface 15 receives various input operations from the user, converts the received input operations into electric signals, and outputs the signals to the processing circuitry 11. Specifically, the input interface 15 is coupled to input devices such as a mouse, a keyboard, a track ball, a switch, a button, a joystick, a touch pad and a touch panel display. The input interface 15 outputs to the processing circuitry 11 an electric signal corresponding to the input operation to the input device. Furthermore, the input device coupled to the input interface 15 may be provided in a computer coupled via a network or the like.

The communication interface 17 is an interface for data communications with the medical imaging apparatus 3, the model learning apparatus 5, and the training data storage apparatus 7, as well as other computers.

The display 19 displays various types of information according to the display control function 116 of the processing circuitry 11. For example, the display 19 may display a medical image generated by the regular restoration function 112, a target output image generated by the forward-propagation function 114, and a medical image subjected to the image processing by the image processing function 115. The display 19 outputs a graphical user interface (GUI) or the like for receiving various operations from the user. For example, as the display 19, a liquid crystal display (LCD), a cathode ray tube (CRT) display, an organic electroluminescence display (OELD), a plasma display, or any other display may be suitably adopted.

The processing performed by the medical data processing apparatus 1 will be described below. In the following description, medical images will be considered as the medical data.

FIG. 6 is a diagram showing the detailed structure of a learned model 90 according to the present embodiment. The learned model 90 according to the present embodiment has an input layer 91, an intermediate layer 93 and an output layer 95, as shown in FIG. 6. The input layer 91 receives a target input image and an auxiliary input image. The target input image and the auxiliary input image are entered in any of the aforementioned input forms (2), (3) and (5). For example, as shown in FIG. 6, the form (2) is adopted. If this is the case, the components (pixel values) of the target input image and auxiliary input image are entered as a single input vector 92 to the input layer 91. When the number of pixels of the target input image is q, the number of pixels of the auxiliary input image is r, and q+r=N, the input layer 91 is provided with N input units. The input layer 91 is divided into an input unit area (hereinafter referred to as "process target area") 921 for the target input image and an input unit area (referred to as "auxiliary area") 922 for the auxiliary input image. The process target area 921 includes q input units to which the p-th pixel value $x_p$ ($1 \leq p \leq q$) of the target input image is entered, and the auxiliary area 922 includes r input units to which the p-th pixel value $x_p$ ($1 \leq p \leq r$) of the auxiliary input image is entered.

When the target input raw data and the auxiliary input raw data are entered to the learned model 90, the components of the target input raw data and the auxiliary input raw data are data values.

The output layer 95 outputs a target output image. The target output image is output from the output layer 95 in the form of a single output vector 96. The output vector 96 includes a plurality of components y. Each of the components y is the pixel value of a pixel in the target output image. The output unit area 961 of the output layer 95 is limited to the area for a single target output image. The number M of components y is not always limited to the same number as the number q of pixels of the target input image. The number M may be smaller or larger than the number q of pixels.

The target input image is always entered to the input unit of the process target area 921, and not to the input unit of the auxiliary area 922. On the other hand, the auxiliary input image is always entered to the input unit of the auxiliary area 922, and not to the input unit of the process target area 921. In other words, the positions of the input units in the input layer 91 to which the target input image and the auxiliary input image are entered do not vary for each forward propagation of the learned model 90, but are always fixed. In this manner, the learned model 90 recognizes the image entered to the process target area 921 as a target input image, and the image entered to the auxiliary area 922 as an auxiliary input image. The positions of the input unit in the input layer 91 to which the target input image and the auxiliary input image are entered are defined in accordance with the positions at which the target input image and auxiliary input image are entered during the training of the multilayer network. That is, if the target input image is input to the first half area of the input layer 91 and the auxiliary input image is input to the second half area of the input layer 91 during the training, the first half area is determined as the input position for the target input image, and the second half area is determined as the input position for the auxiliary input image.

In the above description, the process target area 921 of the input unit for the target input image is determined as the first half area of the input layer 91, and the auxiliary area 922 of the input unit for the auxiliary input image is determined as the second half area of the input layer 91. However, the present embodiment is not limited thereto. The process target area 921 of the input unit for the target input image may be determined as the second half area of the input layer 91, while the auxiliary area 922 of the input unit for the auxiliary input image may be determined as the first half area of the input layer 91.

The auxiliary input image may be two sets or more of medical images acquired with different imaging conditions. If this is the case, the components of the target input image and two or more auxiliary input images are entered to the input layer 91 as a single input vector 92. It is preferable that the areas of the input units for two or more auxiliary input images should always be fixed, without differing for each time of the forward propagation. For example, if the input unit area for the first auxiliary input image for a frame of one second after the target input image is defined as q to r, and the input unit area for the second auxiliary input image for a frame of two seconds after is defined as r+1 to s, the first auxiliary input image for the frame of one second after should always be entered to the input unit in the area of q to r, and not in the area of r+1 to s. If necessary, the first auxiliary input image for a frame of one second after may be entered to the input unit in the area of r+1 to s.

Next, an operation example of the medical data processing apparatus 1 according to the present embodiment will be described. In the following description, the multilayer network according to the present embodiment is a deep neural network (DNN), which is a multi-layered network model designed to resemble the neural circuitry of the brain of a living being. The medical data processing apparatus 1 executes DNN restoration based on the raw data acquired by the medical imaging apparatus 3, and generates medical image data relating to the subject. The DNN restoration according to the present embodiment means a method of restoring data from raw data to a medical image, using a learned DNN 90 as the learned model 90.

As a DNN according to the present embodiment, any DNN structure may be adopted. For example, a residual network (ResNet), dense convolutional network (DenseNet), or U-Net may be used as a DNN according to the present embodiment.

FIG. 7 is a diagram showing a typical flow of the DNN restoration processing by the medical data processing apparatus 1. At the start in FIG. 7, the process target raw data of the subject has been acquired by the medical imaging apparatus 3 and transferred to the medical data processing apparatus 1. The process target raw data includes a data deficit. When the user sends a command to start the DNN restoration processing via the input device or the like, the processing circuitry 11 executes the DNN restoration program and starts the processing of FIG. 7.

As shown in FIG. 7, the processing circuitry 11 implements the regular restoration function 112 (step SA1). At step SA1, the processing circuitry 11 performs normal reconstruction processing on the process target raw data to generate a target input image. With the process target raw data containing a data deficit, the quality of the target input image is insufficient. The target input image generated by applying a regular restoration process to the process target raw data may also be referred to as a tentative restoration image.

After step SA1, the processing circuitry 11 implements the input selection function 113 (step SA2). At step SA2, the processing circuitry 11 selects a target input image and an auxiliary input image. The processing circuitry 11 may select the target input image generated at step SA1 as an input image. The processing circuitry 11 may also select an auxiliary input image for the target input image as an input image. As the auxiliary input image, a medical image relating to the same subject as the subject of the target input image and acquired based on imaging conditions that are different from the imaging conditions for the target input image is selected. The processing circuitry 11 may automatically select an auxiliary input image according to predetermined rules, or may select an auxiliary input image manually according to a command entered through the input device or the like by the user.

The auxiliary input image may be selected according to the type of learned DNN 90 that is to be used. The learned DNN 90 according to the present embodiment is generated for each imaging condition of the auxiliary input image that is different from the imaging condition of the target input image. For example, if a learned DNN 90 that is to be used adopts, as an auxiliary input image, a medical image of a slice different from the target input image, the processing circuitry 11 selects as an auxiliary input image a medical image of a slice different from the process target medical image. For such an auxiliary input image, a medical image of a slice that is physically (spatially and/or temporally) close to the slice of the target input image may be selected. In the case of electrocardiographic synchronous scanning, a medical image of a slice having a cardiac phase the same as or temporally close to the cardiac phase of the slice of the target input image is selected as an auxiliary input image. The auxiliary input image candidates are stored in advance in the memory 13.

One or more auxiliary input images may be selected. The number of auxiliary input images to be selected is set to the number of auxiliary input images that are entered during the training of the DNN that is to be used. In other words, if the DNN to be used has undergone the training with one medical image as an auxiliary input image, one medical image is selected as an auxiliary input image for DNN restoration. If two medical images are entered as auxiliary input images during the training of the DNN, two medical images are selected as auxiliary input images also for DNN restoration.

Any other restrictions may be imposed on the auxiliary input images that are to be selected. For example, the processing circuitry 11 may select, as an auxiliary input image, only a medical image of the same FOV as the FOV of the target input image. The processing circuitry 11 may remove any medical images with an imaging date a predetermined number of days (for example, two months) or more before the imaging date of the target input image, from candidate auxiliary input images.

After step SA2, the processing circuitry 11 implements the forward-propagation function 114 (step SA3). At step SA3, the processing circuitry 11 reads the learned DNN 90 to be used, from the memory 13. The learned DNN 90 to be read may be designated by the user via the input device. The processing circuitry 11 applies the read learned DNN 90 to the target input image and auxiliary input image selected at step SA2 to generate a target output image. For example, Equations (4-1) and (4-2) are calculated by incorporating the target input image and auxiliary input image as input x of Equation (3-2) so that a target output image y can be obtained.

The learned DNN 90 may be generated and stored in the memory 13 for each imaging body part. By generating a learned DNN 90 for each imaging body part, the restoration accuracy of the target output image can be improved. The processing circuitry 11 switches learned DNNs 90 in accordance with the selected imaging body part. The imaging body part may be selected by the user via the input device when executing the DNN restoration processing. If this is the case, the processing circuitry 11 reads from the memory 13 the learned DNN 90 associated with the selected imaging body part. If an imaging body part has already been selected for medical imaging, the processing circuitry 11 may automatically read from the memory 13 a learned model 90 associated with the selected imaging body part. If the medical imaging apparatus 3 uses different devices depending on the imaging body part, the imaging body part corresponding to a certain device may be automatically identified, and a learned model 90 associated with the identified imaging body part may be automatically read from the memory 13. For example, for magnetic resonance imaging, different types of coils, such as the head coil and abdominal coil, are adopted depending on the imaging body part. For such a case, the processing circuitry 11 identifies the imaging body part corresponding to the type of the used coil from the identifier of the coil or the like, and reads a learned model 90 associated with the identified imaging body part from the memory 13.

After step SA3, the processing circuitry 11 implements the display control function 116 (step SA4). At step SA4, the processing circuitry 11 displays the target output image generated at step S3 on the display 19.

The flow of the DNN restoration processing shown in FIG. 7 has been explained. The above flow of the DNN restoration processing is described merely as an example, and thus the flow of the DNN restoration processing according to the present embodiment should not be limited thereto. For example, if the medical data processing apparatus 1 is provided independently of the medical image diagnostic apparatus 9, both target input image candidates and auxiliary input image candidates may be stored in the memory 13 in advance so that a target input image and an auxiliary input image can be selected from these candidates. In addition, preprocessing such as resolution decomposition or composition may be performed on the raw data, and post-processing such as volume rendering or image analysis may be performed on the target output image. The processing circuitry 11 may align the target input image and the auxiliary input image at a step prior to the forward-propagation processing of step SA3. The target input image and auxiliary input image may be selected after reading the to-be-used learned DNN 90.

The processing circuitry 11 may manage the target output images in such a manner that the user can acknowledge the use of data other than the raw data to generate the target output images. For example, when managing based on the Digital Imaging and Communications in Medicine (DICOM) standards, the processing circuitry 11 associates a target output image with a target input image and an auxiliary input image, and thereby manages these three images as a single set of images. For example, a target output image, together with a process input image and an auxiliary input image, are stored in the image file of the target output image or target input image. In addition to or in combination with the above method, the processing circuitry 11 may assign the identification information of the auxiliary input image to the DICOM tag of the target output image. With these methods, the indication of the target output image that has been generated using the auxiliary input image can be kept in the target output image. The processing circuitry 11 may assign the identification information of the target output image to the DICOM tag of the target input image. In this manner, the presence of a target output image can be specified.

Next, a specific example of the DNN restoration processing will be described.

As mentioned above, the target input image and the auxiliary input image relate to the same subject and to different imaging conditions. Imaging conditions include an imaging principle and multiple types of imaging parameters. Imaging parameters are divided into common parameters and individual parameters. The common parameters are imaging parameters that are set to the same values for the target input image and the auxiliary input image. The individual parameters are imaging parameters that are set to different values for the target input image and the auxiliary input image. For the target input image and target output image, the common parameters and individual parameters have the same values. The target input image and the target output image differ from each other in data deficit amount or image quality. In other words, the target output image has a lower data deficit amount or a higher image quality than the target input image. The data deficit amount and the image quality can be evaluated by image quality parameters such as image SD.

FIG. 8 is a schematic diagram showing the relationship between the input and output of the learned DNN in the forward-propagation processing according to the present embodiment. The learned DNN shown in FIG. 8 receives as an auxiliary input image a medical image having a slice position that is different from the target input image. As a target output image, a medical image of the same slice position as the target input image is output, in which the data deficit portion included in the target input image is restored. For example, the slice of the target input image has a position sA, the slice of the auxiliary input image has a position sB that is different from the position sA, and the slice of the target output image has the position sA, as shown in FIG. 8. It is preferable that the distance and angle of the position sB with respect to the position sA be maintained at the same values without being varied for every DNN restoration, although the values are not particularly defined. In the case of FIG. 8, the individual parameter represents the slice position, while the common parameters may represent the type of acquisition sequence, the type of k-space trajectory, temporal resolution, and the like.

FIG. 9 is a schematic diagram showing another relationship between the input and output of the learned DNN in the forward-propagation processing according to the present embodiment. The learned DNN shown in FIG. 9 receives as an auxiliary input image a medical image of a frame that is different from the target input image. The frame according to the present embodiment corresponds to the acquisition time of the medical image or raw data. As a target output image, a medical image of the same frame as the target input image is output, in which the data deficit portion included in the target input image is restored. For example, the frame of the target input image has a time phase tA, the frame of the auxiliary input image has a time phase tB, and the frame of the target output image has a time phase tA, as shown in FIG. 9. It is preferable that the time difference of the time phase tB with respect to the time phase tA be maintained at the same value without being varied for each DNN restoration, although the value is not particularly defined. In the case of FIG. 9, the individual parameter represents a frame (acquisition time), while the common parameters may represent the slice position, the type of acquisition sequence, the type of k-space trajectory, temporal resolution, and the like.

FIG. 10 is a schematic diagram showing another relationship between the input and output of the learned DNN in the forward-propagation processing according to the present embodiment. The learned DNN shown in FIG. 10 receives as an auxiliary input image a medical image of a slice position and frame that are both different from those of the target input image. As a target output image, a medical image of the same slice position and frame as those of the target input image is output, in which the data deficit portion included in the target input image is restored. For example, the target input image has a slice position sA, and a frame of a time phase tA; the auxiliary input image has a slice position sB and a frame of time phase tB; and the target output image has the slice sA and the frame of the time phase tA, as shown in FIG. 10. In the case of FIG. 10, the individual parameter represents either a slice position or a frame, while the common parameters represent the type of acquisition sequence, the type of k-space trajectory, temporal resolution, and the like. When a plurality of images are selected as auxiliary input images, the auxiliary input images may be set to have different values for only one of the slice position and the frame, or to have different values for both of the slice position and the frame.

Figure 11:
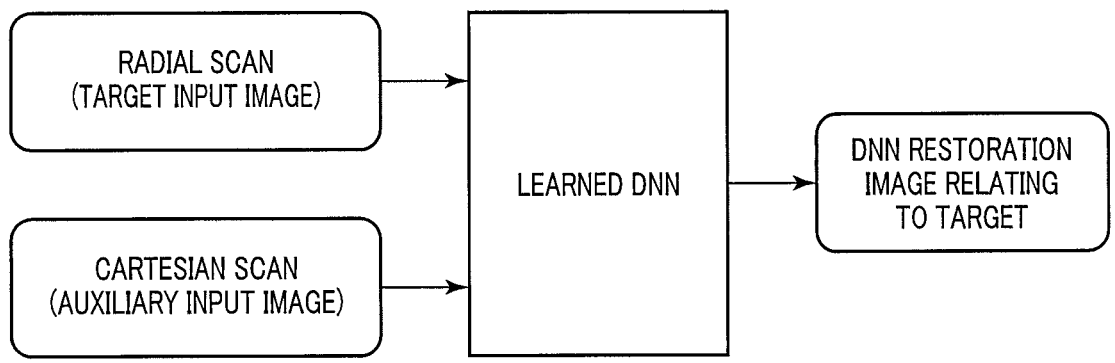
FIG. 11 is a schematic diagram showing still another relationship between the input and the output for the learned deep neural network in the forward-propagation processing according to the present embodiment.

FIG. 11 is a schematic diagram showing another relationship between the input and output of the learned DNN in the forward-propagation processing according to the present embodiment. For the learned DNN shown in FIG. 11, the auxiliary input image is different from the target input image in the k-space trajectory of the magnetic resonance imaging. As a target output image, a medical image having the same k-space trajectory as the target input image is output, in which a data deficit portion included in the target input image is restored. Examples of the k-space trajectories include Cartesian scanning, radial scanning, periodically rotated overlapping parallel lines with enhanced reconstruction (PROPELLAR), spinal scanning, and stack-of-stars. For example, the k-space trajectory of a target input image may be radial scanning, the k-space trajectory of an auxiliary input image is Cartesian scanning, and the k-space trajectory of a target output image is radial scanning, as shown in FIG. 11. The k-space trajectory according to the present embodiment also includes the acquisition order of acquisition lines. The acquisition lines according to the present embodiment correspond to the phase encode step in Cartesian scanning and the spokes in radial scanning. The centric order or sequential order maybe adopted for the acquisition order of the Cartesian scanning. The k-space trajectory of the target input image may be in centric order, while the k-space trajectory of the auxiliary input image may be in sequential order. In the case of FIG. 11, the individual parameter represents the type of k-space trajectory, and the common parameters represent the type of acquisition sequence, slice position and the like.

Figure 12:
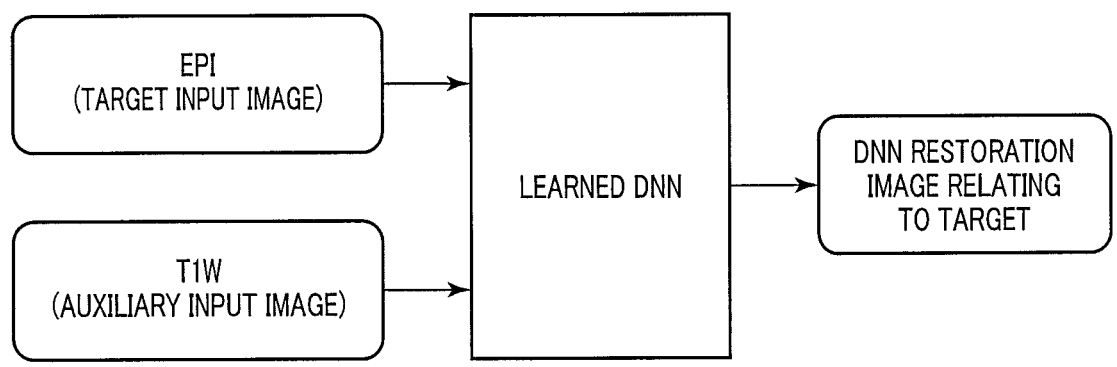
FIG. 12 is a schematic diagram showing still another relationship between the input and the output for the learned deep neural network in the forward-propagation processing according to the present embodiment.

FIG. 12 is a schematic diagram showing another relationship between the input and output of the learned DNN in the forward-propagation processing according to the present embodiment. The learned DNN shown in FIG. 12 receives, as an auxiliary input image, a medical image having an acquisition sequence that is different from the target input image in the magnetic resonance imaging. As a target output image, a medical image of the same acquisition sequence as the target input image is output, in which a data deficit portion included in the target input image is restored. Examples of the acquisition sequences according to the present embodiment may include an acquisition sequence type such as gradient echo (GRE) sequence, spin echo (SE) sequence or the like. A pulse sequence may have preparation pulses such as inversion recovery (IR) pulses or fat saturation pulses inserted, or may adopt echo planar imaging (EPI). According to the present embodiment, the elements that determine a acquisition sequence include parameters indicative of not only the type of acquisition sequence but also of the repetition time TR, echo time TE, longitudinal relaxation time T1, transverse relaxation time T2, value b, and double speed rate of the acquisition sequence. As shown in FIG. 12, for example, the acquisition sequence of a target input image is EPI acquisition; the acquisition sequence of an auxiliary input image is T1W acquisition; and the acquisition sequence of a target output image is EPI acquisition. In the case of FIG. 12, the individual parameter represents the type of acquisition sequence, while the common parameters represent the type of k-space trajectory, slice position, temporal resolution and the like.

FIG. 13 is a schematic diagram showing another relationship between the input and output of the learned DNN in the forward-propagation processing according to the present embodiment. For the learned DNN shown in FIG. 13, a target input image and two types of auxiliary input images are entered to the learned DNN. For the target output image, a medical image of the same acquisition sequence as the target input image is output, in which a data deficit portion included in the target input image is restored. The two auxiliary input images are different from the target input image in acquisition sequence. For example, the acquisition sequence of the target input image is based on the EPI acquisition with value b=500, the acquisition sequence of the first auxiliary input image is based on the EPI acquisition with value b=0, and the acquisition sequence of the second auxiliary input image is based on the T1W acquisition. The acquisition sequence of the target output image in this case is based on the EPI acquisition with value b=500. In the case of FIG. 13, the individual parameter is one of the type of acquisition sequence and value b, and the common parameters are the slice position, the type of k-space trajectory, the temporal resolution, and the like. When multiple images are selected as auxiliary input images, the images may be set such that either one of the type of acquisition sequence and the value b, or both of them, may have different values for the auxiliary input images.

The above types of the target input image and auxiliary input image are provided as examples, and the present embodiment is not limited thereto.

The following types may be adopted as two input images of different k-space trajectories: MR image acquired as a target input image by random undersampling and MR image acquired as an auxiliary input image by regular undersampling, where regular undersampling is sparse sampling by Cartesian scanning. Random undersampling, also referred to as pseudo-radial scanning, is a method of acquiring k-space data along the pseudo-radial acquisition lines by Cartesian scanning.

In the above embodiment, the medical data processing apparatus 1 is described as a computer included in the medical image diagnostic apparatus 9. The medical data processing apparatus according to the present embodiment, however, is not limited thereto.

FIG. 14 is a diagram showing the structure of a different medical data processing apparatus 2 according to the present embodiment. The medical data processing apparatus 2 is dedicated to the forward-propagation function 114. The medical data processing apparatus 2 may be realized by a computer that is not included in the medical image diagnostic apparatus 9. Alternatively, the medical image diagnostic apparatus 2 may be realized by an integrated circuitry such as ASIC or FPGA, which is included, or not included, in the medical image diagnostic apparatus 9. In the following description, the medical data processing apparatus 2 is assumed to be an ASIC.

As shown in FIG. 14, the medical data processing apparatus 2 includes a processing circuitry 21, a memory 23, an input interface 25, and an output interface 27. The processing circuitry 21, the memory 23, the input interface 25 and the output interface 27 are connected to each other via a bus.

The processing circuitry 21 is a combined set of circuit elements or logic circuits designed to execute the forward-propagation function 114. The processing circuitry 21 generates a target output image by applying a learned model to a target input image and auxiliary input image that are entered via the input interface 25, and outputs a target output image via the output interface 27.

The memory 23 is a circuitry element that stores any information, such as ROM and RAM. For example, the memory 23 may store calculation results obtained at the time of implementing the forward-propagation function 114.

The input interface 25 is an interface for input to the processing circuitry 21. The input interface 25 may enter a target input image and an auxiliary input image to the processing circuitry 21. The target input image and the auxiliary input image may be selected by a computer equipped with the medical data processing apparatus 2.

The output interface 27 is an interface for output from the processing circuitry 21. The output interface 27 may output a target output image that is output from the processing circuitry 21 to a computer, a network, a storage device, or the like.

The above configuration allows the medical data processing apparatus 2 to implement the forward-propagation function 114 in a form other than a computer in the medical image diagnostic apparatus 9. The configuration of the medical data processing apparatus 2 in FIG. 14 is described merely as an example, and should not be limited thereto. For example, the medical data processing apparatus 2 may not include a memory 23. Furthermore, the processing circuitry 21 may be provided with functions other than the forward-propagation function 114.

Figure 15:
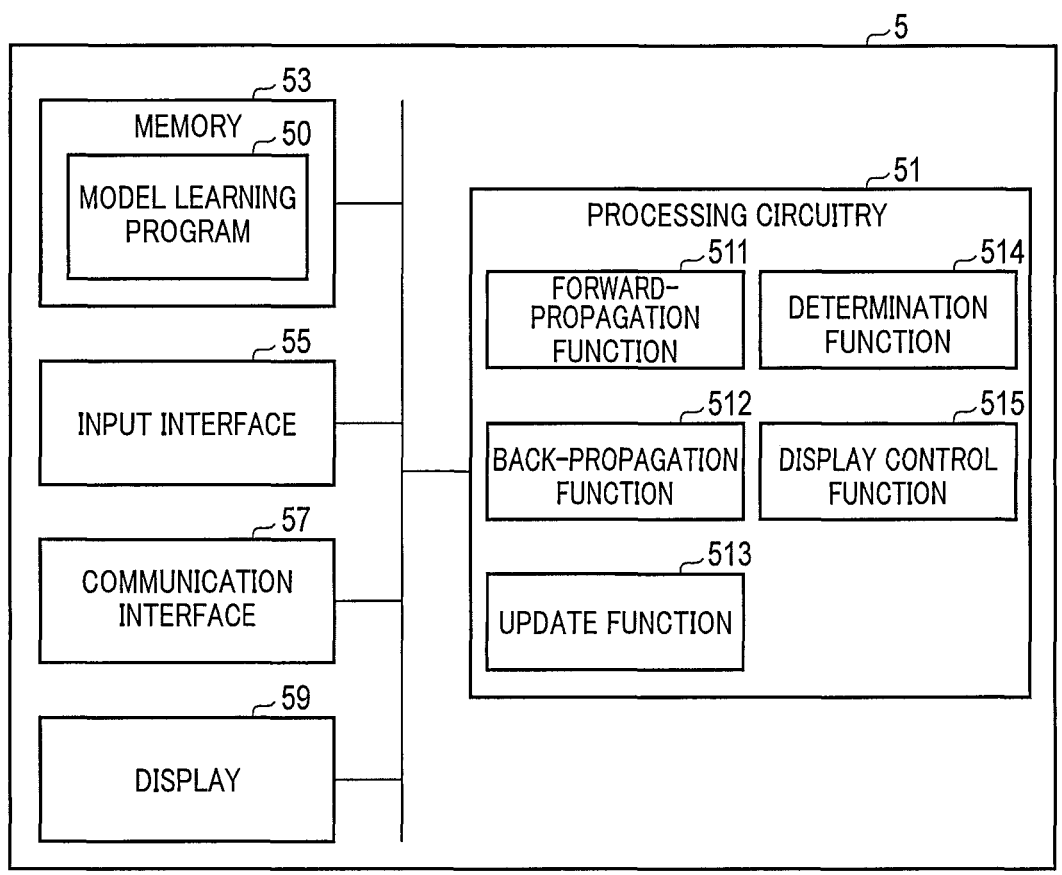
FIG. 15 is a diagram showing the structure of the model learning apparatus illustrated in FIG. 1.

FIG. 15 is a diagram showing the structure of the model learning apparatus 5. The model learning apparatus 5 includes, as hardware resources, a processing circuitry 51, a memory 53, an input interface 55, a communication interface 57 and a display 59, as shown in FIG. 15.

The processing circuitry 51 has a processor such as a CPU or a GPU. By activating the DNN restoration program installed in the memory 53 or the like, the processor implements the forward-propagation function 511, back-propagation function 512, update function 513, determination function 514 and display control function 515. Each of the functions 511 to 515, however, is not limited to being realized by a single processing circuitry. A plurality of independent processors may be combined into a processing circuitry, and the functions 511 to 515 may be realized by each of the processors executing the program.

With the forward-propagation function 511, the processing circuitry 51 performs forward propagation on the input medical data in the multilayer network, and computes the estimated output data corresponding to the input medical data.

With the back-propagation function 512, the processing circuitry 51 performs the backpropagation in the multilayer network, and computes a gradient vector. The error is defined by the difference between the estimated output data calculated by the forward-propagation function 511 and the true output data.

With the update function 513, the processing circuitry 51 updates the parameters of the multilayer network based on the gradient vector calculated by the back-propagation function 512. Specifically, the processing circuitry 51 updates the parameters so that the estimated output medical data and the true output medical data approximate each other.

With the determination function 514, the processing circuitry 51 determines whether or not the condition for terminating the training process is satisfied. The condition for terminating can be set freely by the user via an input device or the like.

With the display control function 515, the processing circuitry 51 displays the training data and the training result on the display 59.

The memory 53 is a storage device for storing various kinds of information, such as a ROM, RAM, HDD, SSD, integrated circuit storage device or the like. The memory 53 stores, for example, a model learning program 50 for training the multilayer network. Instead of the above storage device, the memory 53 may be a driving device for reading and writing various kinds of information from and to a portable storage medium such as a CD, a DVD, a flash memory or the like, or a semiconductor memory device such as a RAM. Alternatively, the memory 53 may be provided in a separate computer connected to the model learning apparatus 5 via a network.

The input interface 55 receives various input operations from the user, converts the received input operations into electric signals, and outputs them to the processing circuitry 51. Specifically, the input interface 15 is coupled to input devices such as a mouse, a keyboard, a track ball, a switch, buttons, a joystick, a touch pad and a touch panel display. The input interface 55 outputs the electric signals corresponding to the input operations to the input device to the processing circuitry 51. Furthermore, the input device connected to the input interface 55 may be an input device provided in a separate computer connected via a network or the like.

The communication interface 57 is an interface for data communications with the medical data processing apparatus 1, the medical imaging apparatus 3, the training data storage apparatus 7, and other computers.

The display 59 displays various kinds of information in accordance with the display control function 515 of the processing circuitry 51. For example, the display 59 may display the training data and training results. The display 59 further outputs a GUI or the like for receiving various operations from the user. As the display 19, a liquid crystal display, a CRT display, an organic EL display, a plasma display or any other display may be suitably adopted.

Figure 16:
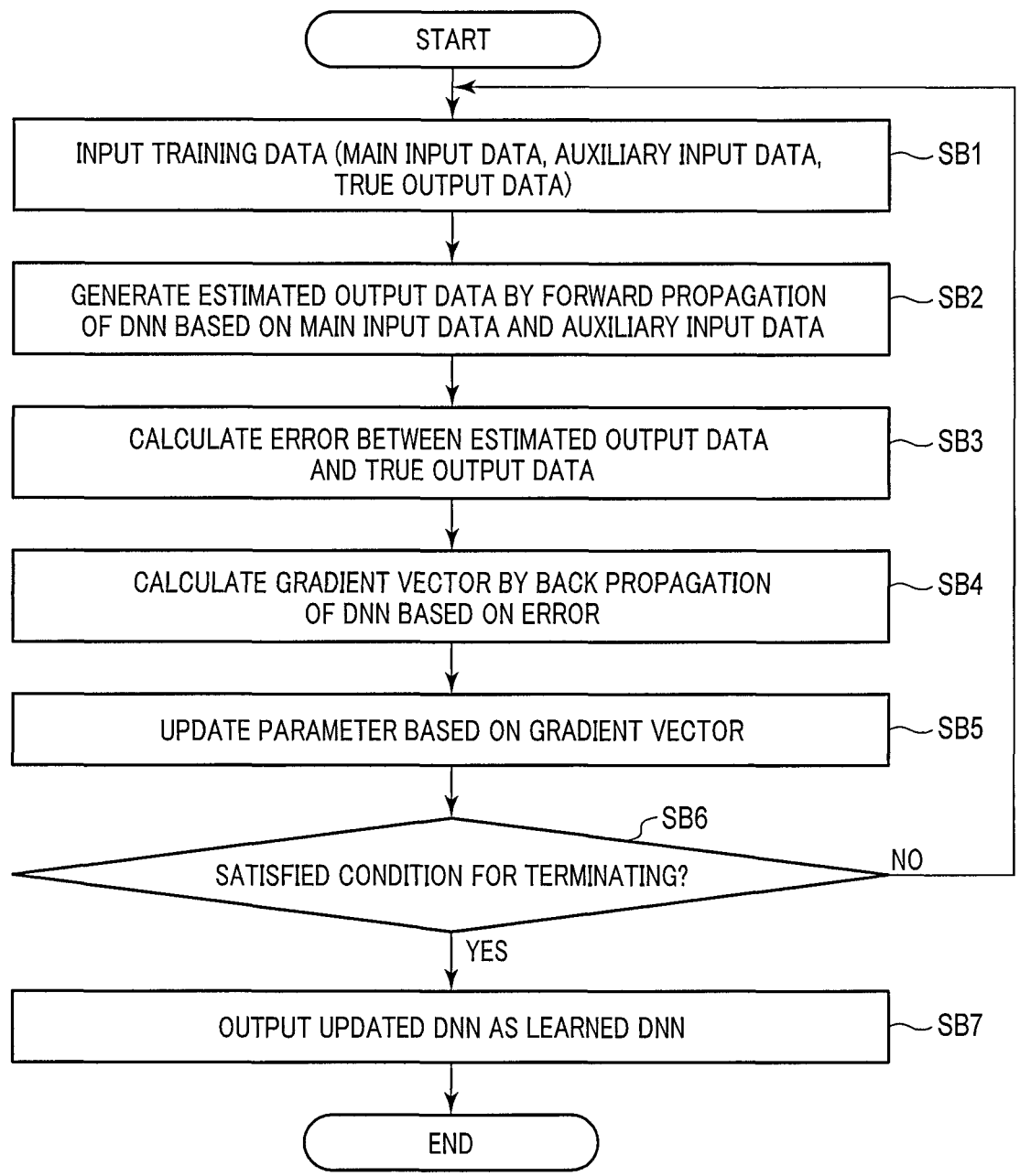
FIG. 16 is a diagram showing a typical flow of the model learning process executed by the processing circuitry of the model learning apparatus of FIG. 15 in line with a model learning program.

Next, the model learning process executed by the processing circuitry 51 of the model learning apparatus 5 in accordance with the model learning program 50 will be described. FIG. 16 is a diagram showing a typical flow of a model learning process executed by the processing circuitry 51 of the model learning apparatus 5 in accordance with the model learning program 50. In response to a command for starting the model learning process that is input by the user, the processing circuitry 51 initiates the processing of FIG. 16 by executing the model learning program 50.

First, the processing circuitry 51 implements the forward-propagation function 511 (step SB1). At step SB1, the processing circuitry 51 inputs the training data including a plurality of training samples. The training data is supplied from the training data storage apparatus 7. A training sample is a combination of main input data, auxiliary input data and true output data. The main input data and the auxiliary input data are medical data of the same subject acquired under different imaging conditions. The main input data corresponds to the target input data. The true output data is the desired output data (true output or supervisory data) output from the DNN to which the main input data is input.

As previously described, the imaging parameters include a common parameter and an individual parameter. For the main input data and auxiliary input data, the common parameters are set to the same value, while the individual parameters are set to different values. For the main input data and true output data, the common parameter and individual parameter are set to the same values. The true output data contains less data deficit or has higher image quality than the main input data. If the imaging parameter is, for example, an MRI imaging parameter, the main input data is an MR image based on the k-space data containing a small amount of data, while the true output data is an MR image based on k-space data containing a larger amount of data than the main input data. If the main input data is data acquired by sparse sampling, it is preferable that the true output data be data acquired by full sampling. The individual parameter of the auxiliary input data and the individual parameter of the true output data are set to different values. In the case of the auxiliary input data having multiple sets, the individual parameters for different auxiliary input data may have the same value or different values. The true output data is based on the main input data, but is independent of the auxiliary input data. In general, when the data input to and output from the DNN is k-space data, the true output k-space data contains main input k-space data, but does not contain auxiliary input k-space data. In general, when the data input to and output from the DNN is images, the k-space data used for the reconstruction of a true output image includes the k-space data used for the reconstruction of a main input image, but does not include the k-space data used for the reconstruction of an auxiliary input image.

For a plurality of training samples entered to the same DNN, imaging conditions of the main input data and imaging conditions of the auxiliary input data that differ from each other are maintained as being of the same combination. Specifically, the combination of imaging conditions of the main input data and imaging conditions of the auxiliary input data that differ from each other is fixed to the combination of the imaging conditions of the main input data and the imaging conditions of the auxiliary input data for the generation target DNN. For example, when generating the DNN of FIG. 8, a medical image having a slice position that is different from the main input medical image is selected as an auxiliary input image. When generating the DNN of FIG. 9, a medical image in a frame that is different from that of the main input medical image is selected as an auxiliary input image. When generating the DNN of FIG. 10, a medical image having a slice position that is different from that of the main input medical image and a medical image in a frame that is different from that of the main input medial image are selected as auxiliary input images. When generating the DNN of FIG. 11, a medical image having a k-space trajectory that is different from that of the main input medical image is selected as an auxiliary input image. When generating the DNN of FIG. 12, a medical image having a acquisition sequence that is different from that of the main input medical image is selected as an auxiliary input image. When generating the DNN of FIG. 13, two medical images having acquisition sequences that are different from the acquisition sequence of the main input medical image are selected as auxiliary input images.

The main input medical image and auxiliary input images for training are not limited to medical images generated by taking images of a patient. Medical images generated by taking images of a phantom may be used as a main input medical image and auxiliary input image.

After step SB1, the processing circuitry 51 generates output data by forward propagation of the DNN based on the main input data and auxiliary input data (step SB2). The output data generated at step SB2 is referred to as estimated output data. The parameter of the DNN is set to an initial value in the first forward propagation. For example, the previously indicated Equations (4-1) and (4-2) are computed with the main input data and auxiliary input data as inputs, and estimated output data $z^{(L)}$ is thereby generated. In order to improve the training efficiency and training accuracy, it is preferable to align the main input data with the auxiliary input data at a stage prior to the forward propagation.

After step SB2, the processing circuitry 51 implements the back-propagation function 512 (step SB3). At step SB3, the processing circuitry 51 calculates the error between the estimated output data that is generated at step SB2 and the true output data that is entered at step SB1. Specifically, by subtracting the estimated output data $z^{(L)}$ from the true output data $d_n$, the error $\delta_j^{(L)}$ defined by Equation (13-1) can be obtained.

After step SB3, the processing circuitry 51 finds a gradient vector by back propagation of the DNN based on the error obtained at step SB3 (step SB4). Specifically, the gradient vector of Equation (6-2) or (6-4) is calculated based on the error $\delta_j^{(L)}$.

After step SB4, the processing circuitry 51 implements the update function 513 (step SB5). At step SB5, the processing circuitry 51 updates the parameter based on the gradient vector obtained at step SB4. Specifically, the parameter p is updated by Equation (6-1) or (6-3) based on the gradient vector.

After step SB5, the processing circuitry 51 executes the determination function 514 (step SB6). At step SB6, the processing circuitry 51 determines whether or not the condition for terminating is satisfied. The condition for terminating, for example, may be determined as whether the number of repetitions reaches a preset number. Alternatively, the condition for terminating may be determined as whether the gradient vector falls below a threshold value.

When it is determined at step SB6 that the condition for terminating is not satisfied (no at step SB6), the processing circuitry 11 repeats steps SB1 to SB6, using the same training sample or a different training sample.

When it is determined at step SB6 that the condition for terminating is satisfied (yes at step SB6), the processing circuitry 11 outputs the updated DNN as a learned DNN 90 (step SB7). The learned DNN is stored in the memory 13 of the medical data processing apparatus 1, together with the type and number of auxiliary input images. Specifically, the type represents the type of imaging condition different from the imaging condition of the main input image, from among the imaging conditions of the auxiliary input image. In the example of the DNN in FIG. 8, the type is "slice position", and the number is "1"; for the DNN of FIG. 9, the type is "frame", and the number is "1"; for the DNN of FIG. 10, the type is "slice position" and "frame", and the number is "2"; for the DNN of FIG. 11, the type is "k-space trajectory", and the number is "1"; for the DNN of FIG. 12, the type is "acquisition sequence", and the number is "1"; and for the DNN of FIG. 13, the type is "acquisition sequence", and the number is "2".

The model learning process of the model learning apparatus 5 according to the present embodiment has been described. The above flow of the training process is described as an example, and the present embodiment is not limited thereto.

As described above, the model learning program 50 according to the present embodiment causes the model learning apparatus 5 to implement at least the forward-propagation function 511 and the update function 513. With the forward-propagation function 511, estimated output data is generated by applying the main input data and the auxiliary input data to a multilayer network, which includes an input layer to which main input data and auxiliary input data of the same subject and of different imaging conditions are entered, an output layer from which output data corresponding to the main input data is output, and at least one intermediate layer provided between the input layer and the output layer. The update function 513 updates the parameters of the multilayer network in such a manner that the estimated output data and the true output data are approximated.

With the above configuration, the model learning program 50 according to the present embodiment learns the parameters of the multilayer network by using not only the main input data but also the auxiliary input data as input data in order to output the output data in which the data deficit portion of the main input data is restored. In this manner, the model learning program 50 according to the present embodiment can incorporate more information that is not included in the main input data in the training of parameters. This improves the restoration accuracy of the medical data by the learned model 90, as compared to the case of using only main input data as input data.

As described above, the medical data processing apparatus 1 according to the present embodiment includes a memory 13 and a processing circuitry 11. The memory 13 stores the learned model 90. The learned model 90 includes an input layer to which main input data and auxiliary input data of the same subject and of different imaging conditions are entered, an output layer from which output data corresponding to the main input data is output, and at least one intermediate layer provided between the input layer and the output layer. The processing circuitry 11 applies the learned model to the target input data relating to the subject and the auxiliary input data relating to the same subject and an imaging condition different from the target input data, and thereby generates the target output data relating to the subject.

With the above configuration, the medical data processing apparatus 1 can compensate for the missing portion of the target input data with the auxiliary input data, and therefore the restoration accuracy of the medical data by the learned model 90 can be enhanced as compared to the case of using only the target input data as input data.

The model learning program 50 stored in the memory 53 of the model learning apparatus 5 may be stored in the memory 13 of the medical data processing apparatus 1. That is, the training functions of the model learning apparatus 5, namely the forward-propagation function 511, the back-propagation function 512, the update function 513, the determination function 514, and the display control function 515, may be realized by the processing circuitry 11 of the medical data processing apparatus 1.

APPLICATION EXAMPLES

In the above description, the timing of generating the auxiliary input image is not particularly defined. In the following application examples, a plurality of medical images are sequentially generated in a single examination, and a process target medical image and an auxiliary input image are sequentially selected from the generated medical images. It is assumed here that a reconstruction process is executed for the restoration of medical image data from raw data. In this description, structural elements having the same or similar functions will be denoted by the same reference symbols, and a repetitive description will be given only where necessary.

Application Example 1

Magnetic Resonance Imaging Examination

A magnetic resonance imaging examination is conducted by a magnetic resonance imaging apparatus. In application example 1, the medical imaging apparatus 3 is an MR table of the magnetic resonance imaging apparatus.

Figure 17:
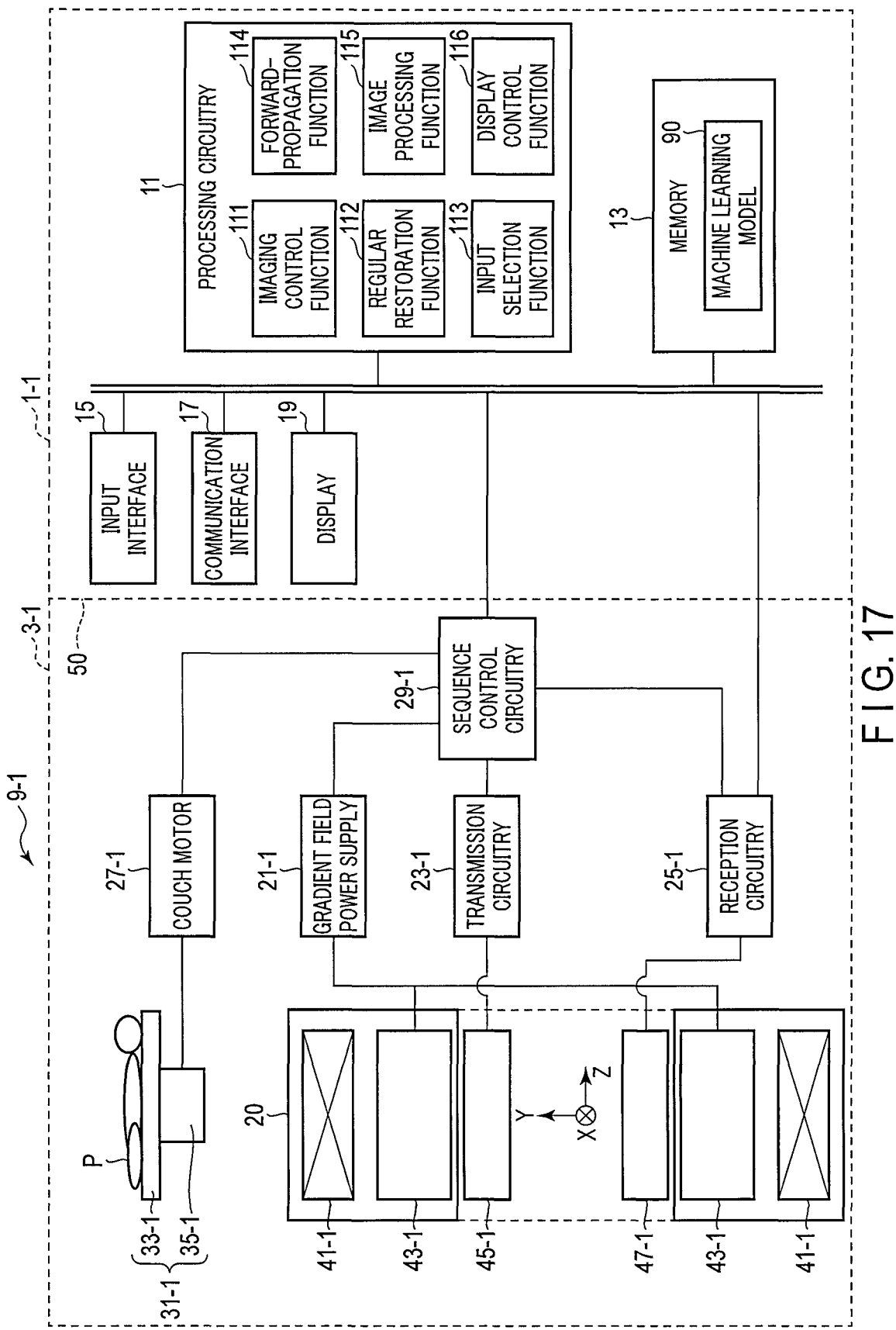
FIG. 17 is a diagram showing the configuration of a magnetic resonance imaging apparatus according to application example 1.

FIG. 17 is a diagram showing the configuration of a magnetic resonance imaging apparatus 9-1 according to application example 1. As shown in FIG. 17, the magnetic resonance imaging apparatus 9-1 includes a base 20-1, a table 31-1, a gradient field power supply 21-1, a transmission circuitry 23-1, a reception circuitry 25-1, a couch motor 27-1, a sequence control circuitry 29-1 and a medical data processing apparatus 1-1.

The base 20-1 has a static field magnet 41-1 and a gradient field coil 43-1. The static field magnet 41-1 and the gradient field coil 43-1 are housed in the housing of the base 20-1. A hollowed bore is formed in the housing of the base 20-1. A transmission coil 45-1 and a reception coil 47-1 are arranged in the bore of the base 20-1.

The static field magnet 41-1 is shaped basically into a hollowed cylinder, and generates a static magnetic field in the approximately cylindrical interior. As the static field magnet 41-1, a permanent magnet, a superconducting magnet, a normal conducting magnet or the like may be used. The central axis of the static field magnet 41-1 is defined as the Z axis, the axis orthogonal to the Z axis in a vertical manner is defined as the Y axis, and the axis orthogonal to the Z axis in a horizontal manner is defined as the X axis. The X, Y and Z axes constitute an orthogonal three dimensional coordinate system.

The gradient field coil 43-1 is a coil unit attached to the inside of the static field magnet 41-1 and shaped basically into a hollowed cylinder. The gradient field coil 43-1 receives a current from the gradient field power supply 21-1 and generates a gradient magnetic field. Specifically, the gradient field coil 43-1 has three coils corresponding to the X, Y, and Z axes that are orthogonal to one another. Each of the three coils forms a gradient magnetic field having a magnetic field strength that varies along the respective one of the X, Y, and Z axes. The gradient magnetic fields along the X, Y, and Z axes are combined to form a slice selection gradient magnetic field Gs, a phase encode gradient magnetic field Gp, and a frequency encode gradient magnetic field Gr in the desired directions that are orthogonal to one another. The slice selection gradient magnetic field Gs is used for determining a suitable imaging unit. The phase encode gradient magnetic field Gp is used for changing the phase of the MR signal in accordance with the spatial position. The frequency encode gradient magnetic field Gr is used for changing the frequency of the MR signal in accordance with the spatial position. In the following description, it is assumed that the gradient direction of the slice selection gradient magnetic field Gs is along the Z axis, the gradient direction of the phase encode gradient magnetic field Gp is along the Y axis, and the gradient direction of the frequency encode gradient magnetic field Gr is along the X axis.

The gradient field power supply 21-1 supplies a current to the gradient field coil 43-1 in accordance with the sequence control signal from the sequence control circuitry 29-1. With the gradient field power supply 21-1 supplying a current to the gradient field coil 43-1, the gradient field coil 43-1 generates a gradient magnetic field along each of the X, Y and Z axes. This gradient magnetic field is superimposed on the static magnetic field formed by the static field magnet 41-1, and applied to the subject P.

The transmission coil 45-1 is arranged, for example, inside the gradient field coil 43-1, receives a current supply from the transmission circuitry 23-1, and generates a radio frequency magnetic field pulse (hereinafter referred to as RF magnetic field pulse).

The transmission circuitry 23-1 supplies a current to the transmission coil 45-1 in order to apply to the subject P an RF magnetic field pulse for excitation of the target protons within the subject P via the transmission coil 45-1. The RF magnetic field pulse vibrates at the resonance frequency specific to the target protons so as to excite the target protons. From the excited target protons, a magnetic resonance signal (hereinafter referred to as an MR signal) is generated and detected by the reception coil 47-1. The transmission coil 45-1 may be a whole-body coil (WB coil). The whole-body coil may be used as a transmission/reception coil.

The reception coil 47-1 receives an MR signal produced from the target protons within the subject P by the action of the RF magnetic field pulse. The reception coil 47-1 has a plurality of reception coil elements for receiving MR signals. The received MR signal is supplied to the reception circuitry 25-1 in a wired or wireless manner. The reception coil 47-1 has a plurality of reception channels that are provided in parallel, although they are not shown in FIG. 1. A reception channel includes a reception coil element for receiving the MR signal, an amplifier for amplifying the MR signal, and the like. The MR signal is output for each reception channel. The total number of reception channels may be the same as the total number of reception coil elements. Alternatively, the total number of reception channels may be larger or smaller than the total number of reception coil elements.

The reception circuitry 25-1 receives the MR signal generated from the excited target protons by way of the reception coil 47-1. The reception circuitry 25-1 processes the received MR signal to generate a digital MR signal. The digital MR signal can be expressed by the k-space that is defined by the spatial frequency. Thus, the digital MR signal will be referred to as k-space data. The k-space data is a type of raw data that is subjected to the image reconstruction. The k-space data is supplied to the signal data processing device 50-1 in a wired or wireless manner.

The transmission coil 45-1 and the reception coil 47-1 are described merely as examples. In place of the transmission coil 45-1 and the reception coil 47-1, a transmission/reception coil having a transmission function and a reception function may be adopted. Alternatively, the transmission coil 45-1, the reception coil 47-1 and a transmission/reception coil may be combined.

A table 31-1 is installed adjacent to the base 20-1. The table 31-1 has a table top 33-1 and a base 35-1. The subject P is placed on the table top 33-1. The base 35-1 supports the table top 33-1 in a slidable manner along the X, Y, and Z axes. A couch motor 27-1 is accommodated in the base 35-1. The couch motor 27-1 moves the table top 33-1 under the control of the sequence control circuitry 29-1. The couch motor 27-1 may include, for example, any motor such as a servomotor and a stepping motor.

The sequence control circuitry 29-1 includes, as hardware resources, a processor such as a CPU or MPU, and a memory such as a ROM or RAM. The sequence control circuitry 29-1 synchronously controls the gradient field power supply 21-1, the transmission circuitry 23-1 and the reception circuitry 25-1, based on the imaging protocol determined by the imaging control function 111 of the processing circuitry 11, conducts MR imaging on the subject P by executing a pulse sequence in accordance with the imaging protocol, and acquires k-space data of the subject P.

As shown in FIG. 17, the medical data processing apparatus 1-1 is a computer including a processing circuitry 11, a memory 13, an input interface 15, a communication interface 17 and a display 19. Since the medical data processing apparatus 1-1 is similar to the above-mentioned medical data processing apparatus 1, the explanation is omitted.

FIG. 18 is a schematic diagram showing the process of the medical data processing apparatus 1-1 according to application example 1. In the examination of FIG. 18, the EPI acquisition with value b=0 is first conducted (step SP1). At step SP1, the processing circuitry 11 first implements the imaging control function 111 to cause the model imaging apparatus (gantry of the magnetic resonance imaging apparatus) 3 to conduct the EPI acquisition with value b=0. At step SP1, which is the first stage of the examination, full sampling of the k-space data is performed. Full sampling is to acquire k-space data for all the acquisition lines of the k-space. After k-space data is acquired, the processing circuitry 11 implements the regular restoration function 112. With the regular restoration function 112, the processing circuitry 11 performs fast Fourier transform (FFT) on the k-space data acquired at step SP1 to generate an FFT reconstruction image with value b=0.

After step SP1, the processing circuitry 11 implements the imaging control function 111 to cause the gantry 20 to perform the EPI acquisition with value b=500 (step SP2). At step SP2, sparse sampling of the k-space data is performed. Sparse sampling is to acquire k-space data only for some of the acquisition lines of the k-space. Sparse sampling is performed, for example, by parallel imaging, half-Fourier method, compressed sensing, and the like. The sparse sampling can reduce the time period for imaging. At steps SP2 and SP1, the imaging body parts or slice positions are the same. Once the k-space data is acquired, the processing circuitry 11 implements the regular restoration function 112. With the regular restoration function 112, the processing circuitry 11 performs FFT on the k-space data acquired at step SP2 to generate an FFT reconstruction image with value b=500. The FFT reconstruction image obtained at step SP2 may be degraded in image quality, which is caused by an increase in value b and sparse sampling.

When an FFT reconstruction image with value b=500 is generated, the processing circuitry 11 implements the input selection function 113. As shown in FIG. 18, with the input selection function 113, the processing circuitry 11 selects as an auxiliary input image an FFT reconstruction image with value b=0 by full sampling, and selects as a target input image an FFT reconstruction image with value b=500 by sparse sampling. From the target input image, which is an image based on sparse sampling, its data is thinned in comparison to the auxiliary input image based on full sampling.

Thereafter, the processing circuitry 11 implements the forward-propagation function 114. With the forward-propagation function 114, the processing circuitry 11 first reads from the memory 13 a learned DNN (for b=500) in which an FFT reconstruction image with value b=500 by sparse sampling is a target output image, an FFT reconstruction image with value b=0 by full sampling is an auxiliary input image, and a DNN reconstruction image with value b=500 is a target input image. Next, the processing circuitry 11 enters an FFT reconstruction image with value b=500 by sparse sampling into the process target area 921 of the input layer 91 of the learned DNN (for b=500) that has been read out, and enters an FFT reconstruction image with value b=0 by full sampling into the auxiliary area 922. Then, the processing circuitry 11 performs the forward propagation on the FFT reconstruction image with value b=500 by sparse sampling and the FFT reconstruction image with value b=0 by full sampling, in the learned DNN (for b=500). As a result, a DNN reconstruction image with value b=500 is generated, in which image quality degradation incurred by the increased value b and sparse sampling is reduced.

After step SP2, the processing circuitry 11 implements the imaging control function 111 to perform the T1W acquisition in the gantry 20 (step SP3). At step SP3, sparse sampling of the k-space data is performed again for the reduction of the imaging time period. At steps SP3 and SP1, the imaging body parts or slice positions are the same. Once the k-space data is acquired, the processing circuitry 11 implements the regular restoration function 112. With the regular restoration function 112, the processing circuitry 11 performs FFT on the k-space data acquired at step SP3 to generate a T1W image. The image quality of the generated T1W image, which has been reconstructed from the sparsely sampled k-space data, is degraded.

When an FFT reconstruction T1W image is generated, the processing circuitry 11 implements the input selection function 113. As shown in FIG. 18, with the input selection function 113, the processing circuitry 11 selects an FFT reconstruction image with value b=0 by full sampling as an auxiliary input image, and an FFT reconstruction T1W image by sparse sampling as a target input image.

Thereafter, the processing circuitry 11 implements the forward-propagation function 114. With the forward-propagation function 114, the processing circuitry 11 first reads from the memory 13 a learned DNN (for T1W) in which an FFT reconstruction T1W image by sparse sampling is a target input image, an FFT reconstruction image with value b=0 by full sampling is an auxiliary input image, and a DNN reconstruction T1W image is a target output image. Next, the processing circuitry 11 enters an FFT reconstruction T1W image by sparse sampling to the process target area 921 of the input layer 91 of the learned DNN (for T1W) and an FFT reconstruction image with value b=0 by full sampling to the auxiliary area 922. Then, the processing circuitry 11 performs the forward propagation on the FFT reconstruction T1W image by sparse sampling and the FFT reconstruction image with value b=0 by full sampling, in the learned DNN (for T1W). As a result, a DNN reconstruction T1W image in which image quality degradation caused by sparse sampling is reduced can be generated.

According to application example 1, a target input image and an auxiliary input image are selected from a set of MR images acquired by executing a magnetic resonance imaging examination, as described above. Specifically, full sampling is performed at the first step of the examination, and sparse sampling is performed at the second and subsequent steps. A forward propagation in a learned DNN is performed, in which an MR image based on full sampling serves as an auxiliary input image and an MR image based on sparse sampling serves as a target input image. In this manner, a high definition MR image can be generated and displayed by sparse sampling while reducing the examination time period. Moreover, since a high-quality MR image can be generated even from sparse sampling, the undersampling rate of k-space data can be further increased, and the examination time period can be further reduced. In addition, according to application example 1, image quality degradation due to imaging with a relatively large value b, or any other image quality degradation specific to different acquisition sequences, can also be reduced by the learned DNN using two data inputs, namely the main input data and auxiliary input data.

Next, the application of magnetic resonance imaging to dynamic imaging will be explained. In magnetic resonance imaging, dynamic imaging can be realized by any kind of k-space trajectory. In the following example, dynamic imaging based on radial scanning, which offers relatively high temporal resolution, is adopted. The MR image may be a two-dimensional image or a three-dimensional image. For example, as dynamic imaging of three-dimensional images based on radial scanning, three-dimensional radial scanning and stack-of-stars may be adopted.

The processing circuitry 11 implements the imaging control function 111 to control the sequence control circuitry 29-1 to execute dynamic imaging on the subject P. In the dynamic imaging, the processing circuitry 11 acquires the k-space data of time-series frames. By implementing the regular restoration function 112, the processing circuitry 11 instantaneously generates MR images of the time-series frames based on the k-space data of the time-series frames. Any method can be adopted for the reconstruction of an MR image. However, in order to enhance the immediacy of MR image generation, a reconstruction method with a short processing time period should be adopted. As such a reconstruction method, the reconstruction method using the Jackson method, the gridding method, or AUTOMAP (Bo Zhu et al., Nature, 22 Mar. 2018, doi: 10.1038/nature 25988) may be adopted. In radial scanning, sample positions are unequally spaced in the k-space data. The processing circuitry 11 reconstructs the non-uniformly spaced k-space data to unequally spaced k-space data by the Jackson method. The processing circuitry 11 then applies the FFT to the equally spaced k-space data to generate an MR image.

By implementing the input selection function 113, the processing circuitry 11 selects a target input image and an auxiliary input image from the MR images of the time-series frames. The k-space data or MR images of time-series frames have common parameters that are the slice position and the type of k-space trajectory (radial scanning) and temporal resolution, and the individual parameter that is the acquisition time or frame. For example, the processing circuitry 11 selects, as the target input image, the MR image of the latest frame, and selects, as the auxiliary input image, the MR image of a frame located a predetermined number of frames before the latest frame. With regard to the predetermined number of frames, the frame is not particularly limited, and may be one frame before the latest frame, or two or more frames before.

By implementing the forward-propagation function 114, the processing circuitry 11 enters the selected target input image (MR image of the latest frame) and auxiliary input image (MR image of the previous frame) to the learned DNN 90 for image denoising, and instantaneously outputs a target output image (DNN reconstruction image of the latest frame). By implementing the display control function 116, the DNN reconstruction image of the latest frame is displayed on the display 19. Every time an MR image of the latest frame is generated, the processing circuitry 11 implements the input selection function 113 and the forward-propagation function 114 to generate the DNN reconstruction image of the latest frame, and implements the display control function 116 to display the DNN reconstruction image on the display 19. In this manner, the DNN reconstruction image can also be instantaneously displayed as a moving image.

The processing circuitry 11 has been described as using the learned DNN 90 for image denoising, but the learned DNN 90 for k-space data denoising may be used. If this is the case, the processing circuitry 11 implements the input selection function 113 to select a target input k-space data and an auxiliary input k-space data from the k-space data of time-series frames. By implementing the forward-propagation function 114, the processing circuitry 11 enters the selected target input k-space data (k-space data of the latest frame) and the auxiliary input k-space data (k-space data of a previous frame) to the learned DNN 90 for k-space data denoising, and instantaneously outputs the target output k-space data (DNN k-space data of the latest frame). Thereafter, the processing circuitry 11 implements the regular restoration function 112 to perform FFT or the like on the DNN k-space data of the latest frame and generate a DNN reconstruction image, and implements the display control function 116 to instantaneously display the DNN reconstruction image.

Application Example 2

X-Ray Computer Tomography Examination

An X-ray computed tomography imaging apparatus examination is performed by an X-ray computed tomography imaging apparatus. In application example 2, the medical imaging apparatus 3 is a CT gantry of the X-ray computed tomography imaging apparatus.

FIG. 19 is a diagram showing the configuration of an X-ray computed tomography imaging apparatus 9-2. For convenience of explanation, multiple CT gantries 3-2 are described in FIG. 19, but the X-ray computed tomography imaging apparatus 9-2 is generally equipped with one gantry 3-2.

As shown in FIG. 19, the X-ray computed tomography imaging apparatus 9-2 includes a gantry 3-2, a table 30-2, and a medical data processing apparatus (console) 1-2. The gantry 3-2 is a scanning device configured to execute X-ray CT imaging on the subject P. The table 30-2 is a carrying device for placing the subject P to be subjected to the X-ray CT imaging and for positioning the subject P. The medical data processing apparatus 1-2 is a computer that controls the gantry 3-2. The gantry 3-2 and the table 30-2 may be installed in an examination room, and the medical data processing apparatus 1-2 may be installed in a control room adjacent to the examination room. The gantry 3-2, the table 30-2, and the medical data processing apparatus 1-2 are communicably connected with each other in a wired or wireless manner.

As shown in FIG. 19, the gantry 3-2 includes an X-ray tube 21-2, an X-ray detector 12-2, a rotation frame 23-2, an X-ray high voltage device 24-2, a controller 25-2, a wedge filter 26-2, a collimator 27-2 and a data acquisition circuitry data acquisition system (DAS) 28-2.

The X-ray tube 21-2 generates X-rays. Specifically, the X-ray tube 21-2 includes a cathode for generating thermoelectrons, an anode for generating X-rays upon receipt of the thermoelectrons flying out of the cathode, and a vacuum tube for holding the cathode and anode. The X-ray tube 21-2 is connected to the X-ray high voltage device 24-2 via a high-voltage cable. A filament current is supplied to the cathode by the X-ray high voltage device 24-2. Upon receipt of the filament current supplied, thermoelectrons are generated from the cathode. A tube voltage is applied between the cathode and the anode by the X-ray high voltage device 24-2. Upon application of the tube voltage, thermoelectrons fly from the cathode to the anode and collide with the anode, thereby generating X-rays. The generated X-rays are irradiated on the subject P. With thermoelectrons flying from the cathode to the anode, a tube current flows.

The X-ray detector 22-2 detects X-rays generated from the X-ray tube 21-2 and having passed through the subject P, and supplies an electric signal corresponding to the detected X-ray dose to the DAS 28-2. The X-ray detector 22-2 has a structure in which a plurality of X-ray detection element arrays are aligned in a slice direction (column direction), and a plurality of X-ray detection elements are aligned in the channel direction in each of the X-ray detection element arrays. The X-ray detector 22-2 is, for example, an indirect conversion-type detector having a grid, a scintillator array and a photosensor array. The scintillator array includes a plurality of scintillators. The scintillators output an amount of light corresponding to the incident amount of X-rays. The grid is disposed on the X-ray incident surface side of the scintillator array, and has an X-ray shielding plate that absorbs the scattered X-rays. The grid may also be referred to as a collimator (one-dimensional collimator or two-dimensional collimator). The photosensor array converts the light from the scintillator into an electric signal corresponding to the amount of light. As the photosensor, a photodiode may be adopted.

The rotation frame 23-2 is an annular frame that supports the X-ray tube 21-2 and the X-ray detector 22-2 in a rotatable manner around the rotation axis Z. Specifically, the rotation frame 23-2 supports the X-ray tube 21-2 and the X-ray detector 22-2 so as to face each other. The rotation frame 23-2 is supported on a fixed frame (not shown) in a rotatable manner around the rotation axis Z. By the controller 25-2 rotating the rotation frame 23-2 around the rotation axis Z, the X-ray tube 21-2 and the X-ray detector 22-2 are rotated around the rotation axis Z. The field of view (FOV) is defined in the opening 29-2 of the rotation frame 23-2.

In the present embodiment, the rotation axis of the rotation frame 23-2 in the non-tilted state or the longitudinal direction of the table top 33-2 of the table 30-2 is defined as the Z direction, the direction orthogonal to the Z direction and horizontal to the floor surface is defined as the X direction, and a direction orthogonal to the Z direction and perpendicular to the floor surface is defined as the Y direction.

The X-ray high voltage device 24-2 includes a high-voltage generator and an X-ray controller. The high-voltage generator has electric circuits such as a transformer and a rectifier, and generates a high voltage to be applied to the X-ray tube 21-2 and a filament current to be supplied to the X-ray tube 21-2. The X-ray controller controls the high voltage applied to the X-ray tube 21-2 and the filament current supplied to the X-ray tube 21-2. The high-voltage generator may be of a transformer type or an inverter type. The X-ray high voltage device 24-2 may be provided in the rotation frame 23-2 of the gantry 3-2, or may be provided in the fixed frame (not shown) of the gantry 3-2.

The wedge filter 26-2 adjusts the dose of X-rays applied to the subject P. Specifically, the wedge filter 26-2 attenuates the X-rays so that the dose of X-rays emitted from the X-ray tube 21-2 to the subject P can be distributed as predetermined. As the wedge filter 26-2, a metal filter formed by processing a metal such as aluminum may be adopted. The wedge filter 26-2 is processed to have a predetermined target angle and a predetermined thickness. The wedge filter 26-2 may also be referred to as a bow-tie filter.

The collimator 27-2 restricts the irradiation range of the X-rays passed through the wedge filter 26-2. The collimator 27-2 slidably supports a plurality of lead plates that shield the X-rays, and adjusts the form of the slit that is formed by the lead plates. The collimator 27-2 may also be referred to as an X-ray diaphragm.

The DAS 28-2 reads from the X-ray detector 22-2 an electric signal corresponding to the dose of X-rays detected by the X-ray detector 22-2, amplifies the read-out electric signal, and integrates the electric signal over the viewing period, thereby acquiring the detection data having a digital value corresponding to the dose of X-rays over the viewing period. The detection data may also be referred to as projection data. The DAS 28-2 may be realized by an ASIC with circuitry elements capable of generating projection data. The projection data (detection data) generated by the DAS 28-2 is sent, by optical communication, from the transmitter provided in the rotation frame 23-2 and having a light emitting diode (LED) to the receiver provided in the non-rotating unit (e.g., fixed frame) of the gantry 3-2, and is transmitted from the receiver to the medical data processing apparatus 1-2. The transmission system of the projection data from the rotation frame 23-2 to the non-rotating unit of the gantry 3-2 is not limited to the aforementioned optical communication, and any non-contact data transmission method may be adopted.

The table 30-2 includes a base 35-2 and a table top 33-2. The base 35-2 is installed on the floor. The base 35-2 is a structure that supports the support frame so as to be movable in a direction (Y direction) perpendicular to the floor surface. The support frame is a frame provided on the base 35-2. The support frame supports the table top 33-2 in a slidable manner along the central axis Z. The table top 33-2 is a plate-like structure having flexibility, on which the subject P is placed. The couch motor is accommodated in the table 30-2. The couch motor is a motor or actuator that generates power to move the table top 33-2 carrying the subject P thereon. The couch motor may operate in accordance with the control by the controller 25-2, the medical data processing apparatus 1-2 or the like.

The controller 25-2 controls the X-ray high voltage device 24-2, the DAS 28-2 and the table 30-2 to execute the X-ray CT imaging in accordance with the imaging control function 111 of the processing circuitry 11. The controller 25-2 includes a processing circuitry having a CPU and the like, and a driving device such as a motor or an actuator. The processing circuitry includes a processor such as a CPU and a memory such as a ROM and a RAM as hardware resources. The controller 25-2 controls the gantry 3-2 and the table 30-2 in accordance with the operation signals from the input interface 15 provided in the medical data processing apparatus 1-2, the gantry 3-2, and the table 30-2. The controller 25-2 may control the rotation of the rotation frame 23-2, the tilt of the gantry 3-2, the movements of the table top 33-2 and the table 30-2.

The medical data processing apparatus (console) 1-2 is a computer having a processing circuitry 11, a memory 13, an input interface 15, a communication interface 17 and a display 19. The medical data processing apparatus 1-2 is equivalent to the above-mentioned medical data processing apparatus 1, and therefore the explanation thereof is omitted.

FIG. 20 is a schematic diagram showing the process of the medical data processing apparatus 1-2 according to application example 2. The examination shown in FIG. 20 is time-series imaging, in which X-ray CT imaging is repeated over a plurality of rotations. In the first rotation, the X-ray CT imaging is performed with a high dose of X-rays (step SQ1). The processing circuitry 11 performs FBP on the projection data acquired at step SQ1 to generate an FBP reconstruction image for the first rotation.

As shown in FIG. 20, X-ray CT imaging with a low dose of X-rays is repeated for the second and subsequent rotations (steps SQ2 and SQ3). When the projection data of the second rotation is acquired, the processing circuitry 11 performs FBP on the projection data to generate an FBP reconstruction image for the second rotation. The low-dose X-ray CT imaging may be conducted by lowering the tube current with respect to the first rotation, by performing the intermittent X-ray irradiation, by rotating the rotation frame at high speed, or by combining any of the above low tube current, intermittent X-ray exposure and fast rotation. Since FBP reconstruction images of the second and subsequent rotations are acquired by low-dose X-ray CT imaging, they are subject to image quality degradation in comparison to the FBP reconstruction image of the first rotation.

When the FBP reconstruction image for the second rotation is generated, the processing circuitry 11 implements the input selection function 113. With the input selection function 113, the processing circuitry 11 selects the high-dose FBP reconstruction image for the first rotation as an auxiliary input image, and the low-dose FBP reconstruction image for the second rotation as a target input image, as shown in FIG. 20.

Thereafter, the processing circuitry 11 implements the forward-propagation function 114. With the forward-propagation function 114, the processing circuitry 11 first reads from the memory 13 the learned DNN (for low dose) in which a low dose FBP reconstruction image is a target input image, a high dose FBP reconstruction image is an auxiliary input image, and a high quality FBP reconstruction image is a target output. Next, the processing circuitry 11 enters the low dose FBP reconstruction image of the second rotation into the process target area 921 of the input layer 91 of the learned DNN (for low dose), and the high dose FBP reconstruction image of the first rotation into the auxiliary area 922. Then, the processing circuitry 11 performs the forward propagation on the low dose FBP reconstruction image of the second rotation and the high dose FBP reconstruction image of the first rotation in the learned DNN (for low dose). In this manner, a DNN reconstruction image of the second rotation can be generated, with the low dose-related image quality degradation being reduced.

Similarly, when the projection data is acquired for the third rotation, the processing circuitry 11 performs the FBP to this projection data to generate an FBP reconstruction image for the third rotation. Next, the processing circuitry 11 implements the input selection function 113. As shown in FIG. 20, the processing circuitry 11 selects, with the input selection function 113, the high-dose FBP reconstruction image for the first rotation as an auxiliary input image, and the low-dose FBP reconstruction image for the third rotation as a target input image.

Thereafter, the processing circuitry 11 implements the forward-propagation function 114. With the forward-propagation function 114, the processing circuitry 11 enters the low dose FBP reconstruction image of the third rotation into the process target area 921 of the input layer 91 of the learned DNN, and the high dose FBP reconstruction image of the first rotation into the auxiliary area 922 of the input layer 91 of the learned DNN. Then, the processing circuitry 11 performs the forward propagation on the low dose FBP reconstruction image of the third rotation and the high dose FBP reconstruction image of the first rotation in the learned DNN. In this manner, a DNN reconstruction image of the third rotation can be generated, with low dose-related degradation of image quality being reduced.

As described above, according to application example 2, a target input image and an auxiliary input image are selected from a set of CT images acquired by executing an X-ray computer tomography examination. In particular, high dose X-ray CT imaging is conducted in the first rotation, and low dose X-ray CT imaging is conducted in the second and subsequent rotations. The forward propagation of the learned DNN is performed with a high dose CT image as an auxiliary input image and a low dose CT image as a target input image. In this manner, a CT image less affected by image quality degradation due to the low dose can be generated and displayed, while the exposure dose is reduced. In addition, high-quality CT images can be generated from low dose X-ray CT imaging, and therefore the X-ray dose can be further reduced.

Application Example 3

PET/CT Examination

A PET/CT examination is conducted by a PET/CT apparatus. In application example 3, the medical imaging apparatus 3 is the gantry of the PET/CT apparatus. Such a medical imaging apparatus 3 is equipped with a CT gantry for X-ray CT imaging and a PET gantry for PET imaging.

Figure 21:
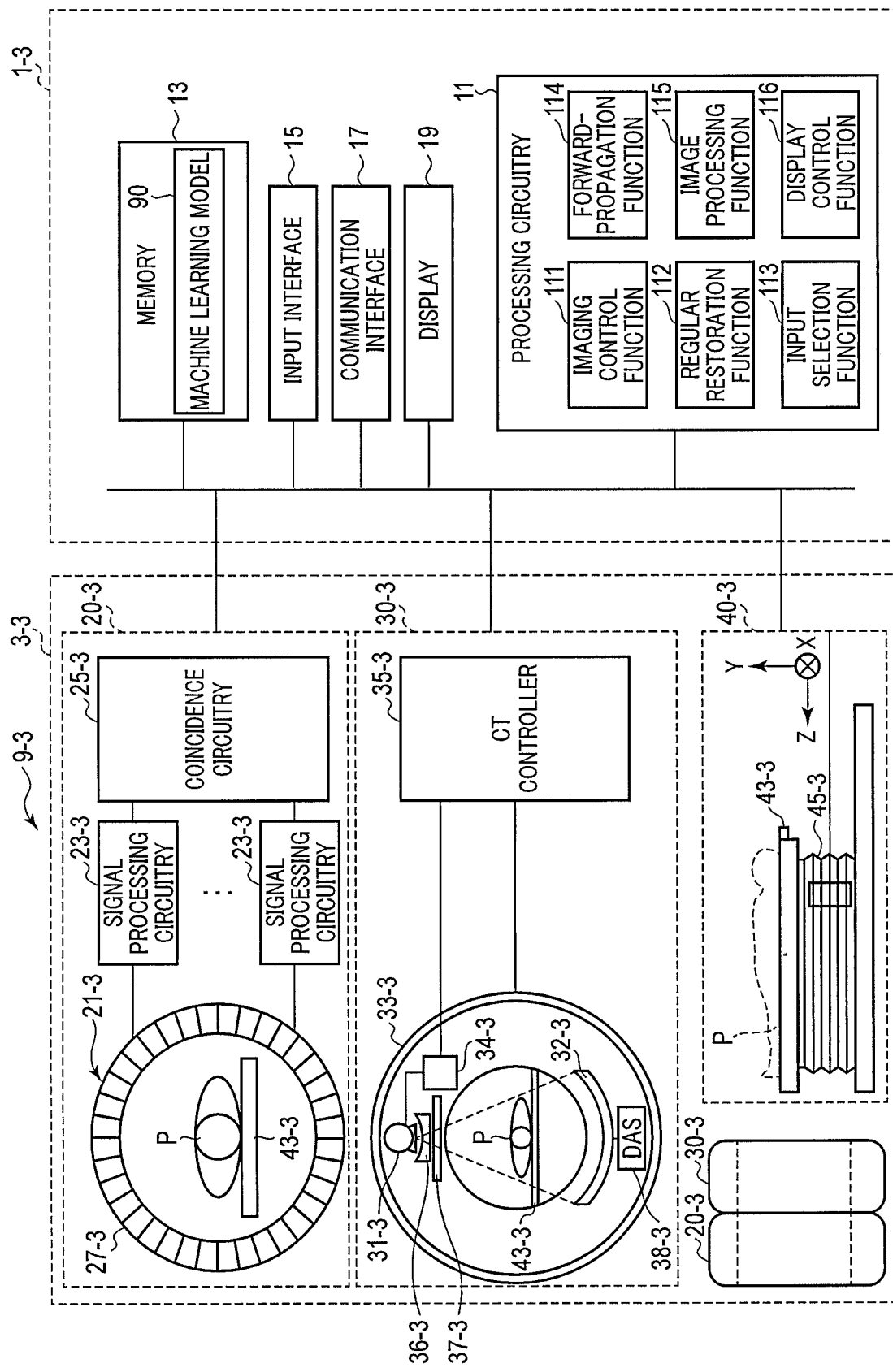
FIG. 21 is a diagram showing the configuration of a PET/CT apparatus according to application example 3.

FIG. 21 is a diagram showing the configuration of the PET/CT apparatus 9-3. As shown in FIG. 21, the PET/CT apparatus 9-3 includes a PET gantry 20-3, a CT gantry 30-3, a table 40-3 and a medical data processing apparatus 1-3. In general, the PET gantry 20-3, CT gantry 30-3 and table 40-3 are installed in the examination room, and the medical data processing apparatus 1-3 is installed in a control room adjacent to the examination room. The PET gantry 20-3 is an image pickup apparatus that performs PET imaging on the subject P. The CT gantry 30-3 is an image pickup device that performs X-ray CT imaging on the subject P. The table 40-3 movably supports a table top 43-3 on which the subject P of the imaging target is placed. The medical data processing apparatus 1-3 is a computer that controls the PET gantry 10, CT gantry 30 and table 50.

As shown in FIG. 21, the PET gantry 20-3 includes a detector ring 21-3, a signal processing circuitry 23-3, and a coincidence circuitry 25-3.

The detector ring 21-3 has a plurality of gamma-ray detectors 27-3 arranged on the periphery around the central axis Z. A field of view (FOV) is defined in the opening of the detector ring 21-3. The subject P is positioned so that the imaging body part of the subject P can fall within the image field of view. A medicine labeled with a positron emitting radionuclide is given to the subject P. The positrons emitted from the positron emitting nuclide collide with the surrounding electrons, generating a pair of annihilation gamma rays. The gamma-ray detectors 27-3 detect the annihilation gamma rays emitted from the body of the subject P, and generate an electric signal corresponding to the detected light amount of the annihilation gamma rays. For example, a gamma-ray detector 27-3 may include a plurality of scintillators and a plurality of photomultiplier tubes. The scintillators receive the annihilation gamma rays based on the radioactive isotope in the subject P to generate light. The photomultiplier tubes generate an electric signal corresponding to the amount of light. The generated electric signal is supplied to the signal processing circuitry 23-3.

Based on the electric signals from the gamma-ray detectors 27-3, the signal processing circuitry 23-3 generates single event data. Specifically, the signal processing circuitry 23-3 performs a detection time measurement process, position calculation process, and energy calculation process. The signal processing circuitry 23-3 is realized by a processor configured to execute the detection time measurement process, position calculation process, and energy calculation process.

In the detection time measurement process, the signal processing circuitry 23-3 measures the gamma ray detection time by the gamma-ray detectors 27-3. Specifically, the signal processing circuitry 23-3 monitors the peak value of the electric signal from the gamma-ray detectors 27-3, and measures the time at which the peak value exceeds a preset threshold value, as the detection time. In other words, the signal processing circuitry 23-3 electrically detects the annihilated gamma rays by detecting the peak value that exceeds the threshold value. In the position calculation process, the signal processing circuitry 23-3 calculates the incident positions of the annihilation gamma rays, based on the electric signals from the gamma-ray detectors 27-3. The incident positions of the annihilation gamma ray correspond to the position coordinates of the scintillators on which the annihilation gamma rays are incident. In the energy calculation process, the signal processing circuitry 23-3 calculates the energy value of the detected annihilation gamma rays, based on the electric signal from the gamma-ray detector 27. The detection time data, the position coordinate data, and the energy value data for a single event are associated with each other. The combination of the energy value data, position coordinate data and detection time data of a single event is referred to as single event data. Each time the annihilation gamma rays are detected, single event data is sequentially generated. The generated single event data is supplied to the coincidence circuitry 25-3.

The coincidence circuitry 25-3 performs a coincidence process on the single event data obtained from the signal processing circuitry 23-3. As a hardware resource, the coincidence circuitry 25-3 is realized by a processor configured to execute the coincidence process. In the coincidence process, the coincidence circuitry 25-3 repeatedly identifies the single event data for any two single events that fall within a predetermined time frame, from among the repetitively supplied single event data. This pair of single events can be regarded as being derived from the annihilation gamma rays generated from the same pair annihilation point. A pair of single events is collectively referred to as a simultaneous count event. The line connecting the pair of gamma-ray detectors 27-3 (scintillators, in particular) that have detected the pair annihilation gamma rays is referred to as a line of response (LOR). The event data relating to the pair of events that constitutes the LOR is referred to as simultaneous count event data. The simultaneous count event data and the single event data are transmitted to the medical data processing apparatus 1-3. When the simultaneous count event data and single event data do not have to be distinguished from each other, they will be referred to as PET event data.

In the above configuration, the signal processing circuitry 23-3 and the gantry 20-3, but the present invention is not limited thereto. For example, the coincidence circuitry 25-3 may be included, or both the signal processing circuitry 23-3 and the coincidence circuitry 25-3 may be included, in a device separately provided from the PET gantry 20-3. Furthermore, one coincidence circuitry 25-3 maybe provided for a plurality of signal processing circuits 23-3 mounted on the PET gantry 20-3. Alternatively, by dividing the signal processing circuits 23-3 mounted on the PET gantry 20-3 into a plurality of groups, each of the groups may be provided with one coincidence circuitry 25-3.

As shown in FIG. 21, the CT gantry 30-3 includes an X-ray tube 31-3, an X-ray detector 32-3, a rotation frame 33-3, an X-ray high voltage device 34-3, a CT controller 35-3, a wedge filter 36-3, a collimator 37-3, and a DAS 38-3.

The X-ray tube 31-3 generates X-rays. Specifically, the X-ray tube 31-3 includes a vacuum tube that contains a cathode for generating thermoelectrons and an anode for generating X-rays upon receipt of thermoelectrons flying out of the cathode. The X-ray tube 31-3 is connected to the X-ray high voltage device 34-3 via a high-voltage cable. A tube voltage is applied between the cathode and the anode by the X-ray high voltage device 34-3. Under the application of the tube voltage, thermoelectrons fly out of the cathode to the anode. With the thermoelectrons flying from the cathode to the anode, a tube current flows. By the application of a high voltage from the X-ray high voltage device 34-3 and the supply of the filament current, thermoelectrons are emitted from the cathode toward the anode, and the thermoelectrons collide with the anode, thereby generating X-rays.

The X-ray detector 32-3 detects the X-rays generated from the X-ray tube 31-3 and having passed through the subject P, and outputs electric signals corresponding to the dose of the detected X-rays, to the DAS 38-3. The X-ray detector 32-3 has a structure in which a plurality of X-ray detection element arrays are aligned in a slice direction (column direction or row direction), and a plurality of X-ray detection elements are aligned in each of the X-ray detection element arrays in the channel direction. The X-ray detector 32-3 maybe of an indirect conversion type, having a grid, a scintillator array and a photosensor array. The scintillator array includes a plurality of scintillators. The scintillators output an amount of light corresponding to the incident X-ray amount. The grid is provided on the X-ray incident surface side of the scintillator array, and has an X-ray shielding plate that absorbs the scattered X-rays. The photosensor array converts the light from the scintillator into an electric signal, corresponding to the amount of light. As the photosensor, a photodiode or a photomultiplier tube may be adopted. The X-ray detector 32-3 may be of a direct conversion type (semiconductor detector) having a semiconductor element for converting the incident X-rays into an electric signal.

The rotation frame 33-3 is an annular frame that supports the X-ray tube 31-3 and the X-ray detector 32-3 in a rotatable manner around the rotation axis Z. Specifically, the rotation frame 33-3 supports the X-ray tube 31-3 and the X-ray detector 32-3 in such a manner that they face each other. The rotation frame 33-3 is supported on a fixed frame (not shown) in a rotatable manner around the rotation axis Z. With the rotation frame 33-3 rotating around the rotation axis Z by the CT controller 35-3, the X-ray tube 31-3 and the X-ray detector 32-3 are rotated around the rotation axis Z. The rotation frame 33-3 rotates at a constant angular velocity around the rotation axis Z under the power from the drive mechanism of the CT controller 35-3. A field of view (FOV) is defined in the opening of the rotation frame 33-3.

In the present embodiment, the rotation axis of the rotation frame 33-3 in the non-tilted state or the longitudinal direction of the table top 43-3 of the table 40-3 is defined as the Z-axis direction, the axial direction that is orthogonal to the Z-axis direction and horizontal to the floor surface is defined as the X-axis direction, and the axial direction orthogonal to the Z-axis direction and perpendicular to the floor surface is defined as Y-axis direction.

The X-ray high voltage device 34-3 has electric circuits such as a transformer and a rectifier, and a high-voltage generator that generates a high voltage to be applied to the X-ray tube 31-3 and a filament current to be supplied to the X-ray tube 31-3, and an X-ray controller that controls the output voltage in accordance with the X-rays applied by the X-ray tube 31-3. The high-voltage generator may be of a transformer type or of an inverter type. The X-ray high voltage device 34-3 may be provided in the rotation frame 33-3 or in the fixed frame (not shown) of the CT gantry 30-3.

The wedge filter 36-3 adjusts the dose of X-rays applied to the subject P. Specifically, the wedge filter 36-3 attenuates the X-rays so that the dose of X-rays applied from the X-ray tube 31-3 to the subject P exhibits a preset distribution. As the wedge filter 36-3, a metal plate of aluminum or the like may be adopted. The wedge filter 36-3 may also be referred to as a bow-tie filter.

The collimator 37-3 restricts the irradiation range of the X-rays passed through the wedge filter 36-3. The collimator 37-3 slidably supports a plurality of lead plates shielding the X-rays, and adjusts the form of the slits formed by the plurality of lead plates.

The DAS 38-3 reads from the X-ray detector 32-3 an electric signal corresponding to the dose of X-rays detected by the X-ray detector 32-3, amplifies the read-out electric signal at a variable amplification ratio, and integrates the electric signal over the viewing period, thereby acquiring CT raw data having a digital value corresponding to the dose of X-rays over the viewing period. The DAS 38-3 is realized, for example, by an ASIC in which circuit elements capable of generating CT raw data are mounted. The CT raw data is transmitted to the medical data processing apparatus 1-3 via a non-contact data transmission device or the like.

The CT controller 35-3 controls the X-ray high voltage device 34-3 and the DAS 38-3 to execute X-ray CT imaging in accordance with the imaging control function 111 of the processing circuitry 11 of the medical data processing apparatus 1-3. The CT controller 35-3 has a processing circuitry having a CPU and the like, and a driving mechanism such as a motor or an actuator. The processing circuitry 11 includes, as hardware resources, a processor such as a CPU and MPU, and a memory such as a ROM and RAM.

Various types of CT gantries 30-3 are available, including a rotate/rotate type (third generation CT), in which an integrated unit of an X-ray generation unit and an X-ray detection unit rotates around the subject, and a stationary/rotate type (fourth generation CT), in which a plurality of X-ray generation elements arrayed in a ring shape are fixed so that only the X-ray generation unit rotates around the subject. Any type may be applicable to the embodiment.

As shown in FIG. 21, the table 40-3 carries the scan target subject P thereon and moves the carried subject. The table 40-3 is shared by the PET gantry 20-3 and the CT gantry 30-3.

The table 40-3 has a base 45-3 and a table top 43-3. The base 45-3 is installed on the floor. The base 45-3 is a housing that supports the support frame in a movable manner in a direction (Y-axis direction) perpendicular to the floor surface. The support frame is provided at the top of the base 45-3. The support frame supports the table top 43-3 in a slidable manner along the central axis Z. The table top 43-3 is a flexible plate on which the subject P is placed. The couch motor is accommodated in the housing of the table 40-3. The couch motor is a motor or actuator that generates power for moving the support frame and the table top 43-3 on which the subject P is placed. The couch motor may operate in accordance with the control by the medical data processing apparatus 1-3 or the like.

The PET gantry 20-3 and CT gantry 30-3 are arranged in such a manner that the central axis Z of the opening of the PET gantry 20-3 approximately coincides with the central axis Z of the opening of the CT gantry 30-3. The table 40-3 is arranged in such a manner that the longitudinal axis of the table top 43-3 extends in parallel to the central axis Z of the opening of the PET gantry 20-3 and CT gantry 30-3. The CT gantry 30-3 and PET gantry 20-3 are installed in this order with respect to the table 40-3.

The medical data processing apparatus (console) 1-3 is a computer having a processing circuitry 11, a memory 13, an input interface 15, a communication interface 17 and a display 19. The medical data processing apparatus 1-3 is equivalent to the medical data processing apparatus 1, and therefore the explanation thereof is omitted.

Figure 23:
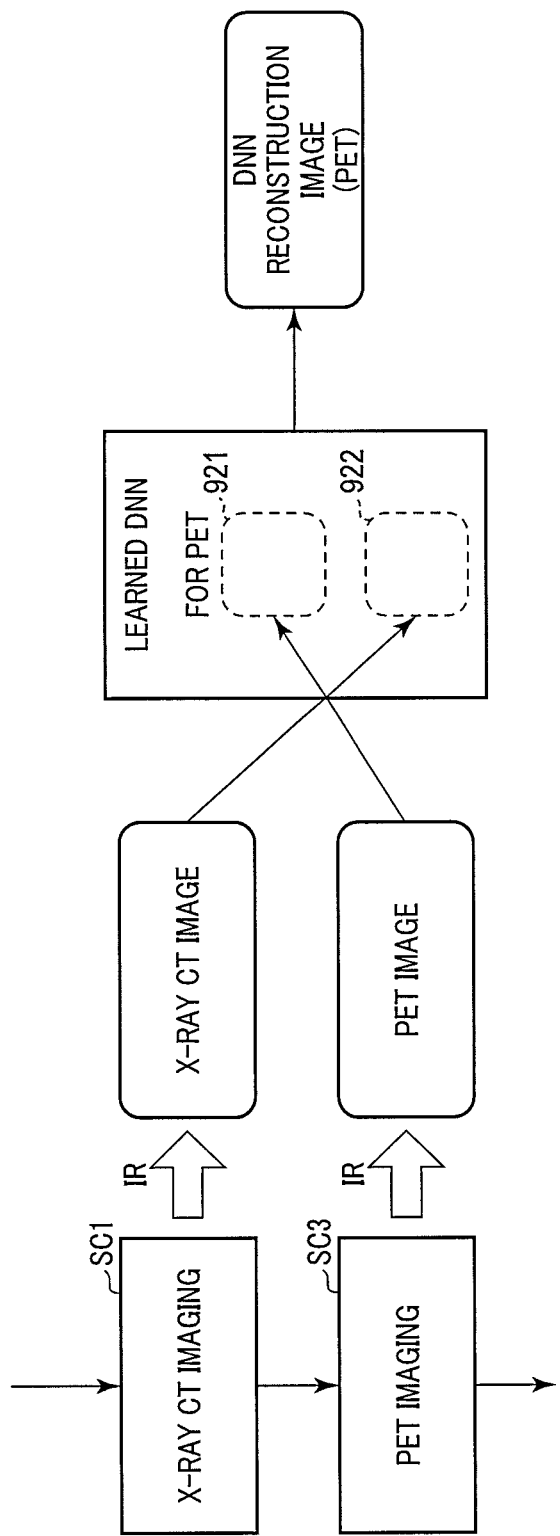
FIG. 23 is a schematic diagram showing the process of the medical data processing apparatus illustrated in FIG. 21.

FIG. 22 is a diagram showing a typical processing flow of the medical data processing apparatus 1 according to application example 3. FIG. 23 is a schematic diagram showing the process of the medical data processing apparatus 1 according to application example 3.

As shown in FIGS. 22 and 23, the processing circuitry 11 first executes the imaging control function 111 (step SC1). At step SC1, the processing circuitry 11 controls the medical imaging apparatus 3 to execute the X-ray CT imaging on the subject. The projection data on the subject acquired by the medical imaging apparatus 3 is transmitted to the medical data processing apparatus 1.

After step SC1, the processing circuitry 11 implements the regular restoration function 112 (step SC2). At step SC2, the processing circuitry 11 reconstructs the CT image of the subject by applying the analytical image reconstruction such as FBP and the iterative reconstruction to the projection data acquired at step SC1.

After step SC2, the processing circuitry 11 implements the imaging control function 111 (step SC3). At step SC3, the processing circuitry 11 controls the medical imaging apparatus 3 to execute the PET imaging on the subject. The coincidence data of the subject acquired by the medical imaging apparatus 3 is transmitted to the medical data processing apparatus 1.

After step SC3, the processing circuitry 11 implements the regular restoration function 112 (step SC4). At step SC4, the processing circuitry 11 reconstructs a PET image of the subject by applying the analytical image reconstruction such as FBP or iterative reconstruction to the coincidence data acquired at step SC3. PET imaging involves a lower gamma ray detection efficiency than the X-ray detection efficiency of X-ray CT imaging, and therefore the image quality of a PET image is degraded in comparison to a CT image.

After steps SC2 and SC4, the processing circuitry 11 implements the image processing function 115 (step SC5). At step SC5, the processing circuitry 11 aligns the CT image reconstructed at step SB2 with the PET image reconstructed at step SC4. The alignment may be performed by any method such as rigid-body alignment or non-rigid alignment.

After step SC5, the processing circuitry 11 implements the input selection function 113 (step SC6). At step SC6, the processing circuitry 11 selects the PET image aligned at step SC5 as a target input image, and the CT image aligned at step SC5 as an auxiliary input image (step SC6).

After step SC6, the processing circuitry 11 implements the forward-propagation function 114 (step SC7). At step SC7, the processing circuitry 11 applies the learned DNN to the PET image and the CT image to generate a PET-based DNN reconstruction image. In particular, with the forward-propagation function 114, the processing circuitry 11 first reads from the memory 13 a learned DNN (for PET) in which a PET image is the target input image, a CT image is an auxiliary input image, and a PET image from which any data deficit has been removed is a target output image. Next, the processing circuitry 11 enters the PET image into the process target area 921 of the input layer 91 of the learned DNN (for PET) and the CT image to the auxiliary area 922. Then, the processing circuitry 11 performs the forward propagation on the entered PET image and CT image in the learned DNN (for PET). In this manner, a PET-based DNN reconstruction image can be generated.

After step SC7, the processing circuitry 11 implements the display control function 116 (step SC8). At step SC8, the processing circuitry 11 displays the PET-based DNN reconstruction image generated at step SC7 and the CT image aligned at step SC5, on the display 19. The processing circuitry 11 may display a composite image of a PET/CT-based DNN reconstruction image and a CT image.

The process of the medical data processing apparatus 1-3 according to application example 3 has been explained.

The flow of the process shown in FIG. 22 is described merely as an example, and the process according to application example 3 is not limited to the flow shown in FIG. 22 only. The order of X-ray CT imaging at step SC1 and PET imaging at step SC3 may be interchanged.

The order of the alignment process at step SC5 and the selection process at step SC6 maybe interchanged. The alignment process at step SC5 and the forward-propagation processing at step SC7 have been described as separate processes, but the alignment process at step SC5 may be incorporated into the learned DNN (for PET).

As described above, according to application example 3, a target input image and an auxiliary input image are selected from the PET images and CT images acquired by the execution of the PET/CT examinations. The forward propagation of the learned DNN is performed with a relatively high quality CT image serving as an auxiliary input image and a relatively low quality PET image serving as a target input image. In this manner, a high quality PET image can be generated and displayed using a CT image.

Application Example 4

Ultrasound Examination

An ultrasound examination is performed by an ultrasonic diagnostic apparatus. In application example 4, an ultrasonic probe of an ultrasonic diagnostic apparatus serves as the medical imaging apparatus 3.

Figure 24:
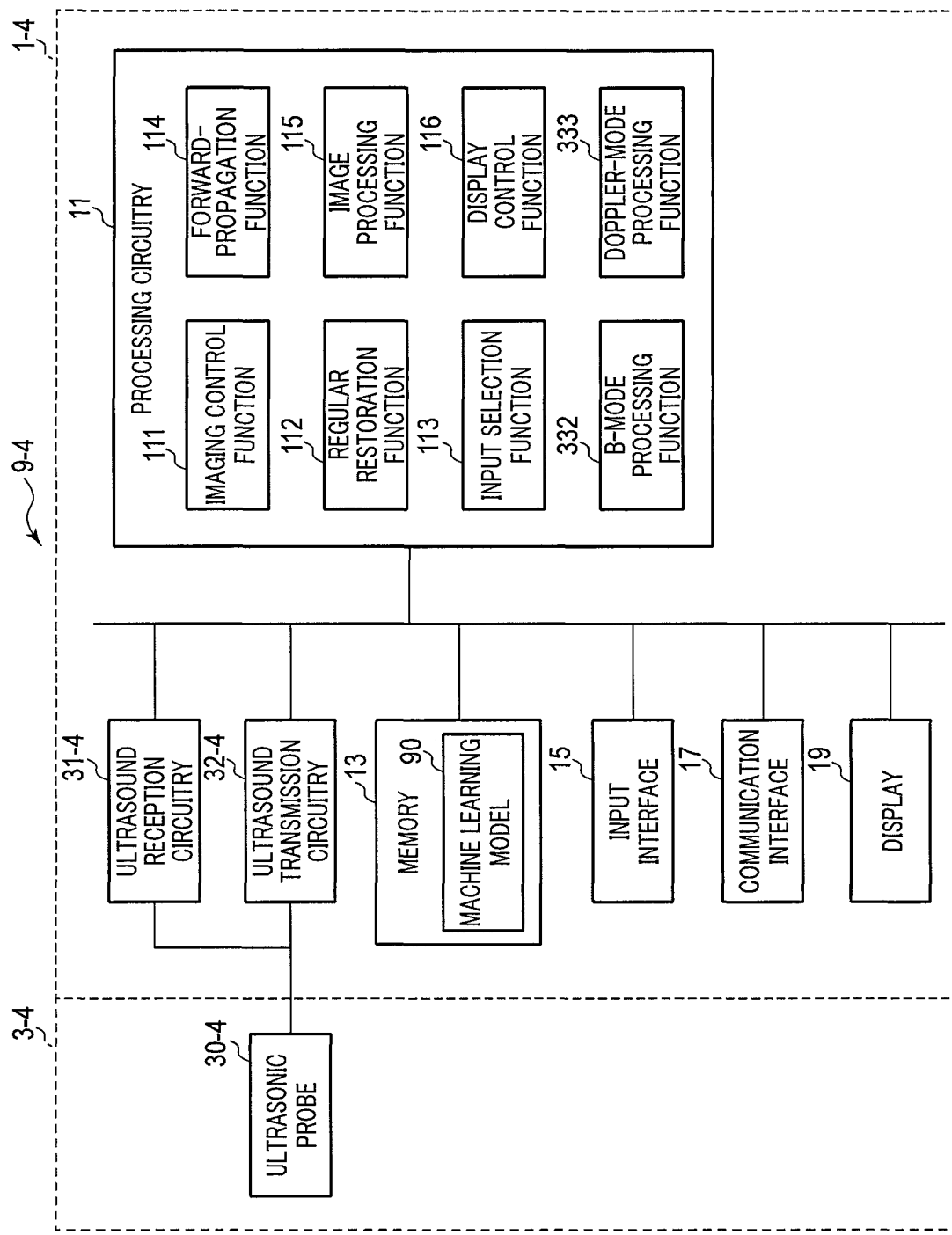
FIG. 24 is a diagram showing the configuration of an ultrasonic diagnostic apparatus according to application example 4.

FIG. 24 is a diagram showing the configuration of an ultrasonic diagnostic apparatus 9-4 according to application example 4. As shown in FIG. 24, the ultrasonic diagnostic apparatus 9-4 includes an ultrasonic probe 3-4 and a medical data processing apparatus (apparatus body) 1-4.

With the imaging control function 111 of the medical data processing apparatus 1-4, the ultrasonic probe 3-4 may execute ultrasound scanning in the scan region of a living body of a patient. The ultrasonic probe 3-4 may include a plurality of piezoelectric transducers, a matching layer, a backing material, and the like. In the present embodiment, the ultrasonic probe 3-4 may include a plurality of ultrasonic vibrators aligned in a predetermined direction. The ultrasonic probe 3-4 is detachably connected to the apparatus main body 1-4.

The plurality of piezoelectric transducers generate ultrasonic waves in accordance with the drive signal supplied from the ultrasound transmission circuitry 32-4 of the medical data processing apparatus 1-4. In this manner, ultrasonic waves are transmitted from the ultrasonic probe 3-4 to the living body. When the ultrasonic waves are transmitted from the ultrasonic probe 3-4 to the living body, the transmitted ultrasonic waves are sequentially reflected on the acoustic impedance discontinuous surface of the body tissue of the living body, and are received as reflection wave signals by the piezoelectric transducers. The amplitude of the received reflection wave signals depends on the difference in the acoustic impedance on the discontinuous surface on which the ultrasonic waves are reflected. If the transmitted ultrasonic pulse is reflected by bloodstream, the surface of a radiation absorbing tissue spacer or the like, the frequency of its reflection wave signal is shifted by the Doppler effect, depending on the velocity component of the moving body in the ultrasound transmission direction. The ultrasonic probe 3-4 receives the reflection wave signal from the living body and converts it into an electric signal. The electrical signal is supplied to the medical data processing apparatus 1-4.

The medical data processing apparatus 1-4 shown in FIG. 24 is a computer configured to generate and display an ultrasonic image, based on the reflection wave signal received by the ultrasonic probe 3-4. The medical data processing apparatus 1-4 includes an ultrasound transmission circuitry 32-4, an ultrasound reception circuitry 31-4, the processing circuitry 11, the memory 13, the input interface 15, the communication interface 17 and the display 19, as shown in FIG. 24.

The ultrasound transmission circuitry 32-4 is a processor for supplying a drive signal to the ultrasonic probe 3-4. The ultrasound transmission circuitry 32-4 is realized, for example, by a trigger generating circuitry, a delay circuitry, a pulsar circuitry, and the like. The trigger generating circuitry repeatedly generates rate pulses for forming transmission ultrasonic waves at a predetermined rate frequency. The delay circuitry gives a delay time to each rate pulse generated by the trigger generating circuitry for each piezoelectric vibrator. This delay time is necessary to converge the ultrasonic wave generated from the ultrasonic probe 3-4 into a beam shape and determine the transmission directivity. The pulsar circuitry applies a drive signal (drive pulse) to the ultrasonic vibrators provided in the ultrasonic probe 3-4 at the timing based on the rate pulse. By suitably changing the delay time given to each rate pulse by the delay circuitry, the transmission direction from the surface of the piezoelectric transducers can be suitably adjusted.

The ultrasound reception circuitry 31-4 is a processor that performs various processes on the reflection wave signal received by the ultrasonic probe 3-4 and generates a reception signal. The ultrasound reception circuitry 31-4 is realized, for example, by an amplifier circuitry, an A/D converter, a reception delay circuitry, an adder, and the like. The amplifier circuitry amplifies the reflection wave signal received by the ultrasonic probe 3-4 for each channel, and performs gain correction processing. The A/D converter converts the gain-corrected reflection wave signal to a digital signal. The reception delay circuitry gives the delay time necessary to determine the reception directivity to the digital signal. The adder adds a plurality of digital signals to which a delay time is given. With the addition processing by the adder, a reception signal is generated, in which a reflection component from a direction corresponding to the reception directivity is emphasized.

The processing circuitry 11 may be a processor that serves as the center of the ultrasonic diagnostic apparatus 9-4. The processing circuitry 11 implements the program stored in the memory 13 and thereby realizes the functions corresponding to the program. The processing circuitry 11 includes, for example, the imaging control function 111, regular restoration function 112, input selection function 113, forward-propagation function 114, image processing function 115, display control function 116, B-mode processing function 332 and Doppler-mode processing function 333.

With the B-mode processing function 332, the processing circuitry 11 generates B-mode data based on the reception signal received from the ultrasound reception circuitry 31-4. Specifically, the processing circuitry 11 performs, for example, envelope detection processing, logarithmic amplification processing, and the like on the reception signal received from the ultrasound reception circuitry 31-4, and thereby generates data (B-mode data) in which the signal intensity is represented by luminance. The generated B-mode data is stored as B-mode raw data on two-dimensional ultrasonic scanning lines (rasters) in a raw data memory (not shown).

With the Doppler-mode processing function 333, the processing circuitry 11 analyzes the frequency of the reception signal received from the ultrasound reception circuitry 31-4, and thereby generates data (Doppler data) obtained by extracting the motion information of the bloodstream in the region of interest (ROI) that is set in the scan region, based on the Doppler effect. Specifically, the processing circuitry 11 generates the Doppler data by estimating the mean velocity, mean dispersion value, mean power value, etc., as the motion information of the bloodstream for each of the sample positions. The generated Doppler data is stored as Doppler raw data on two-dimensional ultrasonic scan lines, in a raw data memory (not shown).

For the Doppler-mode processing function 333, the processing circuitry 11 may execute a color Doppler method called color flow mapping (CFM). In the CFM method, the transmission and reception of ultrasonic waves are performed on a plurality of scan lines a plurality of times. The processing circuitry 11 suppresses signals (clutter signals) derived from any stationary tissue or slow-moving tissue by setting a moving target indicator (MTI) filter for data strings of the same position so that the signals derived from a bloodstream can be extracted. Then, the processing circuitry 11 estimates information such as the velocity, dispersion or power of the bloodstream from the extracted signals.

With regard to the memory 13, input interface 15, communication interface 17, display 19, imaging control function 111, regular restoration function 112, input selection function 113, forward-propagation function 114, image processing function 115 and display control function 116, their explanation is omitted.

FIG. 25 is a schematic diagram showing the process of the medical data processing apparatus 1-4 according to application example 4. In the ultrasound examination, the processing circuitry 11 generates an ultrasonic image of time-series frames. Specifically, with the imaging control function 111, the processing circuitry 11 executes ultrasonic imaging by way of the ultrasonic probe 3-4 and acquires the echo data of time-series frames in real time. Next, the processing circuitry 11 implements the B-mode processing function 332 and generates the B-mode data of the time-series frames based on the echo data of the time-series frames. Then, the processing circuitry 11 implements the regular restoration function 112 and generates B-mode images IU of the time-series frames based on the B-mode data of the time-series frames. The B-mode images IU of time-series frames are dynamically displayed on the display 19.

As shown in FIG. 25, the present frame is "t". A B-mode image IUt is displayed on the display 19 at the present frame t. The frame t-n is an integer denoting "n" frames before the present frame t. The B-mode image IU-n displayed on the display 19 may be generated with the regular restoration function 112 of the processing circuitry 11, for example, by the scan converting technique. For this reason, the B-mode image IU-n is of relatively coarse image quality.

The user presses the freeze button (still button) via the input interface 15 when the frame that he/she wishes to observe in detail is displayed. In FIG. 25, the freeze button is pressed at the present frame t. At the press of the freeze button, the processing circuitry 11 displays the B-mode image IUt of the present frame t as a still image on the display 19.

Furthermore, at the press of the freeze button, the processing circuitry 11 implements the input selection function 113 and the forward-propagation function 114 in this order. With the input selection function 113, the processing circuitry 11 selects the B-mode image IUt of the present frame t as a target input image, and selects the B-mode image IUt-n of the previous frame t-n with respect to the present frame t, as an auxiliary input image. As the previous B-mode image IUt-n, it is preferable that the B-mode image IUt-1 of the previous frame t-1 immediately before the present frame t, which can be considered as closely resembling the B-mode image IUt of the present frame t in form, be selected. It is also possible that, as the previous B-mode image IUt-n, the B-mode image of the previous frame that belongs to the same respiratory phase or cardiac phase as the B-mode image IUt of the present frame t may be selected. For the previous B-mode image to be selected, a B-mode image ahead of the present frame t may be selected. It is assumed here that the B-mode image IUt-1 of the frame t-1 is selected as an auxiliary input image.

Thereafter, the processing circuitry 11 implements the forward-propagation function 114. With the forward-propagation function 114, the processing circuitry 11 applies the learned DNN to the B-mode image (target input image) IUt of the present frame t and the B-mode image (auxiliary input image) IUt-1 of the previous frame t-1 to generate a DNN reconstruction image IU0 of the present frame t. Specifically, the processing circuitry 11 first reads from the memory 13 a learned DNN (for ultrasonic image) in which the B-mode image of the first frame is the target input image, the B-mode image of the second frame is the auxiliary input image, and the B-mode image with the data deficit portion restored is the target output image. Next, the processing circuitry 11 enters the B-mode image IUt of the present frame t to the process target area 921 of the input layer 91 of the learned DNN (for ultrasonic image), and the B-mode image IUt-1 of the previous frame t-1 to the auxiliary area 922. The processing circuitry 11 performs the forward propagation on the entered B-mode image IUt and the B-mode image IUt-1 in the learned DNN. In this manner, a B-mode image IU0 in which the data deficit portion is restored can be generated with respect to the present frame t.

The B-mode image IU0 generated by the forward-propagation function 114 is displayed as a still image on the display 19. The B-mode image IU0 may be displayed side by side with the B-mode image IUt, or may be displayed in place of the B-mode image IUt.

At the press of the freeze button again, the processing circuitry 11 performs ultrasonic imaging on the subject P by way of the ultrasonic probe 30-4 so that the B-mode images of the time-series frames can be generated and displayed on the display 19 in real time.

The process of the medical data processing apparatus 1-4 according to application example 4 has been explained.

In the above description, an ultrasonic image is assumed to be a B-mode image, but the present embodiment is not limited thereto. For example, the ultrasonic image may be a Doppler-mode image.

As described above, according to application example 4, a target input image and an auxiliary input image are selected from the ultrasonic images acquired by the execution of an ultrasound examination. An ultrasonic image whose morphology is similar to the target input image is selected as an auxiliary input image. In this manner, an ultrasonic image of relatively high image quality can be instantaneously generated and displayed.

Application Example 5

X-Ray Fluoroscopic Examination

An X-ray fluoroscopic examination is performed by an X-ray diagnostic apparatus. In application example 5, the medical imaging apparatus 3 is a C-arm to which an X-ray tube and an X-ray detector are attached. Application example 5 is the same as application example 4.

In an X-ray fluoroscopic examination, the processing circuitry 11 generates a radiologic image from high-dose X-ray imaging with the C-arm and a fluoroscopic image from continuous low-dose X-ray imaging, and displays the radiologic image and fluoroscopic image on the display 19. A radiologic image exhibits a higher image quality than a fluoroscopic image. The radiologic image and fluoroscopic image may be displayed side by side, or the fluoroscopic image with a narrow field of view may be superimposed on the radiologic image with a wide field of view. In general, a radiologic image is a still image, while a fluoroscopic image is a moving image. The radiologic image, which depicts the contrast vessels with a high image quality, offers a road map for the contrast vessels. The fluoroscopic image depicts blood vessels in real time. The surgeon or the like inserts surgical tools such as catheters to reach the target site, while observing the radiologic image and the fluoroscopic image.

When the fluoroscopic image of the frame to be observed in detail is displayed, the user presses the freeze button via the input interface 15. At the press of the freeze button, the processing circuitry 11 displays the fluoroscopic image of the present frame as a still image on the display 19.

Furthermore, at the press of the freeze button, the processing circuitry 11 implements the input selection function 113 and the forward-propagation function 114 in this order. With the input selection function 113, the processing circuitry 11 selects, as a target input image, the fluoroscopic image of the present frame and, as an auxiliary input image, the radiologic image of a previous or future frame that satisfies the predetermined criteria. With the forward-propagation function 114, the processing circuitry 11 reads from the memory 13 a learned model (for X-ray image) in which a fluoroscopic image is the target input image, a radiologic image is the auxiliary input image, and a DNN fluoroscopic image with the data deficit portion restored is the target output image. Next, the processing circuitry 11 enters the fluoroscopic image of the present frame to the process target area 921 of the input layer 91 of the learned model (for X-ray image) and the radiologic image of the previous or future frame that satisfies the predetermined criteria to the auxiliary area 922. The processing circuitry 11 performs the forward propagation on the entered fluoroscopic image and radiologic image in the learned DNN. In this manner, a DNN fluoroscopic image in which the data deficit portion is restored can be generated with respect to the present frame t. The generated DNN fluoroscopic image is displayed as a still image on the display 19.

As described above, according to application example 5, a target input image is selected from the fluoroscopic images acquired by the execution of an X-ray fluoroscopic examination, and a radiologic image similar in morphology to the target input image and high in image quality is selected as an auxiliary input image. In this manner, high-quality X-ray images can be instantaneously generated and displayed with low dose.

Implementation Example 1

The processing circuitry 11 according to implementation example 1 reconstructs a video image from highly under-sampled radial k-space data. In order to achieve spatial and temporal correlations and reduce the reconstruction time delay, a deep neural network is trained with additional input images representing the assisted correlations. The image quality in the method of this example is superior to that of the method based on the conventional DNN reconstruction from a single input to a single output.

The clinical use of dynamic MRI requires both fast data acquisition and low-delay reconstruction. Such methods include the reconstruction of images from highly under-sampled k-space data that includes a stack-of-stars trajectory (i.e., a stack of two-dimensional golden-angle radial trajectories) and compressed sensing with temporal constraints. However, many frames (e.g., entire series of video images) are required to evaluate temporal constraints. This approach is therefore not suitable for low-delay reconstruction. Because of low delay reconstruction, the image reconstruction method with a single image is preferred. An example of such methods is the use of a DNN from a single input image to a single output image. However, this method, which does not use temporal correlations, requires a higher number of spokes than the temporal constraint-based method.

FIG. 26 is a schematic diagram showing the process of the medical data processing apparatus 1 according to implementation example 1. In order to integrate spatial and temporal correlations with reduced-delay reconstruction, the processing circuitry 11 according to implementation example 1 performs a dynamic reconstruction method using a DNN whose inputs are consecutive M frames of neighboring N slices and output is a single reconstruction image, as shown in FIG. 26. The processing circuitry 11 according to the implementation example reconstructs images in a frame-by-frame manner. Since each frame depends on only (M−1)/2 future frames, the reconstruction delay time is expected to be lower than that in a method based on compressed sensing. The method according to the implementation example can be considered as an extension of a conventional reconstruction method using a DNN. With the conventional reconstruction method, M=N=1 is established. The DNN according to the implementation example consists of a plurality of convolution layers, a plurality of ReLU, and a plurality of residual connections.

FIG. 27 is a diagram showing an overview of the DNN according to implementation example 1. As shown in FIG. 27, the processing circuitry 11 applies a Fast Fourier Transform (FFT) in the stack direction as a preprocessing step. For each 2D radial k-space frame, the processing circuitry 11 reconstructs an initial image, using a non-uniform FFT (NUFFT) and parallel imaging (PI). The method for reconstructing an initial image does not rely on spatial correlations and temporal correlations with other images. Spatial correlations and temporal correlations are integrated into the DNN. An intermediate layer consists of a convolution layer with 3×3 kernel and a ReLU. A residual connection is inserted for each two stacked intermediate layers. The number of intermediate layers is 10. Each of the first and the last layer consists of only convolution layers with 1×1 kernel. The number of channels in each intermediate layer is 128.

Datasets from 2 volunteers are acquired for training. A dataset from 1 volunteer is acquired for validation. All datasets include Cartesian images with matrix size 256×160×16. In addition, the validation dataset includes actual k-space data using a stack-of-stars trajectory. For each radial k-space frame, 21 spokes are assigned. The number of input images is set to M=5 and N=3. For generating the inputs of the DNN, 10 frames are generated from the Cartesian images by simulating a radial sampling. The DNN is trained by Adaptive moment estimation (Adam) with a mean-squared-error loss function.

Figure 32:
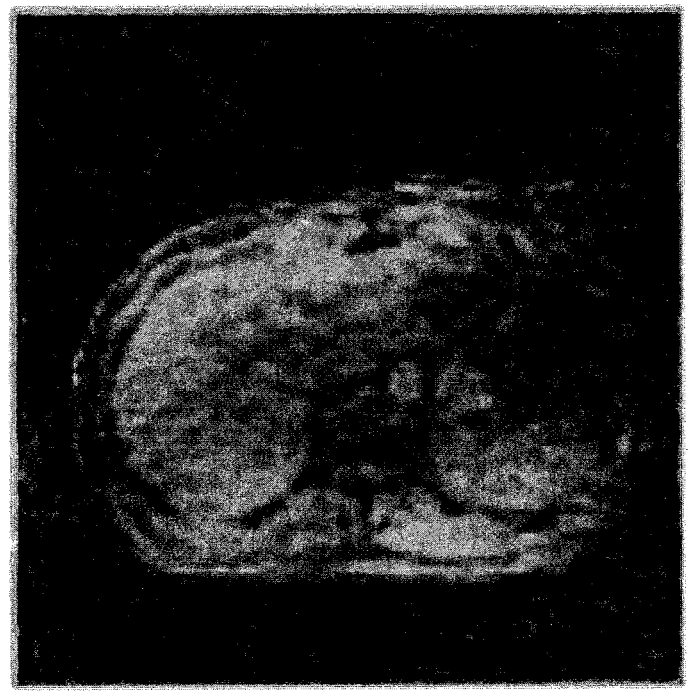
FIG. 32 is a diagram showing a reconstruction image obtained by NUFFT and PI, as a result of actual stack-of-stars data (21 spokes per frame).
Figure 33:
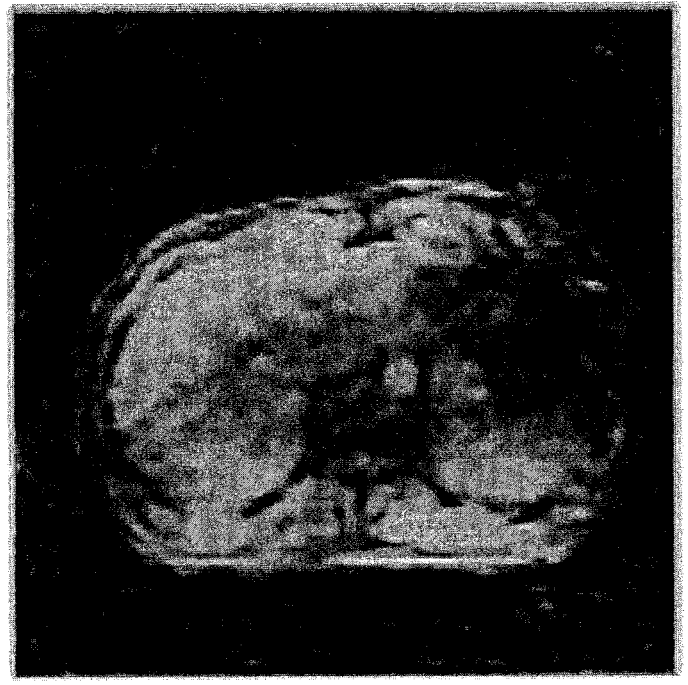
FIG. 33 is a diagram showing a reconstruction image obtained by the normal reconstruction method (M=N=1), as a result of actual stack-of-stars data (21 spokes per frame).
Figure 34:
FIG. 34 is a diagram showing a reconstruction image obtained by the reconstruction method (M=5 and N=3) according to the implementation example, as a result of actual stack-of-stars data (21 spokes per frame).

FIGS. 28, 29, 30 and 31 show the results obtained using the simulated radial data (21 spokes per frame). FIG. 28 is a diagram showing a reconstruction image using NUFFT+PI. FIG. 29 is a diagram showing a reconstruction image using the conventional reconstruction method (M=N=1). FIG. 30 is a diagram showing a reconstruction image using the reconstruction method (M=5 and N=3) according to implementation example 1. FIG. 31 is a diagram showing a true reconstruction image. FIGS. 32, 33 and 34 are diagrams showing the results of actual stack-of-stars data (21 spokes per frame). FIG. 32 is a diagram showing a reconstruction image by NUFFT+PI. FIG. 33 is a diagram showing a reconstruction image according to the conventional reconstruction method (M=N=1). FIG. 34 is a diagram showing a reconstruction image with the reconstruction method (M=5 and N=3) according to implementation example 1. The image quality of the images reconstructed using the reconstruction method of M=5 and N=3 is clearly improved over the images reconstructed using NUFFT+PI and the images reconstructed using the reconstruction method of M=N=1. In particular, the actual stack-of-stars data clearly depicts the structure within the liver by using spatial correlations and temporal correlations.

The method according to implementation example 1 can reconstruct video images from 21 spokes per frame, which is significantly lower than 45 spokes in a projection reconstruction method using DNN. The quality of resultant images from actual stack-of-stars data is lower than the quality of images from simulated radial data. In order to improve the image quality, the imperfections of MRI system sampling should be accounted for in the simulation of radial sampling. Improvement of the simulation is deferred to future work.

As described above, the method according to implementation example 1 integrates the spatial correlations and temporal correlations into a DNN. Unlike methods based on compressed sensing, the method according to implementation example 1 can reconstruct images in a frame-by-frame manner and thus can be used for low-delay reconstruction. The experimental results show that the method according to implementation example 1 is effective for reconstruction of highly undersampled radial dynamic images.

Implementation Example 2

As the auxiliary input image according to implementation example 2, two or more images of the same slice position with different acquisition times and different temporal resolutions are adopted. Hereinafter, the medical data processing apparatus 1 according to implementation example 2 will be described. The medical data processing apparatus 1 according to implementation example 2 may be mounted in any medical image diagnostic apparatus capable of performing dynamic imaging of time-series frames. To make the explanation specific, the medical data processing apparatus 1 will be considered as being mounted in the magnetic resonance imaging apparatus 9-1. In magnetic resonance imaging, dynamic imaging can be executed in any kind of k-space trajectory. In the following embodiment, dynamic imaging based on radial scanning with relatively high temporal resolution will be considered. The MR image may be a two-dimensional image or a three-dimensional image. For example, as dynamic imaging of three-dimensional images based on radial scanning, three-dimensional radial scanning or stack-of-stars may be adopted.

The processing circuitry 11 according to the implementation example 2 executes dense input for the inputting the auxiliary input image to the DNN. The dense input is a method of inputting to the DNN the image data of a plurality of frames temporally close to the frame of the target input image in a hierarchical temporal resolution. The dense input is expected to further improve the image quality of the target output image.

FIG. 35 is a schematic diagram showing the dense input. The horizontal axis of FIG. 35 is defined by time, and the vertical axis is defined by temporal resolution. The temporal resolution is expressed in levels. Level 1 represents a temporal resolution corresponding to a single imaging frame. A single imaging frame is the time required to acquire a predetermined amount of k-space data required for one frame of image reconstruction. For example, when one frame contains ten spokes in radial scanning, one imaging frame is the time required for acquiring the k-space data corresponding to 10 spokes. In FIG. 35, it is assumed that temporal resolution levels are determined as levels 1 to 5. Level 2 is a 1/2 temporal resolution of level 1; level 3 is a 1/3 temporal resolution of level 1; Level 4 is a 1/4 temporal resolution of level 1; and level 5 is a 1/5 temporal resolution of level 1. When the dense input is applied to N imaging frames (level-1 frames), N(N+1)/2 frames are generated. The number of n-th level frames is N+1−2. The lower temporal resolution means there is more k-space data, which means a higher image quality.

Specifically, by implementing the imaging control function 111, the processing circuitry 11 acquires the k-space data of the time-series frames FR1-1, FR1-2, FR1-3, FR1-4 and FR1-5 that relate to level 1. With the regular restoration function 112, MR images of frames FR1-1, FR1-2, FR1-3, FR1-4 and FR1-5 are generated based on the k-space data of time-series frames FR1-1, FR1-2, FR1-3, FR1-4 and FR1-5.

The processing of level 2 may be executed as follows. The processing circuitry 11 integrates the k-space data of the temporally consecutive frames FR1-1 and FR1-2 to generate the k-space data of the frame FR2-1. Similarly, the processing circuitry 11 integrates the k-space data of the temporally consecutive frames FR1-2 and FR1-3 to generate the k-space data of the frame FR2-2; the k-space data of the temporally consecutive frames FR1-3 and FR1-4 to generate the k-space data of the frame FR2-3; and the k-space data of the temporally consecutive frames FR1-4 and FR1-5 to generate the k-space data of the frame FR2-4.

The processing is performed for levels 3, 4 and 5 in a similar manner. For level 3, the processing circuitry 11 integrates, for example, the k-space data of the temporally consecutive frames FR1-1, FR1-2, and FR1-3 to generate the k-space data of the frame FR3-1. For level 4, the processing circuitry 11 integrates, for example, the k-space data of the temporally consecutive frames FR1-1, FR1-2, FR1-3, and FR1-4 to generate the k-space data of the frame FR4-1. For level 5, the processing circuitry 11 integrates, for example, the k-space data of temporally consecutive frames FR1-1, FR1-2, FR1-3, and FR1-4 and FR1-5 to generate the k-space data of the frame FR5-1.

The above-mentioned frame integration method is merely an example, and is not limited thereto. In the above example, the k-space data of two or more temporally consecutive frames is integrated. However, the k-space data of two or more frames that are not temporally consecutive may be integrated. For example, the k-space data of frames FR1-1 and FR1-3 may be integrated. Furthermore, in the above example, a plurality of frames of the same level do not overlap in time, but a plurality of frames of the same level may overlap in time. In addition, a plurality of frames of the same level are defined with no interval in time, but any temporally adjacent two frames may be defined as temporally separated.

FIG. 36 is a diagram showing an example of the DNN reconstruction using dense input according to implementation example 2. As shown in FIG. 36, the temporal resolution of level 1 is a temporal resolution of a single imaging frame, for example, of 5 seconds/frame (f); the temporal resolution of level 2 is, for example, of 10 seconds/f, the temporal resolution of level 3 is, for example, 15 seconds/f.

It is preferable that the processing of FIG. 36 is executed in real time during MR imaging. The processing circuitry 11 generates the k-space data of time-series frames by radial scanning or the like by implementing the imaging control function 111. As shown in FIG. 36, for example, the k-space data of time-series frames FR1-1, FR1-2, FR1-3 and FR1-4 of level 1 is generated. Based on the k-space data of each frame FR1-$n$ (n is an integer), the processing circuitry 11 instantaneously generates the MR image of the frame FR1-$n$. Any method can be adopted for the MR image reconstruction. In order to enhance the immediacy of MR image generation, a simple reconstruction method such as the Jackson method (or gridding method) is preferable.

Every time an MR image of the latest level-1 frame FR1-4 is generated, the processing circuitry 11 generates the MR images of the level-2 frames FR2-1, FR2-2 and FR2-3 and the MR images of the level-3 frames FR3-1 and FR3-2, based on the k-space data of the level-1 frames FR1-1, FR1-2, FR1-3 and FR1-4. The processing circuitry 11 then selects the MR image of the latest level-1 frame FR1-4 as the target input image.

Next, an auxiliary input image is selected. According to implementation example 2, the number of imaging frames to be selected as auxiliary input images (hereinafter referred to as the number of auxiliary input images) is preset. The number of auxiliary input images may be set as the total number of images, or the number of images maybe set for each level. The processing circuitry 11 selects as auxiliary input images the MR images of the latest frames that satisfy the condition from the generated multi-level and multi-frame MR images. For example, as shown in FIG. 36, the number of level-1 frames is set to 4, the number of level-2 frames is set to 3, and the number of level-3 frames is set to 2. In this case, the four frames including the frames FR1-4 and frames FR1-3, FR1-2 and FR1-1 prior to the latest level-1 frame FR1-4, and the level-2 and higher frames FR2-1, FR2-2, FR2-3, FR3-1 and FR3-2 based on the four frames, are selected as auxiliary input images.

As indicated above, the MR image of the same level and the same frame as the target input image may be selected as the auxiliary input image. If not necessary, the MR image of the same level and the same frame as the target input image may be excluded from the auxiliary input images.

When the target input image and auxiliary input images are selected, the processing circuitry 11 enters the selected target input image and auxiliary input images to a learned DNN (for dense input), and generates a target output image. For example, as shown in FIG. 36, when the MR image of the present frame FR1-4 as a target input image is entered to the learned DNN (for dense input), and the MR images of frames FR1-4, FR1-3, FR1-2, FR1-1, FR2-3, FR2-2, FR2-1, FR3-2, and FR3-1 as auxiliary input images are entered, the MR image of the present frame FR1-4 is output as a target output image. According to implementation example 2, an MR image group having hierarchical temporal resolutions is entered as auxiliary input images to a learned DNN. In this manner, only the time continuity of several frames that are temporally close to the present frame FR1-4 can be entered to the learned DNN. As a result, the image quality of the DNN reconstruction image can be further improved.

The learned DNN (for dense input) according to implementation example 2 can be generated by the model learning apparatus 5 using the same method as in the above embodiment. The learned DNN (for dense input) is designed to receive MR images of multiple frames as auxiliary input images. A learned DNN (for dense input) is generated in accordance with each number of auxiliary input images. The true output image represents the same subject as the main input image, for which any image can be adopted as long as it is an MR image of a higher image quality than the main input image. For such a true output image, it is preferable that, for example, an MR image having a temporal resolution higher than the main input image or an MR image having a larger amount of k-space data (i.e., larger number of spokes) be selected. For example, if the main input image has the temporal resolution of level 1, it is preferable that an MR image with a temporal resolution higher than level 2 be selected as a true output image. For an auxiliary input image, an MR image group for dense input is selected. That is, multiple MR images with hierarchical resolutions and of multiple frames temporally close to the main input image frame are selected as the auxiliary input images.

Because of a relatively large number of auxiliary input images for a DNN for dense input, the processing circuitry 51 may adopt the dropout method at the time of training. Dropout is a method in which one or more units are selected from a plurality of units included in the DNN to be randomly (or pseudo-randomly) inactivated, and the DNN with the selected one or more units being inactivated is used for training. By adopting the dropout method, training can be accurately and efficiently performed.

As described above, according to implementation example 2, an MR image group being temporally close to the target input image (or main input image) and having hierarchical temporal resolutions is inputted to the DNN as auxiliary input images. Dense input is expected to improve the image quality of output images and the DNN training efficiency. Furthermore, the auxiliary input images are limited to the MR images of several previous frames with respect to the present frame, and therefore the MR images can be output in almost real time without waiting for the completion of dynamic imaging. In addition, the length of time to output the first image can be reduced.

Implementation Example 3

Implementation example 3 is an application of implementation example 2. In implementation example 2, an MR image of level-1 frame, which has a temporal resolution equivalent to that of the imaging frame, is entered to the DNN as an auxiliary input image. The present embodiment is not limited thereto. The processing circuitry 11 according to implementation example 3 enters to the DNN the MR images of only level-2 or higher frames as auxiliary input images.

FIG. 37 is a diagram showing an example of the DNN reconfiguration using dense input according to implementation example 3. As shown in FIG. 37, the temporal resolution of level 1 is of a single imaging frame, for example, of 2.5 seconds/frame (f); the temporal resolution of level 2 is, for example, 5 sec/f; and the temporal resolution of level 3 is, for example, 7.5 sec/f. In implementation example 3, because of the level-1 temporal resolution being relatively high, it is difficult to reconstruct an image from the k-space data of a single level-1 frame alone. When it is determined that the single frame reconstruction is difficult, the quality suitable for image interpretation cannot be attained because of the insufficient amount of k-space data in one frame. It is possible, however, to generate an MR image by applying a reconstruction method such as FFT to the k-space data of one frame.

As shown in FIG. 37, the k-space data of level-1 frames FR1-1, FR1-2, FR1-3, FR1-4 and FR1-5 are generated in real time. The frame FR1-5 is the present frame. Based on the k-space data of each frame FR1-$n$ ($n$ is an integer), the processing circuitry 11 instantaneously generates the MR image of each frame FR1-$n$ by a simple reconstruction method such as the Jackson method. Furthermore, every time an MR image of the latest level-1 frame FR1-5 is generated, the processing circuitry 11 generates the MR images of the level-2 frames FR2-1, FR2-2, FR2-3 and FR2-4 and the MR images of the level-3 frames FR3-1, FR3-2, and FR3-3, based on the k-space data of the present level-1 frame FR1-5 and the k-space data of the previous frames FR1-1, FR1-2, FR1-3 and FR1-4. The processing circuitry 11 then selects the MR image of the latest level-1 frame FR1-5 as a target input image.

Next, auxiliary input images are selected. In implementation example 3, the processing circuitry 11 selects, as the auxiliary input images, MR images of the number that matches the number of auxiliary input images, from the MR images of the level-2 or higher frames. As shown in FIG. 37, for example, the number of level-2 frames is set to 4, and the number of level-3 frames is set to 4, as the numbers of auxiliary input images. In this case, four frames FR1-4, FR1-3, FR1-2 and FR1-1 with regard to the latest level-1 frame FR1-4 and level-2 or higher frames FR2-1, FR2-2, FR2-3, FR3-1 and FR3-2 are selected as the auxiliary input images.

When the target input image and auxiliary input images are selected, the processing circuitry 11 enters the selected target input image and auxiliary input images to the learned DNN (for dense input), and generates a target output image. For example, as shown in FIG. 37, when the MR image of the present frame FR1-5 is entered as a target input image to the learned DNN (for dense input), and the MR images of the frames FR2-4, FR2-3, FR2-2, FR2-1, FR3-3, FR3-2, and FR3-1 are entered as auxiliary input images, the DNN reconstruction image of the present frame FR1-5 is output as a target output image.

As auxiliary input images, MR images of frames of any two or more levels may be selected, or MR images of frames of only a level higher than or equal to level 2 may be selected. For example, the MR images of frames of only the reconstruction level may be selected. In the above implementation example, the MR image of the present level-1 frame is selected as a target input image, but the present embodiment is not limited thereto. For example, the MR image of the previous level-1 frame may be selected as the target input image, or the MR image of any level-2 or higher frame may be selected as the target input image.

The learned DNN (for dense input) according to implementation example 3 can be generated by the model learning apparatus 5 using the same method as the implementation example 2. For example, if the main input image has the temporal resolution of level 1, it is preferable that an MR image with a temporal resolution of level 2 or higher be selected as a true output image. For auxiliary input images, an MR image group for dense input is selected. That is, multiple MR images with hierarchical temporal resolutions and of multiple frames temporally close to the frame of the main input image are selected as auxiliary input images.

According to implementation example 3, if the temporal resolution of the level-1 frame is too high to achieve the single reconstruction, MR images of the level-2 or higher frames are inputted as auxiliary input images to the learned DNN by the dense input method. In this manner, a high quality MR image can be generated, while maintaining a high imaging frame rate.

(Other Embodiments)

In the above described embodiments and its implementation examples, an example of deriving the parameters of the parameter-added composite function by deep neural network, which is a machine learning method, has been described, but the embodiment is not limited thereto. The method of machine learning is not limited to a method imitating the neural circuitry of a living organism's brain, and other methods may be adopted. Furthermore, the embodiment is not limited to deriving the parameters of the parameter-added composite function by machine learning. For example, instead of using machine learning, parameters may be derived by a person appropriately adjusting them. That is, the learned model 90 used by the medical data processing apparatus 1 is not limited to the machine learning model generated by the model learning apparatus 5. For example, the medical data processing apparatus 1 may use, as the learned model 90, a machine learning model in which parameters are set in accordance with the user's instructions.

According to at least one embodiment described above, the restoration accuracy of medical data can be improved.

The word "processor" used in the above explanation may be, for example, a CPU, GPU, application specific integrated circuit (ASIC), programmable logic device (e.g., simple programmable logic device (SPLD), complex programmable logic device (CPLD), and field programmable gate array (FPGA)) or the like. The processor realizes the functions by reading out and executing the program stored in the memory circuit. Instead of storing the program in the memory circuit, the program may be directly incorporated in the circuit of the processor. In this case, the processor realizes the functions by reading and executing the program incorporated in the circuit. Instead of executing the program, the functions corresponding to the program may be realized by a combination of logic circuits. Each processor of the present embodiment is not limited to a single circuit configured for each processor, and a plurality of independent circuits may be combined into a single processor that can realize the functions. Furthermore, a plurality of constituent elements in FIGS. 1, 3, 14, 15, 17, 19, 21 and 24 may be integrated into one processor to realize the functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Hereinafter, the gist of part of various inventions disclosed in this specification is given below.

[Appendix 1-1]
A medical data processing apparatus comprising:
a memory configured to store a learned model including an input layer to which first MR data and second MR data relating to an imaging target the same as the first MR data and an imaging parameter different from the first MR data are inputted, an output layer from which third MR data is output with a missing portion of the first MR data restored, and at least one intermediate layer arranged between the input layer and the output layer; and
processing circuitry configured to generate the third MR data relating to a subject in accordance with the learned model, from the first MR data serving as a process target and relating to the subject and the second MR data relating to the subject and acquired by an imaging parameter different from the first MR data serving as the process target.

[Appendix 1-2]
The medical data processing apparatus according to [Appendix 1-1], wherein the first MR data and the second MR data are k-space data or MR image data generated by performing a restoration process on the k-space data.

[Appendix 1-3]
The medical data processing apparatus according to [Appendix 1-2], wherein the restoration process includes denoising restoration or data error feedback restoration.

[Appendix 1-4]
The medical data processing apparatus according to [Appendix 1-1], wherein the imaging parameter includes at least one of a slice position, acquisition time, acquisition sequence, k-space trajectory and temporal resolution.

[Appendix 1-5]
The medical data processing apparatus according to [Appendix 1-4], wherein an amount of under-sampled data is larger in the first MR data than in the second MR data.

[Appendix 1-6]
The medical data processing apparatus according to [Appendix 1-1], wherein each of the first MR data and the second MR data is inputted as a single input vector to the learned model.

[Appendix 1-7]
The medical data processing apparatus according to [Appendix 1-6], wherein
the first MR data is assigned to a first region of the input vector,
the second MR data is assigned to a second region of the input vector, and
positions of the first region and the second region are fixed.

[Appendix 1-8]
The medical data processing apparatus according to [Appendix 1-7], wherein
the second MR data includes a plurality of sets of MR data having different imaging parameters, and
each of the sets of the second MR data is assigned to a fixed region of the second region of the input vector.

[Appendix 1-9]
The medical data processing apparatus according to [Appendix 1-1], further comprising training circuitry configured to generate estimated output data by applying the first MR data and the second MR data to a parameter-added composite function obtained by combining a plurality of functions, and generate the learned model by updating parameters of the parameter-added composite function such that the estimated output data and true output data approximate each other.

[Appendix 1-10]
The medical data processing apparatus according to [Appendix 1-1], wherein the processing circuitry is configured to:
select an imaging body part in accordance with user's instructions;
switch learned models in accordance with the selected imaging body part.

[Appendix 1-11]
The medical data processing apparatus according to [Appendix 1-1], wherein
the imaging parameter includes a first parameter and a second parameter,
the first MR data and the second MR data share the first parameter, and have the second parameters different from each other,
the first MR data and the third MR data share the first parameter and the second parameter,
the second MR data and the third MR data share the first parameter, and have the second parameters different from each other, and
the third MR data includes less data deficit or higher image quality than the first MR data.

[Appendix 1-12]
The medical data processing apparatus according to [Appendix 1-11], wherein
the first parameter represents a slice position, and
the second parameter represents an acquisition time, acquisition sequence, k-space trajectory and temporal resolution.

[Appendix 1-13]
The medical data processing apparatus according to [Appendix 1-11], wherein the first parameter represents at least one of an acquisition sequence, k-space trajectory and temporal resolution, and
the second parameter represents a slice position.

[Appendix 1-14]
The medical data processing apparatus according to [Appendix 1-11], wherein
the first parameter represents a slice position and an EPI acquisition sequence, and
the second parameter represents a value b of the acquisition sequence.

[Appendix 1-15]
A memory configured to store a learned model comprising an input layer to which first k-space data or MR image data, second k-space data or MR image data relating an imaging target the same as the first k-space data or MR image data and an imaging parameter different from the first k-space data or MR image data are inputted, an output layer from which third k-space data or MR image data is output with a missing portion of the first k-space data or MR image data being restored, and at least one intermediate layer arranged between the input layer and the output layer; and
processing circuitry configured to:
perform MR imaging on a subject and acquire the first k-space data relating to a first imaging parameter and the second k-space data relating to a second imaging parameter different from the first imaging parameter; and
generate the third k-space data or MR image data relating to the subject in accordance with the learned model, from the acquired k-space data or the MR image data based on the acquired k-space data, and the acquired second k-space data or the MR image data based on the acquired k-space data.

[Appendix 1-16]
The magnetic resonance imaging apparatus according to [Appendix 1-15], wherein the processing circuitry is configured to:
acquire k-space data of time-series frames including the first k-space data and the second k-space data; and
select, from among the k-space data of the frames, k-space data of one first frame as the first k-space data, and k-space data of one or more second frames as the second k-space data.

[Appendix 1-17]
The magnetic resonance imaging apparatus according to [Appendix 1-15], wherein the processing circuitry is configured to:
acquire k-space data of time-series frames including the first k-space data and the second k-space data, and
select, from among the k-space data of the frames, k-space data of one first frame as the first k-space data;
generate, based on the k-space data of the frames, k-space data of a plurality of second frames having different acquisition times and/or temporal resolutions; and
select the k-space data of the second frames as the second k-space data.

[Appendix 1-18]
The magnetic resonance imaging apparatus according to [Appendix 1-17], wherein the processing circuitry is configured to:
generate input MR image data of the first frame based on the k-space data of the first frame, k-space data of the second frames based on the k-space data of the frames;
input MR image data of the second frames based on the k-space data of the second frames; and
generate output MR image data of the first frame as the third MR data from the input MR image data of the first frame and the input MR image data of the second frames, in accordance with the learned model.

[Appendix 1-19]
The magnetic resonance imaging apparatus according to [Appendix 1-17], wherein
the frames and the first frame have a first temporal resolution level, and
the second frames have a second temporal resolution level that is lower than the first temporal resolution level.

[Appendix 1-20]
The magnetic resonance imaging apparatus according to [Appendix 1-19], wherein
the first temporal resolution level has a temporal resolution corresponding to one imaging frame,
the second temporal resolution level has a temporal resolution corresponding to two imaging frames or more,
the second frames include N(N+1)/2 frames, and
the second frames include (N+1−n) frames for each n-th temporal resolution level, from a temporal resolution level corresponding to N imaging frames to a temporal resolution level corresponding to two imaging frames.

[Appendix 1-21]
The magnetic resonance imaging apparatus according to [1-16], wherein the first MR data is included in the second MR data.

[Appendix 1-22]
A learned model generating method comprising steps of:
generating estimated output data to apply first MR data and second MR data relating to an imaging target the same as the first MR data and an imaging parameter different from the first MR data, to a parameter-added composite function obtained by combining a plurality of functions, and
generating a learned model by updating a parameter of the parameter-added composite function such that the estimated output data and true output data having a missing portion of the first MR data restored approximate each other.

[Appendix 2-1]
A medical data processing apparatus comprising:
a memory configured to store a learned model including an input layer to which first CT data and second CT data relating to an imaging target the same as the first CT data and an imaging parameter different from the first CT data are inputted, an output layer from which third CT data with a missing portion of the first CT data restored is output, and at least one intermediate layer arranged between the input layer and the output layer; and
processing circuitry configured to generate third CT data relating to a subject in accordance with the learned model, from the first CT data serving as a process target and relating to the subject, and the second CT data relating to the subject and acquired with the imaging parameter different from the first CT data relating to the process target.

[Appendix 2-2]
The medical data processing apparatus according to [Appendix 2-1], wherein the first CT data and the second CT data are projection data or CT image data generated by performing a restoration process on the projection data.

[Appendix 2-3]
The medical data processing apparatus according to [Appendix 2-2], wherein the restoration process is denoising restoration or data error feedback restoration.

[Appendix 2-4]
The medical data processing apparatus according to [Appendix 2-1], wherein the imaging parameter includes at least one of a slice position, acquisition time, tube current, tube voltage, focus size, spatial resolution of a detector, number of views, reconstruction function, gantry rotation velocity and temporal resolution.

[Appendix 2-5]
The medical data processing apparatus according to [Appendix 2-4], wherein an amount of under-sampled data is larger in the first CT data than in the second CT data.

[Appendix 2-6]
The medical data processing apparatus according to [Appendix 2-1], wherein the first CT data and the second CT data are inputted to the learned model as a single input vector.

[Appendix 2-7]
The medical data processing apparatus according to [Appendix 2-6], wherein
the first CT data is assigned to a first region of the input vector,
the second CT data is assigned to a second region of the input vector, and
positions of the first region and the second region are fixed.

[Appendix 2-8]
The medical data processing apparatus according to [Appendix 2-7], wherein
the second CT data includes a plurality of sets of CT data having different imaging parameters, and
each of the sets of second CT data is assigned to a fixed region of the second region of the input vector.

[Appendix 2-9]
The medical data processing apparatus according to [Appendix 2-1], further comprising training circuitry configured to generate estimated output data by applying the first CT data and the second CT data to a parameter-added composite function obtained by combining a plurality of functions, and generate the learned model by updating parameters of the parameter-added composite function such that the estimated output data and true output data approximate each other.

[Appendix 2-10]
The medical data processing apparatus according to [Appendix 2-1], wherein the processing circuitry is configured to:
select an imaging body part in accordance with user's instructions; and
switch learned models in accordance with the selected imaging body part.

[Appendix 2-11]
The medical data processing apparatus according to [Appendix 2-1], wherein the imaging parameter includes a first parameter and a second parameter,
the first CT data and the second CT data share the first parameter and have different second parameters,
the first CT data and the third CT data share the first parameter and the second parameter,
the second CT data and the third CT data share the first parameter and have different second parameters, and
the third CT data includes less data deficit or higher image quality than the first CT data.

[Appendix 2-12]
The medical data processing apparatus according to [Appendix 2-11], wherein
the first parameter represents a slice position, and
the second parameter represents an acquisition time and a tube current.

[Appendix 2-13]
An X-ray computed tomography imaging apparatus, comprising:
a memory configured to store a learned model comprising an input layer to which first projection data or CT image data and second projection data or CT image data relating to an imaging target the same as the first projection data or CT image data and an imaging parameter different from the first projection data or CT image data are inputted, an output layer from which third projection data or CT image data is output with a missing portion of the first projection data or CT image data restored, and at least one intermediate layer arranged between the input layer and the output layer, and
processing circuitry configured to:
acquire the first projection data relating to a first imaging parameter by performing CT imaging on a subject, and the second projection data relating to a second imaging parameter different from the first imaging parameter; and
generate the third projection data or CT image data relating to the subject from the acquired first projection data or CT image data and the acquired second projection data or CT image data, in accordance with the learned model.

[Appendix 2-14]
The X-ray computed tomography imaging apparatus according to [Appendix 2-13], wherein the processing circuitry is configured to:
acquire projection data of a plurality of rotations of a rotation frame,
generate first rotation CT image data as the first CT image data, based on projection data of a first rotation from among the projection data of the rotations, and
generate second rotation CT image data as the second CT image data, based on projection data of a second rotation from among the projection data of the rotations.

[Appendix 2-15]
The X-ray computed tomography imaging apparatus according to [Appendix 2-14], wherein
the first rotation projection data is generated by high-dose CT imaging, and
the second rotation projection data is generated by low-dose CT imaging.

[Appendix 2-16]
A learned model generating method, comprising steps of:
generating estimated output data by applying first CT data and second CT data relating to an imaging target the same as the first CT data and an imaging parameter different from the first CT data to a parameter-added composite function obtained by combining a plurality of functions; and
generating a learned model by updating parameters of the parameter-added composite function such that the estimated output data and true output data having a missing portion of the first CT data restored approximate each other.

[Appendix 3-1]
A medical data processing apparatus comprising:
a memory configured to store a learned model including an input layer to which first US data and second US data relating to an imaging target the same as the first US data and an imaging parameter different from the first US data are inputted, an output layer from which third US data with a missing portion of the first US data restored is output, and at least one intermediate layer arranged between the input layer and the output layer; and
processing circuitry configured to generate the third US data relating to a subject in accordance with the learned model, from the first US data serving as a process target and relating to the subject and the second US data relating to the subject and acquired by the imaging parameter different from the first US data serving as the process target.

[Appendix 3-2]
The medical data processing apparatus according to [Appendix 3-1], wherein the first US data and the second US data are US raw data or US image data generated by performing a restoration process on the US raw data.

[Appendix 3-3]
The medical data processing apparatus according to [Appendix 3-2], wherein the restoration process includes denoising restoration or data error feedback restoration.

[Appendix 3-4]
The medical data processing apparatus according to [Appendix 3-1], wherein the imaging parameter includes at least one of a slice position, acquisition time, focal position, gain, transmission intensity, reception intensity, PRF, beam scanning scheme, scanning mode, and temporal resolution.

[Appendix 3-5]
The medical data processing apparatus according to [Appendix 3-4], wherein an amount of under-sampled data is larger in the first US data than in the second US data.

[Appendix 3-6]
The medical data processing apparatus according to [Appendix 3-1], wherein each of the first US data and the second US data is inputted as a single input vector to the learned model.

[Appendix 3-7]
The medical data processing apparatus according to [Appendix 3-6], wherein
the first US data is assigned to a first region of the input vector,
the second US data is assigned to a second region of the input vector, and
positions of the first region and the second region are fixed.

[Appendix 3-8]
The medical data processing apparatus according to [Appendix 3-7], wherein
the second US data includes a plurality of sets of US data having different imaging parameters, and
each of the sets of second US data is assigned to a fixed region of the second region of the input vector.

[Appendix 3-9]
The medical data processing apparatus according to [Appendix 3-1], further comprising training circuitry configured to generate estimated output data by applying the first US data and the second US data to a parameter-added composite function obtained by combining a plurality of functions, and to generate the learned model by updating parameters of the parameter-added composite function such that the estimated output data and true output data approximate each other.

[Appendix 3-10]
The medical data processing apparatus according to [Appendix 3-1], wherein the processing circuitry is configured to:
select an imaging body part in accordance with user's instructions, and
switch learned models in accordance with the selected imaging body part.

[Appendix 3-11]
The medical data processing apparatus according to [Appendix 3-1], wherein
the imaging parameter includes a first parameter and a second parameter,
the first US data and the second US data share the first parameter, and have different second parameters,
the first US data and the third US data share the first parameter and the second parameter,
the second US data and the third US data share the first parameter and have different second parameters, and
the third US data includes less data deficit or higher image quality than the first US data.

[Appendix 3-12]
The medical data processing apparatus according to [Appendix 3-11], wherein
the first parameter represents a slice position, and
the second parameter represents an acquisition time.

[Appendix 3-13]
An ultrasonic diagnostic apparatus comprising:
a memory configured to store a learned model including an input layer to which first US raw data or US image data, and second US raw data or US image data relating to an imaging target the same as the first US raw data or US image data and an imaging parameter different from the first US raw data or US image data are inputted, an output layer from which third US raw data or US image data is output with a missing portion of the first US raw data or US image data restored, and at least one intermediate layer arranged between the input layer and the output layer; and
processing circuitry configured to:
acquire first US raw data relating to a first imaging parameter and second US raw data relating to a second imaging parameter different from the first imaging parameter by performing US imaging on the subject; and
generate third US raw data or US image data relating to the subject from the acquired first US raw data or the US image data based on the acquired first US raw data and the acquired second US raw data or the US image data based on the acquired second US raw data, in accordance with the learned model.

[Appendix 3-14]
An ultrasonic diagnostic apparatus according to [Appendix 3-13], wherein the processing circuitry is configured to:
acquire US raw data of time-series frames, and
select US raw data of one first frame as the first US raw data, and US raw data of one or more second frames as the second US raw data, from the US raw data of the frames.

[Appendix 3-15]
The ultrasonic diagnostic apparatus according to [Appendix 3-14], wherein the processing circuitry is configured to:
generate input US image data of the first frame based on the US raw data of the first frame, and input US image data of the second frames based on the US raw data of the second frames; and
generate, as the third US data, output US image data of the first frame from the input US image data of the first frame and the input US image data of the second frames in accordance with the learned model.

[Appendix 3-16]
The ultrasonic diagnostic apparatus according to [Appendix 3-15] further comprising a display configured to display US image data of the frames in real time, based on the US raw data of the frames,
wherein the processing circuitry is configured to:
in response to an image freeze command from a user, select US wave image data displayed on the display device at a time of the image freeze command, as the US image data of the first frame; and
select US image data of a frame a predetermined number of frames prior to the time of the image freeze command or a frame a predetermined number of frames after the time of the image freeze command, as the US image data of the second frames.

[Appendix 3-17]
A learned model generating method comprising:
generating estimated output data by applying first US data and second US data relating to an imaging target the same as the first US data and an imaging parameter different from the first US data to a parameter-added composite function obtained by combining a plurality of functions; and
generating a learned model by updating parameters of the parameter-added composite function such that the estimated output data and true output data having a missing portion of the first US data restored approximate each other.

[Appendix 4-1]
A medical data processing apparatus comprising:
a memory configured to store a learned model including an input layer to which first medical data and second medical data relating to an imaging target the same as the first medical data and an imaging parameter different from the first medical data are inputted, an output layer from which third medical data is output with a missing portion of the first medical data restored, and at least one intermediate layer arranged between the input layer and the output layer; and processing circuitry configured to generate third medical data relating to the subject in accordance with the learned model, from the first medical data serving as a process target and relating to a subject and the second medical data relating to the subject and acquired by an imaging parameter different from the first medical data serving as the process target.

[Appendix 4-2]

The medical data processing apparatus according to [Appendix 4-1], wherein the first medical data and the second medical data are raw data or medical image data generated by performing a restoration process on the raw data.

[Appendix 4-3]

The medical data processing apparatus according to [Appendix 4-2], wherein the restoration process is denoising restoration or data error feedback restoration.

[Appendix 4-4]

The medical data processing apparatus according to [Appendix 4-1], wherein the imaging parameter includes at least one of a slice position, imaging principle and temporal resolution of medical data.

[Appendix 4-5]

The medical data processing apparatus according to [Appendix 4-4], wherein an amount of under-sampled data is larger in the first medical data than in the second medical data.

[Appendix 4-6]

The medical data processing apparatus according to [Appendix 4-1], wherein each of the first medical data and the second medical data is entered as a single input vector to the learned model.

[Appendix 4-7]

The medical data processing apparatus according to [Appendix 4-6], wherein the first medical data is assigned to a first region of the input vector, the second medical data is assigned to a second region of the input vector, and positions of the first region and the second region are fixed.

[Appendix 4-8]

The medical data processing apparatus according to [Appendix 4-7], wherein the second medical data includes a plurality of sets of medical data having different imaging parameters, and each of the sets of second medical data is assigned to a fixed region of the second region of the input vector.

[Appendix 4-9]

The medical data processing apparatus according to [Appendix 4-1], further comprising training circuitry configured to generate estimated output data by applying the first medical data and the second medical data to a parameter-added composite function obtained by combining a plurality of functions and to generate the learned model by updating parameters of the parameter-added composite function such that the estimated output data and true output data approximate each other.

[Appendix 4-10]

The medical data processing apparatus according to [Appendix 4-1], wherein the processing circuitry is configured to:

select an imaging body part in accordance with user's instructions, and switch learned models in accordance with the selected imaging body part.

[Appendix 4-11]

The medical data processing apparatus according to [Appendix 4-1], wherein the imaging parameter includes a first parameter and a second parameter, the first medical data and the second medical data share the first parameter and have different second parameters, the first medical data and the third medical data share the first parameter and the second parameter, the second medical data and the third medical data share the first parameter and have different second parameters, and the third medical data includes less data deficit or higher image quality than the first medical data.

[Appendix 4-12]

The medical data processing apparatus according to [Appendix 4-11], wherein the first parameter represents a slice position, and the second parameter represents an imaging principle of the medical data.

[Appendix 4-13]

The medical data processing apparatus according to [Appendix 4-12], wherein the second parameter relating to the first medical data represents PET imaging as the imaging principle, and the second parameter relating to the second medical data represents X-ray CT imaging as the imaging principle.

[Appendix 4-14]

A medical image diagnostic apparatus comprising:

a memory configured to store a learned model including an input layer to which first medical data and second medical data relating to an imaging target the same as the first medical data and an imaging parameter different from the first medical data are inputted, an output layer from which third medical data is output with a missing portion of the first medical data restored, and at least one intermediate layer arranged between the input layer and the output layer; and processing circuitry configured to:

acquire the first medical data relating to a first imaging parameter and the second medical data relating to a second imaging parameter that is different from the first imaging parameter by performing imaging on a subject; and generate third medical data relating to the subject from the acquired first medical data and the acquired second medical data in accordance with the learned model.

[Appendix 4-15]

The medical image diagnostic apparatus according to [Appendix 4-14], further comprising a PET scanner configured to perform PET imaging on the subject and acquire the first medical data and an X-ray CT scanner configured to perform X-ray CT imaging on the subject and acquire the second medical data.

[Appendix 4-16]

A learned model generating method comprising:

generating estimated output data by applying first medical data and second medical data relating to an imaging target the same as the first medical data and an imaging parameter different from the first medical data to a parameter-added composite function obtained by combining a plurality of functions; and generating a learned model by updating parameters of the parameter-added composite function such that the estimated output data and true output data having a missing portion of the first medical data restored approximate each other.

The invention claimed is:

1. A medical data processing apparatus comprising:
a memory configured to store a learned model including an input layer to which first CT data and second CT data relating to an imaging target the same as the first CT data and an imaging parameter different from the first CT data are inputted, an output layer from which third CT data with a missing portion of the first CT data restored is output, and at least one intermediate layer arranged between the input layer and the output layer; and
processing circuitry configured to generate third CT data relating to a subject in accordance with the learned model, from the first CT data serving as a process target and relating to the subject, and the second CT data relating to the subject and acquired with the imaging parameter different from the first CT data relating to the process target.

2. A medical data processing apparatus comprising:
a memory configured to store a learned model including an input layer to which first CT data and second CT data relating to an imaging target the same as the first CT data and an imaging parameter different from the first CT data are inputted, an output layer from which third CT data with a missing portion of the first CT data restored is output, and at least one intermediate layer arranged between the input layer and the output layer; and
processing circuitry configured to generate third CT data relating to a subject in accordance with the learned model, from the first CT data serving as a process target and relating to the subject, and the second CT data relating to the subject and acquired with the imaging parameter different from the first CT data relating to the process target,
wherein the first CT data and the second CT data are projection data or CT image data generated by performing a restoration process on the projection data.

3. The medical data processing apparatus according to claim 2, wherein the restoration process is denoising restoration or data error feedback restoration.

4. The medical data processing apparatus according to claim 1, wherein the imaging parameter includes at least one of a slice position, acquisition time, tube current, tube voltage, focus size, spatial resolution of a detector, number of views, reconstruction function, gantry rotation velocity and temporal resolution.

5. The medical data processing apparatus according to claim 4, wherein an amount of under-sampled data is larger in the first CT data than in the second CT data.

6. The medical data processing apparatus according to claim 1, wherein the first CT data and the second CT data are inputted to the learned model as a single input vector.

7. The medical data processing apparatus according to claim 6, wherein
the first CT data is assigned to a first region of the input vector,
the second CT data is assigned to a second region of the input vector, and
positions of the first region and the second region are fixed.

8. The medical data processing apparatus according to claim 7, wherein
the second CT data includes a plurality of sets of CT data having different imaging parameters, and
each of the sets of second CT data is assigned to a fixed region of the second region of the input vector.

9. The medical data processing apparatus according to claim 1, further comprising training circuitry configured to generate estimated output data by applying the first CT data and the second CT data to a parameter-added composite function obtained by combining a plurality of functions, and generate the learned model by updating parameters of the parameter-added composite function such that the estimated output data and true output data approximate each other.

10. The medical data processing apparatus according to claim 1, wherein the processing circuitry is configured to:
select an imaging body part in accordance with user's instructions; and
switch learned models in accordance with the selected imaging body part.

11. The medical data processing apparatus according to claim 1, wherein the imaging parameter includes a first parameter and a second parameter,
the first CT data and the second CT data share the first parameter and have different second parameters,
the first CT data and the third CT data share the first parameter and the second parameter,
the second CT data and the third CT data share the first parameter and have different second parameters, and
the third CT data includes less data deficit or higher image quality than the first CT data.

12. The medical data processing apparatus according to claim 11, wherein
the first parameter represents a slice position, and
the second parameter represents an acquisition time and a tube current.

13. An X-ray computed tomography imaging apparatus, comprising:
a memory configured to store a learned model comprising an input layer to which first projection data or CT image data and second projection data or CT image data relating to an imaging target the same as the first projection data or CT image data and an imaging parameter different from the first projection data or CT image data are inputted, an output layer from which third projection data or CT image data is output with a missing portion of the first projection data or CT image data restored, and at least one intermediate layer arranged between the input layer and the output layer, and
processing circuitry configured to:
acquire the first projection data relating to a first imaging parameter by performing CT imaging on a subject, and the second projection data relating to a second imaging parameter different from the first imaging parameter; and
generate the third projection data or CT image data relating to the subject from the acquired first projection data or CT image data and the acquired second projection data or CT image data, in accordance with the learned model.

14. An X-ray computed tomography imaging apparatus, comprising:
a memory configured to store a learned model comprising an input layer to which first projection data or CT image data and second projection data or CT image data relating to an imaging target the same as the first projection data or CT image data and an imaging parameter different from the first projection data or CT image data are inputted, an output layer from which third projection data or CT image data is output with a missing portion of the first projection data or CT image data restored, and at least one intermediate layer arranged between the input layer and the output layer; and processing circuitry configured to:
acquire the first projection data relating to a first imaging parameter by performing CT imaging on a subject, and the second projection data relating to a second imaging parameter different from the first imaging parameter,
generate the third projection data or CT image data relating to the subject from the acquired first projection data or CT image data and the acquired second projection data or CT image data, in accordance with the learned model,
acquire projection data of a plurality of rotations of a rotation frame,
generate first rotation CT image data as the first CT image data, based on projection data of a first rotation from among the projection data of the rotations, and
generate second rotation CT image data as the second CT image data, based on projection data of a second rotation from among the projection data of the rotations.

15. An X-ray computed tomography imaging apparatus, comprising:
a memory configured to store a learned model comprising an input layer to which first projection data or CT image data and second projection data or CT image data relating to an imaging target the same as the first projection data or CT image data and an imaging parameter different from the first projection data or CT image data are inputted, an output layer from which third projection data or CT image data is output with a missing portion of the first projection data or CT image data restored, and at least one intermediate layer arranged between the input layer and the output layer; and processing circuitry configured to:
acquire the first projection data relating to a first imaging parameter by performing CT imaging on a subject, and the second projection data relating to a second imaging parameter different from the first imaging parameter,
generate the third projection data or CT image data relating to the subject from the acquired first projection data or CT image data and the acquired second projection data or CT image data, in accordance with the learned model,
acquire projection data of a plurality of rotations of a rotation frame,
generate first rotation CT image data as the first CT image data, based on projection data of a first rotation from among the projection data of the rotations, and
generate second rotation CT image data as the second CT image data, based on projection data of a second rotation from among the projection data of the rotations, wherein
the first rotation projection data is generated by high-dose CT imaging, and
the second rotation projection data is generated by low-dose CT imaging.

16. A learned model generating method, comprising steps of:
generating estimated output data by applying first CT data and second CT data relating to an imaging target the same as the first CT data and an imaging parameter different from the first CT data to a parameter-added composite function obtained by combining a plurality of functions; and
generating a learned model by updating parameters of the parameter-added composite function such that the estimated output data and true output data having a missing portion of the first CT data restored approximate each other.

* * * * *